(12) United States Patent
Nerelius et al.

(10) Patent No.: US 9,573,994 B2
(45) Date of Patent: Feb. 21, 2017

(54) Aβ PROTOFIBRIL BINDING ANTIBODIES

(71) Applicants: BioArctic Neuroscience AB, Stockholm (SE); Eisai R&D Management Co., Ltd., Tokyo (JP)

(72) Inventors: Charlotte Nerelius, Uppsala (SE); Hanna Laudon, Nacka (SE); Jessica Sigvardson, Spånga (SE)

(73) Assignees: BioArctic Neuroscience AB, Stockholm (SE); Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 14/794,172

(22) Filed: Jul. 8, 2015

(65) Prior Publication Data
US 2016/0009793 A1    Jan. 14, 2016

Related U.S. Application Data

(60) Provisional application No. 62/022,952, filed on Jul. 10, 2014.

(51) Int. Cl.
| | | |
|---|---|---|
| *C07K 16/18* | (2006.01) | |
| *A61K 39/395* | (2006.01) | |
| *G01N 33/50* | (2006.01) | |
| *G01N 33/68* | (2006.01) | |
| *C07K 16/46* | (2006.01) | |
| *A61K 39/00* | (2006.01) | |

(52) U.S. Cl.
CPC ........... *C07K 16/18* (2013.01); *C07K 16/465* (2013.01); *G01N 33/6896* (2013.01); *A61K 2039/505* (2013.01); *C07K 2317/24* (2013.01); *C07K 2317/565* (2013.01); *C07K 2317/567* (2013.01); *C07K 2317/94* (2013.01); *G01N 2333/4709* (2013.01); *G01N 2800/2821* (2013.01)

(58) Field of Classification Search
CPC ............... C07K 16/18; C07K 2317/56; C07K 2317/565; C07K 2317/24; C07K 2317/94; C07K 2317/567; A61K 2039/505; A61K 39/3955; G01N 33/6896; G01N 2333/4709; G01N 2800/2821
See application file for complete search history.

(56) References Cited

U.S. PATENT DOCUMENTS

| | | | |
|---|---|---|---|
| 5,231,000 A | 7/1993 | Majocha et al. | |
| 5,604,102 A | 2/1997 | McConlogue et al. | |
| 5,612,486 A | 3/1997 | McConlogue et al. | |
| 5,679,531 A | 10/1997 | Konig et al. | |
| 5,753,624 A | 5/1998 | McMichael et al. | |
| 5,817,626 A | 10/1998 | Findeis et al. | |
| 5,850,003 A | 12/1998 | McLonlogue et al. | |
| 5,851,996 A | 12/1998 | Kline | |
| 5,854,204 A | 12/1998 | Findeis et al. | |
| 5,854,215 A | 12/1998 | Findeis et al. | |
| 5,985,242 A | 11/1999 | Findeis et al. | |
| 6,054,114 A | 4/2000 | Lansbury, Jr. et al. | |
| 6,114,133 A | 9/2000 | Seubert et al. | |
| 6,174,916 B1 | 1/2001 | McMichael | |
| 6,218,506 B1 | 4/2001 | Krafft et al. | |
| 6,245,964 B1 | 6/2001 | McLonlogue et al. | |
| 6,303,567 B1 | 10/2001 | Findeis et al. | |
| 6,319,498 B1 | 11/2001 | Findeis et al. | |
| 7,179,463 B2 | 2/2007 | Lannfelt et al. | |
| 7,427,392 B1 | 9/2008 | Seubert et al. | |
| 7,700,719 B2 | 4/2010 | Lannfelt et al. | |
| 8,025,878 B2 | 9/2011 | Gellerfors et al. | |
| 8,106,164 B2 | 1/2012 | Gellerfors et al. | |
| 8,404,459 B2 | 3/2013 | Gellerfors et al. | |
| 8,409,575 B2 | 4/2013 | Lannfelt et al. | |
| 8,999,936 B2 | 4/2015 | Gellerfors et al. | |
| 9,034,334 B2 | 5/2015 | Gellerfors et al. | |
| 2002/0162129 A1 | 10/2002 | Lannfelt et al. | |
| 2003/0068316 A1 | 4/2003 | Klein et al. | |
| 2003/0187011 A1 | 10/2003 | Lashuel et al. | |
| 2003/0232758 A1 | 12/2003 | St. George-Hyslop et al. | |
| 2004/0049134 A1 | 3/2004 | Tosaya et al. | |
| 2004/0170641 A1 | 9/2004 | Schenk | |
| 2004/0171815 A1 | 9/2004 | Schenk et al. | |
| 2004/0171816 A1 | 9/2004 | Schenk et al. | |
| 2005/0031629 A1 | 2/2005 | Schenk | |
| 2005/0124016 A1 | 6/2005 | LaDu et al. | |

(Continued)

FOREIGN PATENT DOCUMENTS

| | | |
|---|---|---|
| EP | 0526511 A1 | 2/1993 |
| EP | 0783104 A1 | 7/1997 |

(Continued)

OTHER PUBLICATIONS

European Search Report and Search Opinion for European Patent Application No. 10195985, dated Jul. 4, 2011 (7 pages).
Extended European Search Report for European Patent Application No. 08019830, dated May 31, 2010 (13 pages).
Advisory Action for U.S. Appl. No. 09/899,815, mailed Feb. 20, 2004 (3 pages).
Andreasen et al., "Beta-amyloid (Abeta) protein in cerebrospinal fluid as a biomarker for Alzheimer's disease," Peptides. 23(7):1205-14 (2002).
Axelman et al., "A large Swedish family with Alzheimer's disease with a codon 670/671 amyloid precursor protein mutation. A clinical and genealogical investigation," Arch Neurol. 51(12):1193-7 (1994).
Bacskai et al., "Imaging of amyloid-beta deposits in brains of living mice permits direct observation of clearance of plaques with immunotherapy," Nat Med. 7(3):369-72 (2001).

(Continued)

*Primary Examiner* — Kimberly A. Ballard
(74) *Attorney, Agent, or Firm* — Clark & Elbing LLP; Susan M. Michaud

(57) ABSTRACT

The present invention relates to the amyloid beta peptide (Aβ) and more specifically to antibodies binding to Aβ protofibrils and their use in therapy and/or prophylactic treatment of Alzheimer's disease and other disorders associated with Aβ protein aggregation. Further the invention may relate to diagnosis of such diseases as well as monitoring of disease progression by use of the antibodies of the invention. Further, the invention may relate to veterinary use of the antibodies of the invention.

25 Claims, 12 Drawing Sheets

(56) References Cited

U.S. PATENT DOCUMENTS

| | | | |
|---|---|---|---|
| 2005/0142132 A1 | 6/2005 | Schenk et al. | |
| 2005/0191314 A1 | 9/2005 | Schenk | |
| 2005/0249725 A1 | 11/2005 | Schenk et al. | |
| 2005/0255113 A1 | 11/2005 | Huston et al. | |
| 2006/0079447 A1 | 4/2006 | Wetzel | |
| 2006/0166275 A1 | 7/2006 | Krafft et al. | |
| 2006/0178302 A1 | 8/2006 | Krafft et al. | |
| 2006/0193850 A1 | 8/2006 | Warne et al. | |
| 2006/0228349 A1 | 10/2006 | Acton et al. | |
| 2006/0240486 A1 | 10/2006 | Johnson-Wood et al. | |
| 2006/0280733 A1 | 12/2006 | Kayed et al. | |
| 2007/0048312 A1 | 3/2007 | Klein et al. | |
| 2007/0081998 A1 | 4/2007 | Kinney et al. | |
| 2007/0098721 A1 | 5/2007 | Hillen et al. | |
| 2007/0099185 A1 | 5/2007 | Hagen et al. | |
| 2007/0110750 A1 | 5/2007 | Glabe et al. | |
| 2007/0148167 A1 | 6/2007 | Strohl | |
| 2007/0248606 A1 | 10/2007 | Lannfelt et al. | |
| 2008/0181902 A1 | 7/2008 | Lannfelt et al. | |
| 2009/0155246 A1 | 6/2009 | Gellerfors et al. | |
| 2009/0258009 A1 | 10/2009 | Gellerfors et al. | |
| 2011/0076275 A1 | 3/2011 | Igawa et al. | |
| 2012/0009180 A1* | 1/2012 | Kubota | C07K 16/18 424/133.1 |
| 2012/0027755 A1 | 2/2012 | Lannfelt et al. | |
| 2012/0076726 A1 | 3/2012 | Gellerfors et al. | |
| 2012/0100129 A1 | 4/2012 | Gellerfors et al. | |
| 2012/0156222 A1 | 6/2012 | Lannfelt | |
| 2012/0230912 A1 | 9/2012 | Gellerfors et al. | |
| 2013/0236452 A1 | 9/2013 | Gellerfors et al. | |
| 2015/0307601 A1 | 10/2015 | Gellerfors et al. | |

FOREIGN PATENT DOCUMENTS

| | | |
|---|---|---|
| EP | 2004688 A1 | 12/2008 |
| WO | WO-91/16819 A1 | 11/1991 |
| WO | WO-95/11994 A1 | 5/1995 |
| WO | WO-95/31996 A1 | 11/1995 |
| WO | WO-96/15452 A1 | 5/1996 |
| WO | WO-97/41856 A1 | 11/1997 |
| WO | WO-98/33815 A1 | 8/1998 |
| WO | WO-99/27944 A1 | 6/1999 |
| WO | WO-99/27949 A1 | 6/1999 |
| WO | WO-00/39310 A1 | 7/2000 |
| WO | WO-00/71671 A2 | 11/2000 |
| WO | WO-00/72870 A1 | 12/2000 |
| WO | WO-00/72876 A2 | 12/2000 |
| WO | WO-00/72880 A2 | 12/2000 |
| WO | WO-01/10900 A2 | 2/2001 |
| WO | WO-01/39796 A2 | 6/2001 |
| WO | WO-01/90182 A2 | 11/2001 |
| WO | WO-02/03911 A2 | 1/2002 |
| WO | WO-03/089460 A1 | 10/2003 |
| WO | WO-03/104437 A2 | 12/2003 |
| WO | WO-2004/024090 A2 | 3/2004 |
| WO | WO-2004/031400 A2 | 4/2004 |
| WO | WO-2005/019828 A1 | 3/2005 |
| WO | WO-2005/025516 A2 | 3/2005 |
| WO | WO-2005/089539 A1 | 9/2005 |
| WO | WO-2005/123775 A1 | 12/2005 |
| WO | WO-2006/014478 A1 | 2/2006 |
| WO | WO-2006/047254 A1 | 5/2006 |
| WO | WO-2006/055178 A2 | 5/2006 |
| WO | WO-2006/066233 A1 | 6/2006 |
| WO | WO-2006/083533 A2 | 8/2006 |
| WO | WO-2006/094724 A2 | 9/2006 |
| WO | WO-2006/137354 A1 | 12/2006 |
| WO | WO-2007/005358 A2 | 1/2007 |
| WO | WO-2007/005359 A1 | 1/2007 |
| WO | WO-2007/050359 A2 | 5/2007 |
| WO | WO-2007/062088 A1 | 5/2007 |
| WO | WO-2007/108756 A1 | 9/2007 |
| WO | WO-2009/065054 A2 | 5/2009 |
| WO | WO-2009/133521 A2 | 11/2009 |
| WO | WO-2010/111367 A1 | 9/2010 |
| WO | WO-2011/001366 A1 | 1/2011 |
| WO | WO-2012/083370 A1 | 6/2012 |

OTHER PUBLICATIONS

Bard et al., "Peripherally administered antibodies against amyloid beta-peptide enter the central nervous system and reduce pathology in a mouse model of Alzheimer disease," Nat Med. 6(8):916-9 (2000).

Barghorn et al., "Globular amyloid beta-peptide oligomer—a homogenous and stable neuropathological protein in Alzheimer's disease," J Neurochem. 95(3):834-47 (2005).

Bayer et al., "Evaluation of the safety and immunogenicity of synthetic Abeta42 (AN1792) in patients with AD," Neurology. 64(1):94-101 (2005).

Bieschke et al., "Small molecule oxidation products trigger disease-associated protein misfolding," Acc Chem Res. 39(9):611-9 (2006).

Bitan et al., "Amyloid beta -protein (Abeta) assembly: Abeta 40 and Abeta 42 oligomerize through distinct pathways," Proc Natl Acad Sci U.S.A. 100(1):330-5 (2003).

Blanchard et al., "Efficient reversal of Alzheimer's disease fibril formation and elimination of neurotoxicity by a small molecule," Proc Natl Acad Sci U.S.A.101(40):14326-32 (2004).

Cai et al., "Release of excess amyloid beta protein from a mutant amyloid beta protein precursor," Science. 259(5094):514-6 (1993).

Caughey et al., "Protofibrils, pores, fibrils, and neurodegeneration: separating the responsible protein aggregates from the innocent bystanders," Annu Rev Neurosci. 26:267-98 (2003).

Cayman Chemical Catalog No. 32100, CAS Registry No. 75899-68-2. Apr. 12, 2009 (1 page).

Cayman Chemical Catalog No. 32100, CAS Registry No. 75899-68-2, Copyright Cayman Chemical Company, May 16, 2006 (1 page).

Chartier-Harlin et al., "Alpha-synuclein locus duplication as a cause of familial Parkinson's disease," Lancet. 364(9440):1167-9 (2004).

Chen et al., "A learning deficit related to age and beta-amyloid plaques in a mouse model of Alzheimer's disease," Nature. 408(6815):975-9 (2000).

Chromy et al., "Self-assembly of Abeta(1-42) into globular neurotoxins," Biochemistry. 42(44):12749-60 (2003).

Chromy et al., "Stability of small oligomers of Abeta(1-42) (ADDLs)," Society for Neuroscience. 25:2129, Abstract No. 852.5 (1999).

Citron et al., "Mutant presenilins of Alzheimer's disease increase production of 42-residue amyloid beta-protein in both transfected cells and transgenic mice," Nat Med. 3(1):67-72 (1997).

Citron et al., "Mutation of the beta-amyloid precursor protein in familial Alzheimer's disease increases beta-protein production," Nature. 360(6405):672-4 (1992).

Communication for European Patent Application No. 10739701.0, dated Jul. 29, 2014 (6 pages).

Conway et al., "Acceleration of oligomerization, not fibrillization, is a shared property of both alpha-synuclein mutations linked to early-onset Parkinson's disease: implications for pathogenesis and therapy," Proc Natl Acad Sci U.S.A. 97(2):571-6 (2000).

Dahlgren et al., "Oligomeric and fibrillar species of amyloid-beta peptides differentially affect neuronal viability," J Biol Chem. 277(35):32046-53 (2002).

Dalfó et al., "Evidence of oxidative stress in the neocortex in incidental Lewy body disease," J Neuropathol Exp Neurol. 64(9):816-30 (2005).

De Jonghe et al., "Flemish and Dutch mutations in amyloid beta precursor protein have different effects on amyloid beta secretion," Neurobiol Dis. 5(4):281-6 (1998).

Declaration of Anders Lindgren and Lars Lannfelt accompanying Response in connection to Communication pursuant to Article 94(3) EPC for European Patent Application No. 05753672.4 dated Mar. 22, 2012 as filed May 30, 2012 with the European Patent Office (4 pages).

Declaration of Lars Lannfelt for European Patent Application No. 01945896.7 submitted on Sep. 22, 2006 (2 pages).

(56) References Cited

OTHER PUBLICATIONS

Declaration of Lars Lannfelt filed in U.S. Appl. No. 09/899,815, dated Mar. 7, 2006 (3 pages).
Declaration of Pär Gellerfors for U.S. Appl. No. 12/294,207, dated Nov. 28, 2010 (2 pages).
Declaration of William Goure dated Feb. 22, 2013 (12 pages).
DeMarco et al., "From conversion to aggregation: protofibril formation of the prion protein," Proc Natl Acad Sci U.S.A. 101(8):2293-8 (2004).
Dodart et al., "Immunization reverses memory deficits without reducing brain Abeta burden in Alzheimer's disease model," Nat Neurosci. 5(5):452-7 (2002).
El-Agnaf et al., "Detection of oligomeric forms of alpha-synuclein protein in human plasma as a potential biomarker for Parkinson's disease," Faseb J. 20(3):419-25 (2006).
El-Agnaf et al. "Oligomerization and toxicity of beta-amyloid-42 implicated in Alzheimer's disease," Biochem Biophys Res Commun. 273(3):1003-7 (2000).
English language translation of the Notice of Preliminary Rejection for Japanese Patent Application No. 2012-516964, mailed Jul. 22, 2014 (6 pages).
Englund et al., "Sensitive ELISA detection of amyloid-beta protofibrils in biological samples," J Neurochem. 103(1):334-45 (2007).
Enya et al., "Appearance of sodium dodecyl sulfate-stable amyloid beta-protein (Abeta) dimer in the cortex during aging," Am J Pathol. 154(1):271-9 (1999).
Final Office Action for U.S. Appl. No. 11/570,995, mailed Oct. 19, 2010 (8 pages).
Final Office Action for U.S. Appl. No. 13/780,643, mailed Apr. 7, 2014 (7 pages).
Finder et al., "Amyloid-beta aggregation," Neurodegener Dis. 4(1):13-27 (2007).
Foote et al., "Antibody framework residues affecting the conformation of the hypervariable loops," J Mol Biol. 224(2):487-99 (1992).
Forsell et al., "Amyloid precursor protein mutation at codon 713 (Ala—>Val) does not cause schizophrenia: non-pathogenic variant found at codon 705 (silent)," Neurosci Lett. 184(2):90-3 (1995).
Frackowiak et al., "Non-fibrillar beta-amyloid protein is associated with smooth muscle cells of vessel walls in Alzheimer disease," J Neuropathol Exp Neurol. 53(6):637-45 (1994).
Frank, Specificity and Cross-Reactivity. *Immunology and Evolution of Infectious Disease*. Princeton University Press, 35-6 (2002).
Frenkel et al., "Immunization against Alzheimer's beta-amyloid plaques via EFRH phage administration," Proc Natl Acad Sci U.S.A. 97(21):11455-9 (2000).
Frenkel et al., "Modulation of Alzheimer's beta-amyloid neurotoxicity by site-directed single-chain antibody," J. Neuroimmunol. 106(1-2):23-31 (2000).
Frenkel et al., "Modulation of Alzheimer's Beta-amyloid Neurotoxicity by Site-directed Single-chain Antibody," Neuroimmunomodulation. 6:444 (1999).
Giasson et al., "A panel of epitope-specific antibodies detects protein domains distributed throughout human alpha-synuclein in Lewy bodies of Parkinson's disease," J Neurosci Res. 59(4):528-33 (2000).
Giulian et al., "The HHQK domain of beta-amyloid provides a structural basis for the immunopathology of Alzheimer's disease," J Biol Chem. 273(45):29719-26 (1998).
Glenner et al., "Alzheimer's disease: initial report of the purification and characterization of a novel cerebrovascular amyloid protein," Biochem Biophys Res Commun. 120(3):885-90 (1984).
Golabek et al., "The interaction between apolipoprotein E and Alzheimer's amyloid beta-peptide is dependent on beta-peptide conformation," J Biol Chem. 271(18):10602-6 (1996).
Goldsby et al., Immunoglobulins: Structure and Function. *Kuby Immunology*. W.H. Freeman and Company, 85 (2000) (3 pages).

Grabowski et al., "Novel amyloid precursor protein mutation in an Iowa family with dementia and severe cerebral amyloid angiopathy," Ann Neurol. 49(6):697-705 (2001).
Guerette et al., "Oligomeric Abeta in PBS-soluble extracts of human Alzheimer brain," Society for Neuroscience. 25:2129 (1999).
Hansen et al., "The Lewy body variant of Alzheimer's disease: a clinical and pathologic entity," Neurology. 40(1):1-8 (1990).
Hardy, "Amyloid, the presenilins and Alzheimer's disease," Trends Neurosci. 20(4):154-9 (1997).
Hardy, "Framing beta-amyloid," Nat Genet. 1(4):233-4 (1992).
Harlow et al., Reagents. Antibodies: A Laboratory Manual. Cold Spring Harbor Laboratory Press, 626-31 (1988) (8 pages).
Harper et al., "Assembly of A beta amyloid protofibrils: an in vitro model for a possible early event in Alzheimer's disease," Biochemistry. 38(28):8972-80 (1999).
Harper et al., "Observation of metastable Abeta amyloid protofibrils by atomic force microscopy," Chem Biol. 4(2):119-25 (1997).
Hartley et al., "Protofibrillar intermediates of amyloid beta-protein induce acute electrophysiological changes and progressive neurotoxicity in cortical neurons," J Neurosci. 19(20):8876-84 (1999).
Hendriks et al., "Presenile dementia and cerebral haemorrhage linked to a mutation at codon 692 of the beta-amyloid precursor protein gene," Nat Genet. 1(3):218-21 (1992).
Higuchi, "Evaluation of Alzheimer's disease using neuroimaging agents and biological markers," Experimental Medicine. 26:2582-8, English translation (2008) (4 pages).
Hock et al., "Clinical observations with AN-1792 using TAPIR analyses," Neurodegener Dis. 2(5):273-6 (2005).
Hoshi et al., "Spherical aggregates of beta-amyloid (amylospheroid) show high neurotoxicity and activate tau protein kinase I/glycogen synthase kinase-3beta," Proc Natl Acad Sci U.S.A. 100(11):6370-5 (2003).
International Preliminary Report on Patentability for PCT/SE01/01553, completed Oct. 23, 2002 (8 pages).
International Preliminary Report on Patentability for PCT/SE2005/000993, issued Dec. 28, 2006 (16 pages).
International Preliminary Report on Patentability for PCT/SE2007/000292, issued Sep. 23, 2008 (10 pages).
International Preliminary Report on Patentability for PCT/US03/19640, completed Aug. 7, 2006 (4 pages).
International Preliminary Report on Patentability for PCT/US03/30930, completed Feb. 6, 2006 (5 pages).
International Search Report for PCT/SE01/01553, mailed Feb. 4, 2002 (8 pages).
International Search Report for PCT/SE2005/000993, mailed Oct. 4, 2005 (6 pages).
International Search Report for PCT/SE2007/000292, mailed Jul. 20, 2007 (6 pages).
Interview Summary for U.S. Appl. No. 09/899,815, mailed Oct. 23, 2003 (2 pages).
Isaacs et al., "Acceleration of amyloid beta-peptide aggregation by physiological concentrations of calcium," J Biol Chem. 281(38):27916-23 (2006) (17 pages).
Janeway et al., Structure of the Antibody Molecule and the Immunoglobulin Genes. *Immunobiology: The Immune System in Health and Disease*. Elsevier Science Ltd, 82-3 (1999) (4 pages).
Janus et al., "A beta peptide immunization reduces behavioural impairment and plaques in a model of Alzheimer's disease," Nature. 408(6815):979-82 (2000).
Jefferis, "Glycosylation as a strategy to improve antibody-based therapeutics," Nat Rev Drug Discov. 8(3):226-34 (2009).
Jensen et al., "Quantification of Alzheimer amyloid beta peptides ending at residues 40 and 42 by novel ELISA systems," Mol Med. 6(4):291-302 (2000).
Johansson et al., "Physiochemical characterization of the Alzheimer's disease-related peptides A beta 1-42Arctic and A beta 1-42wt," FEBS J. 273(12):2618-30 (2006).
Johnston et al., "Increased beta-amyloid release and levels of amyloid precursor protein (APP) in fibroblast cell lines from family members with the Swedish Alzheimer's disease APP670/671 mutation," FEBS Lett. 354(3):274-8 (1994).

(56) References Cited

OTHER PUBLICATIONS

Kamino et al., "Linkage and mutational analysis of familial Alzheimer disease kindreds for the APP gene region," Am J Hum Genet. 51(5):998-1014 (1992).
Kang et al., "The precursor of Alzheimer's disease amyloid A4 protein resembles a cell-surface receptor," Nature. 325(6106):733-6 (1987).
Kayed et al., "Common structure of soluble amyloid oligomers implies common mechanism of pathogenesis," Science. 300(5618):486-9 (2003).
Kayed et al., "Immunization With a Molecular Mimic of a Toxic Aggregates Generates a Conformation-Dependent Antibody Specific for High Molecular Weight A Aggregates (Micelles and Protofibrils)," 32nd Annual Meeting of the Society for Neuroscience, Orlando, FL 2002:29, Abstract No. 685.3 (2002).
Kirkitadze et al., "Paradigm shifts in Alzheimer's disease and other neurodegenerative disorders: the emerging role of oligomeric assemblies," J Neurosci Res. 69(5):567-77 (2002).
Klafki et al., "Therapeutic approaches to Alzheimer's disease," Brain. 129(Pt 11):2840-55 (2006).
Klein et al., "Oligemia-induced expression of c-Fos and oxidative stress-related protein in the murine brain," 30th Annual Meeting of the Society of Neuroscience, New Orleans, LA, Nov. 4-9, 2000, Society of Neuroscience Abstracts 26(1-2), Abstract No. 383.15 (2000) (2 pages).
Klein et al., "Oligomer/conformation-dependent Abeta antibodies," Society for Neuroscience Abstract Presentation No. 475.11, Nov. 7, 2000 (2 pages).
Klein et al., "Targeting small Abeta oligomers: the solution to an Alzheimer's disease conundrum?" Trends Neurosci. 24(4):219-24 (2001).
Klein, Abeta Toxicity in Alzheimer's Disease. *Contemporary Clinical Neuroscience: Molecular Mechanisms of Neurodegenerative Diseases*. Humana Press, 1-49 (2001).
Klucken et al., "Clinical and biochemical correlates of insoluble alpha-synuclein in dementia with Lewy bodies," Acta Neuropathol. 111(2):101-8 (2006).
Klyubin et al., "Inhibitory effect of amyloid-beta peptide with the Arctic mutuation on long-term potentiation in area CA1 of rat hippocampus in vivo," J Physiol 551 P,C32 (2003) (1 page).
Klyubin et al., "Soluble Arctic amyloid beta protein inhibits hippocampal long-term potentiation in vivo," Eur J Neurosci. 19(10):2839-46 (2004).
Krüger et al., "Ala30Pro mutation in the gene encoding alpha-synuclein in Parkinson's disease," Nat Genet.18(2):106-8 (1998).
Kuo et al., "Water-soluble Abeta (N-40, N-42) oligomers in normal and Alzheimer disease brains," J Biol Chem. 271(8):4077-81 (1996).
Lambert et al., "Diffusible, nonfibrillar ligands derived from Abeta1-42 are potent central nervous system neurotoxins," Proc Natl Acad Sci U.S.A. 95(11):6448-53 (1998).
Lambert et al., "Monoclonal antibodies that target pathological assemblies of Abeta," J. Neurochem. 100(1):23-35 (2007).
Lambert et al., "Neuron dysfunction and death caused by small Abeta oligomers: role of signal transduction," Society for Neuroscience. 25:2129, Abstract 852.6 (1999).
Lambert et al., "Vaccination with soluble Abeta oligomers generates toxicity-neutralizing antibodies," J Neurochem. 79(3):595-605 (2001).
Lannfelt et al., "Amyloid beta-peptide in cerebrospinal fluid in individuals with the Swedish Alzheimer amyloid precursor protein mutation," Neurosci Lett. 199(3):203-6 (1995).
Lannfelt et al., "Amyloid precursor protein mutation causes Alzheimer's disease in a Swedish family," Neurosci Lett. 168(1-2):254-6 (1994).
Lannfelt et al., "Genetics of Alzheimer's disease—routes to the pathophysiology," J Neural Transm Suppl. 59:155-61 (2000).

Lannfelt et al., "Monoclonal antibodies selective for Abeta protofibrils: detection of protofibrils and reduction of plaque burden in tg-mice models of Alzheimer's disease," SfN meeting, Oct. 17, 2006 (19 pages).
Lannfelt et al., "Sensitive detection of Alzheimer Abeta protofibrils by conformation specific ELISA," ICAD meeting, Madrid, Spain, Jul. 16, 2006 (19 pages).
Lannfelt, "Genetics, Pathophysiology and Abeta Protofibril Formation in Alzheimer's Disease," Neurobiol. Aging 25(Suppl. 2): Poster Session P2: Epidemiology and Risk Factors of Alzheimer's Disease P2-268; S308 (2004).
Lashuel et al., "Mixtures of wild-type and a pathogenic (E22G) form of Abeta40 in vitro accumulate protofibrils, including amyloid pores," J Mol Biol. 332(4):795-808 (2003).
Lee et al., "Targeting amyloid-beta peptide (Abeta) oligomers by passive immunization with a conformation-selective monoclonal antibody improves learning and memory in Abeta precursor protein (APP) transgenic mice," J Biol Chem. 281(7):4292-9 (2006).
Levy et al., "Mutation of the Alzheimer's disease amyloid gene in hereditary cerebral hemorrhage, Dutch type," Science. 248(4959):1124-6 (1990).
Liu et al., "Residues 17-20 and 30-35 of beta-amyloid play critical roles in aggregation," J Neurosci Res. 75(2):162-71 (2004).
Longo et al., "Nonfibrillar Abeta 1-42 (ADDL) Causes Aconitase Inactivation and Iron-dependent Neurotoxicity," Society for Neuroscience. 25:2129, Abstract 852.3 (1999).
Lord et al., "The Arctic Alzheimer mutation facilitates early intraneuronal Abeta aggregation and senile plaque formation in transgenic mice," Neurobiol Aging. 27(1):67-77 (2006).
Masters et al., "Amyloid plaque core protein in Alzheimer disease and Down syndrome," Proc Natl Acad Sci U.S.A. 82(12):4245-9 (1985).
McKhann et al., "Clinical diagnosis of Alzheimer's disease: report of the NINCDS-ADRDA Work Group under the auspices of Department of Health and Human Services Task Force on Alzheimer's Disease," Neurology. 34(7):939-44 (1984).
Miravalle et al., "Substitutions at codon 22 of Alzheimer's abeta peptide induce diverse conformational changes and apoptotic effects in human cerebral endothelial cells," J Biol Chem. 275(35):27110-6 (2000).
Morgan et al., "A beta peptide vaccination prevents memory loss in an animal model of Alzheimer's disease," Nature. 408(6815):982-5 (2000).
Moss et al., "The peptide KLVFF-K(6) promotes beta-amyloid(1-40) protofibril growth by association but does not alter protofibril effects on cellular reduction of 3-(4,5-dimethylthiazol-2-y1)-2,5-diphenyltetrazolium bromide (MTT)," Mol Pharmacol. 64(5):1160-8 (2003).
Motter et al., "Reduction of beta-amyloid peptide42 in the cerebrospinal fluid of patients with Alzheimer's disease," Ann Neurol. 38(4):643-8 (1995).
Mullan et al., "A pathogenic mutation for probable Alzheimer's disease in the APP gene at the N-terminus of beta-amyloid," Nat Genet. 1(5):345-7 (1992).
Nichols et al., "Amyloid-beta aggregates formed at polar-nonpolar interfaces differ from amyloid-beta protofibrils produced in aqueous buffers," Microsc Res Tech. 67(3-4):164-74 (2005).
Nichols et al., "Growth of beta-amyloid(1-40) protofibrils by monomer elongation and lateral association. Characterization of distinct products by light scattering and atomic force microscopy," Biochemistry. 41(19):6115-27 (2002).
Nicoll et al., "Neuropathology of human Alzheimer disease after immunization with amyloid-beta peptide: a case report," Nat Med. 9(4):448-52 (2003).
Nilsberth et al., "A Novel APP Mutation (E693G)—The Arctic Mutation, Causing Alzheimer's Disease with Vascular Symptoms," Soc Neurosci Abs. 25:297 (1999).
Nilsberth et al., "A Novel APP Mutation (E693G)—The Arctic Mutation, Causing Alzheimer's Disease with Vascular Symptoms," Society for Neuroscience 29th Annual Meeting, Miami Beach, FL, Oct. 23-28, 1999, 25:297, Abstract 120.4 (4 pages).

(56) References Cited

OTHER PUBLICATIONS

Nilsberth et al., "The 'Arctic' APP mutation (E693G) causes Alzheimer's disease by enhanced Abeta protofibril formation," Nat Neurosci. 4(9):887-93 (2001).
Nilsberth et al., "The Arctic APP Mutation (E693G) Causes Alzheimer's Disease Through a Novel Mechanism: Increased Amyloid BetaProtfibril Formation and Decreased Amyloid BetaLevels in Plasma and Conditioned Media," Neurobiology of Aging. 21(Suppl 1):S58, Abstract 265 (May-Jun. 2000).
Non-Final Office Action for U.S. Appl. No. 11/570,995, mailed Feb. 22, 2011 (14 pages).
Non-Final Office Action for U.S. Appl. No. 11/570,995, mailed May 4, 2010 (8 pages).
Non-Final Office Action for U.S. Appl. No. 12/294,207, mailed Aug. 3, 2010 (49 pages).
Non-Final Office Action for U.S. Appl. No. 13/218,592, mailed Jul. 16, 2012 (18 pages).
Non-Final Office Action for U.S. Appl. No. 13/336,520, mailed Aug. 7, 2012 (12 pages).
Non-Final Office Action for U.S. Appl. No. 13/379,523, mailed Jul. 3, 2014 (31 pages).
Non-Final Office Action for U.S. Appl. No. 13/780,643, mailed Oct. 15, 2013 (11 pages).
Norlin et al., "Aggregation and fibril morphology of the Arctic mutation of Alzheimer's Abeta peptide by CD, TEM, STEM and in situ AFM," J Struct Biol. 180(1):174-89 (2012).
Notice of Allowance for U.S. Appl. No. 09/899,815, mailed Oct. 16, 2006 (4 pages).
Notice of Allowance for U.S. Appl. No. 11/570,995, mailed Sep. 23, 2011 (12 pages).
Notice of Allowance for U.S. Appl. No. 12/294,207, mailed Mar. 25, 2011 (22 pages).
Notice of Allowance for U.S. Appl. No. 13/218,592, mailed Jan. 22, 2013 (11 pages).
Notice of Allowance for U.S. Appl. No. 13/219,012, mailed Aug. 26, 2014 (18 pages).
Notice of Allowance for U.S. Appl. No. 13/336,520, mailed Jan. 14, 2013 (11 pages).
Notice of Allowance for U.S. Appl. No. 13/780,643, mailed Aug. 4, 2014 (14 pages).
Notice of Allowance for U.S. Appl. No. 13/780,643, mailed Nov. 21, 2014 (7 pages).
Notice of Appeal for U.S. Appl. No. 09/899,815, filed Nov. 25, 2003 (1 page).
Notice of Non-Compliant Amendment for U.S. Appl. No. 09/899,815, mailed May 12, 2005 (2 pages).
Notice of Non-Compliant Amendment for U.S. Appl. No. 11/570,995, mailed Nov. 27, 2009 (2 pages).
Notice to File Corrected Application Papers for U.S. Appl. No. 12/294,207, mailed Jun. 30, 2011 (3 pages).
Notice to File Corrected Application Papers for U.S. Appl. No. 12/294,207, mailed Jul. 15, 2011 (3 pages).
Näsström et al., "The lipid peroxidation metabolite 4-oxo-2-nonenal cross-links alpha-synuclein causing rapid formation of stable oligomers," Biochem Biophys Res Commun. 378(4):872-6 (2009).
O'Nuallain et al., "Conformational Abs recognizing a generic amyloid fibril epitope," Proc Natl Acad Sci U.S.A. 99(3):1485-90 (2002).
Oda et al., "Clusterin (apoJ) alters the aggregation of amyloid beta-peptide (A beta 1-42) and forms slowly sedimenting A beta complexes that cause oxidative stress," Exp Neurol. 136(1):22-31 (1995).
Oda et al., "Purification and characterization of brain clusterin," Biochem Biophys Res Commun. 204(3):1131-6 (1994).
Office Action for U.S. Appl. No. 09/899,815, mailed Jul. 7, 2005 (7 pages).
Office Action for U.S. Appl. No. 09/899,815, mailed Jun. 25, 2003 (9 pages).
Office Action for U.S. Appl. No. 09/899,815, mailed May 8, 2006 (5 pages).
Office Action for U.S. Appl. No. 09/899,815, mailed Nov. 19, 2002 (9 pages).
Office Action for U.S. Appl. No. 09/899,815, mailed Nov. 24, 2004 (7 pages).
Office Action for U.S. Appl. No. 09/899,815, mailed Nov. 9, 2005 (6 pages).
Office Action for U.S. Appl. No. 11/570,995, mailed Feb. 22, 2011 (15 pages).
Palmert et al., "The beta-amyloid protein precursor of Alzheimer disease has soluble derivatives found in human brain and cerebrospinal fluid," Proc Natl Acad Sci U.S.A. 86(16):6338-42 (1989).
Patent Examination Report No. 1 for Australian Patent Application No. 2010267640, dated Dec. 19, 2013 (4 pages).
Pirttilä et al., "Soluble amyloid beta-protein in the cerebrospinal fluid from patients with Alzheimer's disease, vascular dementia and controls," J Neurol Sci. 127(1):90-5 (1994).
Polymeropoulos et al., "Mutation in the alpha-synuclein gene identified in families with Parkinson's disease," Science. 276(5321):2045-7 (1997).
Ponte et al., "A new A4 amyloid mRNA contains a domain homologous to serine proteinase inhibitors," Nature. 331(6156):525-7 (1988).
Päiviö et al., "Unique physicochemical profile of beta-amyloid peptide variant Abeta1-40E22G protofibrils: conceivable neuropathogen in arctic mutant carriers," J Med Biol. 339(1):145-59 (2004).
Qin et al., "Effect of 4-hydroxy-2-nonenal modification on alpha-synuclein aggregation," J Biol Chem. 282(8):5862-70 (2007).
Reply to Notice of Non-Compliant Amendment for U.S. Appl. No. 09/899,815, filed May 27, 2005 (8 pages).
Reply to Office Action for U.S. Appl. No. 09/899,815, filed Aug. 8, 2006 (13 pages).
Reply to Office Action for U.S. Appl. No. 09/899,815, filed Dec. 18, 2003 (11 pages).
Reply to Office Action for U.S. Appl. No. 09/899,815, filed Mar. 24, 2005 (9 pages).
Reply to Office Action for U.S. Appl. No. 09/899,815, filed Mar. 9, 2006 (10 pages).
Reply to Office Action for U.S. Appl. No. 09/899,815, filed Oct. 7, 2005 (7 pages).
Reply to Office Action for U.S. Appl. No. 09/899,815, mailed Apr. 21, 2003 (16 pages).
Reply to Restriction Requirement for U.S. Appl. No. 09/899,815, dated Sep. 3, 2002 (8 pages).
Reply to Restriction Requirement for U.S. Appl. No. 09/899,815, filed Sep. 10, 2004 (8 pages).
Request for Continued Examination for U.S. Appl. No. 09/899,815, filed Mar. 25, 2004 (31 pages).
Request for Continued Examination for U.S. Appl. No. 13/780,643, dated Nov. 4, 2014 (1 page).
Response to Communication for European Patent Application No. 01945896.7, dated Jul. 2, 2014 (15 pages).
Response to Final Office Action for U.S. Appl. No. 11/570,995, filed Jan. 19, 2011 (16 pages).
Response to Final Office Action for U.S. Appl. No. 13/780,643, filed Jul. 7, 2014 (3 pages).
Response to Non-Final Office Action for U.S. Appl. No. 11/570,995, filed Jul. 12, 2011 (7 pages).
Response to Non-Final Office Action for U.S. Appl. No. 11/570,995, filed Sep. 30, 2010 (7 pages).
Response to Non-Final Office Action for U.S. Appl. No. 12/294,207, dated Jan. 3, 2011 (20 pages).
Response to Non-Final Office Action for U.S. Appl. No. 13/218,592, dated Oct. 15, 2012 (11 pages).
Response to Non-Final Office Action for U.S. Appl. No. 13/336,520, filed Nov. 7, 2012 (5 pages).
Response to Non-Final Office Action for U.S. Appl. No. 13/379,523, dated Oct. 3, 2014 (25 pages).
Response to Non-Final Office Action for U.S. Appl. No. 13/780,643, filed Feb. 18, 2014 (4 pages).
Response to Notice to File Corrected Application Papers for U.S. Appl. No. 12/294,207, dated Jul. 1, 2011 (9 pages).

(56) References Cited

OTHER PUBLICATIONS

Response to Notice to File Corrected Application Papers for U.S. Appl. No. 12/294,207, dated Jul. 29, 2011 (17 pages).
Response to Office Communication for U.S. Appl. No. 11/570,995, filed Feb. 25, 2010 (10 pages).
Response to Restriction Requirement for U.S. Appl. No. 11/570,995, filed Oct. 16, 2009 (1 page).
Response to Restriction Requirement for U.S. Appl. No. 12/294,207, dated May 12, 2010 (46 pages).
Response to Restriction Requirement for U.S. Appl. No. 13/218,592, dated Jun. 27, 2012 (1 page).
Response to Restriction Requirement for U.S. Appl. No. 13/379,523, dated Feb. 22, 2013 (8 pages).
Response to Restriction Requirement for U.S. Appl. No. 13/780,643, filed Aug. 12, 2013 (1 page).
Response to Rule 312 Communication for U.S. Appl. No. 12/294,207, mailed Aug. 3, 2011 (2 pages).
Response to Rule 312 Communication for U.S. Appl. No. 12/294,207, mailed Jul. 11, 2011 (2 pages).
Restriction Requirement for U.S. Appl. No. 09/899,815, mailed Jul. 3, 2002 (8 pages).
Restriction Requirement for U.S. Appl. No. 09/899,815, mailed Jun. 10, 2004 (5 pages).
Restriction Requirement for U.S. Appl. No. 11/570,995, mailed Jun. 22, 2009 (7 pages).
Restriction Requirement for U.S. Appl. No. 12/294,207, mailed Mar. 4, 2010 (12 pages).
Restriction Requirement for U.S. Appl. No. 13/218,592, mailed Jan. 27, 2012 (7 pages).
Restriction Requirement for U.S. Appl. No. 13/379,523, mailed Jan. 22, 2013 (7 pages).
Restriction Requirement for U.S. Appl. No. 13/780,643, mailed Jul. 11, 2013 (7 pages).
Resubmission of Reply to Office Action for U.S. Appl. No. 09/899,815, filed Feb. 3, 2004 (28 pages).
Roher et al., "Morphology and toxicity of Abeta-(1-42) dimer derived from neuritic and vascular amyloid deposits of Alzheimer's disease," J Biol Chem. 271(34):20631-5 (1996).
Russo et al., "Presenilin-1 mutations in Alzheimer's disease," Nature. 405(6786):531-2 (2000).
Rzepecki et al., "Prevention of Alzheimer's disease-associated Abeta aggregation by rationally designed nonpeptidic beta-sheet ligands," J Biol Chem. 279(46):47497-505 (2004).
Sahlin et al., "The Arctic Alzheimer mutation favors intracellular amyloid-beta production by making amyloid precursor protein less available to alpha-secretase," J Neurochem. 101(3):854-62 (2007).
Schenk et al., "Immunization with amyloid-beta attenuates Alzheimer-disease-like pathology in the PDAPP mouse," Nature. 400(6740):173-7 (1999).
Scheuner et al., "Secreted amyloid beta-protein similar to that in the senile plaques of Alzheimer's disease is increased in vivo by the presenilin 1 and 2 and APP mutations linked to familial Alzheimer's disease," Nat Med. 2(8):864-70 (1996).
Search Report and Written Opinion for Singaporean Patent Application No. 200803655-0, dated Oct. 8, 2009 (15 pages).
Sehlin et al., "Large aggregates are the major soluble Abeta species in AD brain fractionated with density gradient ultracentrifugation," PLoS One 7(2):e32014 (2012) (8 pages).
Selkoe, "Cell biology of the amyloid beta-protein precursor and the mechanism of Alzheimer's disease," Annu Rev Cell Biol. 10:373-403 (1994).
Selkoe, "Normal and abnormal biology of the beta-amyloid precursor protein," Annu Rev Neurosci. 17:489-517 (1994).
Serpell, "Alzheimer's amyloid fibrils: structure and assembly," Biochim Biophys Acta. 1502(1):16-30 (2000).
Seubert et al., "Isolation and quantification of soluble Alzheimer's beta-peptide from biological fluids," Nature. 359(6393):325-7 (1992).
Shamoto-Nagai et al. "In parkinsonian substantia nigra, alpha-synuclein is modified by acrolein, a lipid-peroxidation product, and accumulates in the dopamine neurons with inhibition of proteasome activity," J Neural Transm (Vienna). 114(12):1559-67 (2007).
Sherrington et al., "Cloning of a gene bearing missense mutations in early-onset familial Alzheimer's disease," Nature. 375(6534):754-60 (1995).
Shtilerman et al., "Molecular crowding accelerates fibrillization of alpha-synuclein: could an increase in the cytoplasmic protein concentration induce Parkinson's disease?" Biochemistry. 41(12):3855-60 (2002).
Sigurdsson et al., "Immunization with a nontoxic/nonfibrillar amyloid-beta homologous peptide reduces Alzheimer's disease-associated pathology in transgenic mice," Am J Pathol. 159(2):439-47 (2001).
Singleton et al., "alpha-Synuclein locus triplication causes Parkinson's disease," Science. 302(5646):841 (2003).
Solomon et al., "Disaggregation of Alzheimer beta-amyloid by site-directed mAb," Proc Natl Acad Sci U.S.A. 94(8):4109-12 (1997).
Solomon et al., "Monoclonal antibodies inhibit in vitro fibrillar aggregation of the Alzheimer beta-amyloid peptide," Proc Natl Acad Sci U.S.A. 93(1):452-5 (1996).
Solomon et al., "Monoclonal Antibodies Restore and Maintain the Soluble Conformation of Beta-Amyloid Peptide," Neurobiology of Aging, Fifth International Conference on Alzheimer's Disease 17(4):S152, Abstract 610 (1996).
Soto et al., "The conformation of Alzheimer's beta peptide determines the rate of amyloid formation and its resistance to proteolysis," Biochem J. 314(Pt 2):701-7 (1996).
Srinivasan et al., "ABri peptide associated with familial British dementia forms annular and ring-like protofibrillar structures," Amyloid. 11(1):10-3 (2004).
St. George-Hyslop et al., "Genetic linkage studies suggest that Alzheimer's disease is not a single homogeneous disorder," Nature. 347(6289):194-7 (1990).
St. George-Hyslop et al., "The genetic defect causing familial Alzheimer's disease maps on chromosome 21," Science. 235(4791):885-90 (1987).
Stenh et al., "Amyloid-beta oligomers are inefficiently measured by enzyme-linked immunosorbent assay," Ann Neurol. 58(1):147-50 (2005).
Stenh et al., "The Arctic mutation interferes with processing of the amyloid precursor protein," Neuroreport.13(15):1857-60 (2002).
Stine et al., "Supramolecular Structures of Abeta Aggregates and Cellular Responses," Biophysical Journal Program and Abstracts: 40th Annual Meeting, Feb. 17-21, 1996, 70:A239, Abstract Tu-AM-E1.
Stine et al., "The nanometer-scale structure of amyloid-beta visualized by atomic force microscopy," J Protein Chem. 15(2):193-203 (1996).
Studnicka et al., "Human-engineered monoclonal antibodies retain full specific binding activity by preserving non-CDR complementarity-modulating residues," Protein Eng. 7(6):805-14 (1994).
Supplemental Amendment for U.S. Appl. No. 13/336,520, dated Dec. 5, 2012 (4 pages).
Supplemental Reply for U.S. Appl. No. 13/218,592, dated Dec. 20, 2012 (4 pages).
Supplemental Reply to Restriction Requirement for U.S. Appl. No. 09/899,815, filed Sep. 21, 2004 (2 pages).
Suzuki et al., "An increased percentage of long amyloid beta protein secreted by familial amyloid beta protein precursor (beta APP717) mutants," Science. 264(5163):1336-40 (1994).
Tagliavini et al., "A New betaAPP Mutation Related to Hereditary Cerebral Haemorrhage," Alzheimers Reports. 2(Suppl 1):528, Abstract 23 (1999).
Terminology relating to clones BA2, BA3, 7E4, and 10F7, dated Sep. 18, 2009 (1 page).
Tsigelny et al., "Mechanisms of hybrid oligomer formation in the pathogenesis of combined Alzheimer's and Parkinson's diseases," PLoS One. 3(9):e3135 (2008) (15 pages).
U.S. Appl. No. 09/369,236, filed Aug. 4, 1999.
U.S. Appl. No. 09/745,057, filed Dec. 20, 2000.
U.S. Appl. No. 10/166,856, filed Jun. 11, 2002.
U.S. Appl. No. 11/570,995, filed Dec. 20, 2006.

(56) References Cited

OTHER PUBLICATIONS

U.S. Appl. No. 12/294,207, filed Sep. 23, 2008.
U.S. Appl. No. 60/217,098, filed Jul. 10, 2000.
U.S. Appl. No. 60/621,776, filed Oct. 25, 2004.
U.S. Appl. No. 60/652,538, filed Feb. 14, 2005.
Uéda et al., "Molecular cloning of cDNA encoding an unrecognized component of amyloid in Alzheimer disease," Proc Natl Acad Sci USA. 90(23):11282-6 (1993).
Vickers et al., "A vaccine against Alzheimer's disease: developments to date," Drugs Aging. 19(7):487-94 (2002).
Walsh et al., "Amyloid beta-protein fibrillogenesis. Detection of a protofibrillar intermediate," J Biol Chem. 272(35):22364-72 (1997).
Walsh et al., "Amyloid beta-protein fibrillogenesis. Structure and biological activity of protofibrillar intermediates," J Biol Chem. 274(36):25945-52 (1999).
Walsh et al., "Amyloid-beta oligomers: their production, toxicity and therapeutic inhibition," Biochem Soc Trans. 30(4):552-7 (2002).
Walsh et al., "Naturally secreted oligomers of amyloid beta protein potently inhibit hippocampal long-term potentiation in vivo," Nature. 416(6880):535-9 (2002).
Walsh et al., "Oligomers on the brain: the emerging role of soluble protein aggregates in neurodegeneration," Protein Pept Lett. 11(3):213-28 (2004).
Ward et al., "Fractionation and characterization of oligomeric, protofibrillar and fibrillar forms of beta-amyloid peptide," Biochem J. 348(Pt 1):137-44 (2000).
Weidemann et al., "Identification, biogenesis, and localization of precursors of Alzheimer's disease A4 amyloid protein," Cell. 57(1):115-26 (1989).
Weiner et al., "Nasal administration of amyloid-beta peptide decreases cerebral amyloid burden in a mouse model of Alzheimer's disease," Ann Neurol. 48(4):567-79 (2000).
Westlind-Danielsson et al., "Spontaneous in vitro formation of supramolecular beta-amyloid structures, "betaamy balls", by beta-amyloid 1-40 peptide," Biochemistry. 40(49):14736-43 (2001).
Williams et al., "Structural properties of Abeta protofibrils stabilized by a small molecule," Proc Natl Acad Sci U.S.A. 102(20):7115-20 (2005).
Wirak et al., "Deposits of amyloid beta protein in the central nervous system of transgenic mice," Science. 253(5017):323-5 (1991).
WO 2005/123775A1, pp. 7-8, published Dec. 29, 2005 (2 pages).
Written Opinion for PCT/SE2005/000993, mailed Oct. 4, 2005 (15 pages).
Written Opinion for PCT/SE2007/000292, mailed Jul. 20, 2007 (9 pages).
Xu et al., "Residue at position 331 in the IgG1 and IgG4 CH2 domains contributes to their differential ability to bind and activate complement," J Biol Chem. 269(5):3469-74 (1994).
Ye et al., "Protofibrils of amyloid beta-protein inhibit specific K+ currents in neocortical cultures," Neurobiol Dis. 13(3):177-90 (2003).
Yoritaka et al., "Immunohistochemical detection of 4-hydroxynonenal protein adducts in Parkinson disease," Proc Natl Acad Sci U.S.A. 93(7):2696-701 (1996).
Yoshikai et al., "Genomic organization of the human amyloid beta-protein precursor gene," Gene. 87(2):257-63 (1990).
Zarranz et al., "The new mutation, E46K, of alpha-synuclein causes Parkinson and Lewy body dementia," Ann Neurol. 55(2):164-73 (2004).
Abuqayyas et al., "Investigation of the Role of Fc-gamma-R and FcRn in mAb distribution to the brain," Mol Pharm. 10(5):1505-13 (2013) (9 pages).
Andersen et al., "Anti-carcinoembryonic antigen single-chain variable fragment antibody variants bind mouse and human neonatal Fc receptor with different affinities that reveal distinct cross-species differences in serum half-life," J Biol Chem. 287(27):22927-37 (2012).
Baker et al., "Neonatal Fc receptor for IgG (FcRn) regulates cross-presentation of IgG immune complexes by CD8-CD11b+ dendritic cells," Proc Natl Acad Sci U S A. 108(24):9927-32 (2011).
Beale et al., "Some observations on conserved polar side chains in immunoglobulin V-domains," Int J Biochem. 21(2):227-32 (1989).
Boswell et al., "Effects of charge on antibody tissue distribution and pharmacokinetics," Bioconjug Chem. 21(12):2153-63 (2010).
Bruno et al., "Population pharmacokinetics of trastuzumab in patients with HER2+ metastatic breast cancer," Cancer Chemother Pharmacol. 56(4):361-9 (2005).
Chen et al., "Evaluation of a catenary PBPK model for predicting the in vivo disposition of mAbs engineered for high-affinity binding to FcRn," AAPS J. 14(4):850-9 (2012) (10 pages).
Chen et al., "Modulating antibody pharmacokinetics using hydrophilic polymers," Expert Opin Drug Deliv. 8(9):1221-36 (2011).
Chothia et al., "Canonical structures for the hypervariable regions of immunoglobulins," J Mol Biol. 196(4):901-17 (1987).
Dall'Acqua et al., "Increasing the affinity of a human IgG1 for the neonatal Fc receptor: biological consequences," J Immunol. 169:5171-80 (2002).
Dall'Acqua et al., "Properties of human IgG1s engineered for enhanced binding to the neonatal Fc receptor (FcRn)," J Biol Chem. 281(33):23514-24 (2006).
Datta-Mannan et al., "Humanized IgG1 variants with differential binding properties to the neonatal Fc receptor: relationship to pharmacokinetics in mice and primates," Drug Metab Dispos. 35(1):86-94 (2007).
Datta-Mannan et al., "Monoclonal antibody clearance. Impact of modulating the interaction of IgG with the neonatal Fc receptor," J Biol Chem. 282(3):1709-17 (2007).
Deane et al., "IgG-assisted age-dependent clearance of Alzheimer's amyloid beta peptide by the blood-brain barrier neonatal Fc receptor," J Neurosci. 25(50):11495-503 (2005).
Deng et al., "Monoclonal antibodies: what are the pharmacokinetic and pharmacodynamic considerations for drug development?" Expert Opin Drug Metab Toxicol. 8(2):141-60 (2012).
Deng et al., "Subcutaneous bioavailability of therapeutic antibodies as a function of FcRn binding affinity in mice," MAbs 4(1):101-9 (2012).
Dickinson et al., "Bidirectional FcRn-dependent IgG transport in a polarized human intestinal epithelial cell line," J Clin Invest. 104(7):903-11 (1999).
Firan et al., "The MHC class I-related receptor, FcRn, plays an essential role in the maternofetal transfer of gamma-globulin in humans," Int Immunol. 13(8):993-1002 (2001).
Garber et al., "A broad range of Fab stabilities within a host of therapeutic IgGs," Biochem Biophys Res Commun. 355(3):751-7 (2007).
Garg et al., "Investigation of the influence of FcRn on the distribution of IgG to the brain," AAPS J. 11(3):553-7 (2009).
Ghetie et al., "Increasing the serum persistence of an IgG fragment by random mutagenesis," Nat Biotech. 15:637-40 (1997).
Ghetie et al., "Transcytosis and catabolism of antibody," Immunol Res. 25(2):97-113 (2002).
Gurbaxani et al., "Development of new models for the analysis of Fc-FcRn interactions," Mol Immunol. 43(9):1379-89 (2006).
Gurbaxani et al.,"Analysis of a family of antibodies with different half-lives in mice fails to find a correlation between affinity for FcRn and serum half-life," Mol Immunol. 43(9):1462-73 (2006).
Gurbaxani, "Mathematical modeling as accounting: predicting the fate of serum proteins and therapeutic monoclonal antibodies," Clin Immunol. 122(2):121-4 (2007).
Haraya et al., "Application of human FcRn transgenic mice as a pharmacokinetic screening tool of monoclonal antibody," Xenobiotica. 44(12):1127-34 (2014).
Hinton et al., "An engineered human IgG1 antibody with longer serum half-life," J Immunol. 176(1):346-56 (2006).
Hinton et al., "Engineered human IgG antibodies with longer serum half-lives in primates," J Biol Chem. 279(8):6213-6 (2004).
Hugo et al., "Functional aspects of co-variant surface charges in an antibody fragment," Protein Sci. 11(11):2697-05 (2002).

(56) References Cited

OTHER PUBLICATIONS

Igawa et al., "Engineering the variable region of therapeutic IgG antibodies," MAbs. 3(3):243-52 (2011).
Igawa et al., "Reduced elimination of IgG antibodies by engineering the variable region," Protein Eng Des Sel. 23(5):385-92 (2010).
Jefferis, "Aggregation, immune complexes and immunogenicity," MAbs. 3(6):503-4 (2011).
Jefferis, "Isotype and glycoform selection for antibody therapeutics," Arch Biochem Biophys. 526(2):159-66 (2012).
Johnson et al., "Human antibody engineering," Curr Opin Struct Biol. 3:564-71 (1993).
Joubert et al., "Highly aggregated antibody therapeutics can enhance the in vitro innate and late-stage T-cell immune responses," J Biol Chem. 287(30):25266-79 (2012) (25 pages).
Kacskovics et al., "Recent advances using FcRn overexpression in transgenic animals to overcome impediments of standard antibody technologies to improve the generation of specific antibodies," MAbs. 3(5):431-439 (2011).
Kaneko et al., "Optimizing therapeutic antibody function: progress with Fc domain engineering," BioDrugs. 25(1):1-11 (2011).
Khawli et al.,"Charge variants in IgG1: Isolation, characterization, in vitro binding properties and pharmacokinetics in rats," MAbs. 2(6):613-24 (2010).
Kim et al., "Mapping the site on human IgG for binding of the MHC class I-related receptor, FcRn," Eur J Immunol. 29(9):2819-25 (1999).
Kontermann, "Strategies for extended serum half-life of protein therapeutics," Curr Opin Biotechnol. 22:1-9 (2011).
Kontermann, "Strategies to extend plasma half-lives of recombinant antibodies," BioDrugs. 23(2):93-109 (2009).
Kubota et al., "Engineered therapeutic antibodies with improved effector functions," Cancer Sci. 100(9):1566-72 (2009).
Kunik et al., "Structural consensus among antibodies defines the antigen binding site," PLoS Comput Biol. 8(2):e1002388 (2012) (12 pages).
Kuo et al., "Neonatal Fc receptor and IgG-based therapeutics," MAbs. 3(5):422-30 (2011).
Kuo et al., "Neonatal Fc receptor: from immunity to therapeutics," J Clin Immunol. 30(6):777-789 (2010).
Liu et al., "Engineering therapeutic monoclonal antibodies," Immunol Rev. 222:9-27 (2008).
Lobo et al., "Antibody pharmacokinetics and pharmacodynamics," J Pharm Sci. 93(11):2645-68 (2004).
Martin et al., "Characterization of the 2:1 complex between the class I MHC-related Fc receptor and its Fc ligand in solution," Biochem. 38(39):12639-47 (1999).
Martin et al., "Crystal structure at 2.8 A of an FcRn/heterodimeric Fc complex: mechanism of pH-dependent binding," Mol Cell. 7(4):867-77 (2001).
Medesan et al., "Delineation of the amino acid residues involved in transcytosis and catabolism of mouse IgG1," J Immunol. 158(5):2212-7 (1997).
Morea et al., "Antibody modeling: implications for engineering and design," Methods. 20(3):267-79 (2000).
Mould et al., "Pharmacokinetics and pharmacodynamics of monoclonal antibodies: concepts and lessons for drug development," BioDrugs. 24(1):23-39 (2010).
Mould et al., "The pharmacokinetics and pharmacodynamics of monoclonal antibodies—mechanistic modeling applied to drug development," Curr Opin Drug Discov Devel. 10(1):84-96 (2007).
Ober et al., "Differences in promiscuity for antibody-FcRn interactions across species: implications for therapeutic antibodies," Int Immunol. 13(12):1551-9 (2001).
Oganesyan et al., "Structural characterization of a human Fc fragment engineered for extended serum half-life," Mol Immunol. 46(8-9):1750-5 (2009).
Onda et al., "Lowering the isoelectric point of the Fv portion of recombinant immunotoxins leads to decreased nonspecific animal toxicity without affecting antitumor activity," Cancer Res. 61(13):5070-7 (2001).
Ostrowitzki et al., "Mechanism of amyloid removal in patients with Alzheimer disease treated with gantenerumab," Arch Neurol. 69(2):198-207 (2012).
Pavlinkova et al., "Charge-modified single chain antibody constructs of monoclonal antibody CC49: generation, characterization, pharmacokinetics, and biodistribution analysis," Nucl Med Biol. 26(1):27-34 (1999).
Perchiacca et al., "Structure-based design of conformation- and sequence-specific antibodies against amyloid beta," Proc Natl Acad Sci U S A. 109(1):84-9 (2012).
Petkova et al., "Enhanced half-life of genetically engineered human IgG1 antibodies in a humanized FcRn mouse model: potential application in humorally mediated autoimmune disease," Int Immunol. 18(12):1759-69 (2006).
Presta, "Molecular engineering and design of therapeutic antibodies," Curr Opin Immunol. 20(4):460-70 (2008).
Qiao et al., "Dependence of antibody-mediated presentation of antigen on FcRn," Proc Natl Acad Sci U S A. 105(27):9337-42 (2008).
Robert et al., "Restricted V gene usage and VH/VL pairing of mouse humoral response against the N-terminal immunodominant epitope of the amyloid beta peptide," available in PMC Feb. 15, 2011, published in final edited form as: Mol Immunol. 48(1-3):59-72 (2010) (25 pages).
Roopenian et al., "FcRn: the neonatal Fc receptor comes of age," Nat Rev Immunol. 7(9):715-25 (2007).
Roopenian et al., "Human FcRn transgenic mice for pharmacokinetic evaluation of therapeutic antibodies," Methods Mol Biol. 602:93-104 (2010).
Schoch et al., "Charge-mediated influence of the antibody variable domain on FcRn-dependent pharmacokinetics," Proc Natl Acad Sci U S A. 112(19):5997-6002 (2015).
Schoch, Angela, Doctoral dissertation: "Influence of the Antibody Variable Domain on FcRn-Dependent Pharmacokinetics," Ludwig-Maximilians-Universitat, 2014.
Schreier et al., "Multiple differences between the nucleic acid sequences of the IgG2aa and IgG2ab alleles of the mouse," Proc Natl Acad Sci U S A. 78(7):4495-9 (1981) (6 pages).
Seldon et al., "Improved Protein-A separation of V(H)3 Fab from Fc after papain digestion of antibodies," J Biomol Tech. 22(2):50-2 (2011).
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem. 276(9):6591-604 (2001).
Sircar et al., "RosettaAntibody: antibody variable region homology modeling server," Nucleic Acids Res. 37(Web Server issue):W474-9 (2009).
Sivasubramanian et al., "Toward high-resolution homology modeling of antibody Fv regions and application to antibody-antigen docking," Proteins. 74(2):497-514 (2009).
Spiegelberg et al., "The Catabolism of Homologous and Heterologous 7S Gamma Globulin Fragments," J Exp Med. 121:323-38 (1965).
Suzuki et al., "Importance of neonatal FcR in regulating the serum half-life of therapeutic proteins containing the Fc domain of human IgG1: a comparative study of the affinity of monoclonal antibodies and Fc-fusion proteins to human neonatal FcR," J Immunol. 184(4):1968-76 (2010).
Tabrizi et al., "Biodistribution mechanisms of therapeutic monoclonal antibodies in health and disease," AAPS J. 12(1):33-43 (2010).
Tabrizi et al., "Elimination mechanisms of therapeutic monoclonal antibodies," Drug Discov Today. 11(1-2):81-8 (2006).
Tabrizi et al., "Preclinical and clinical safety of monoclonal antibodies," Drug Discov Today. 12(13-14):540-7 (2007).
Therapeutic Monoclonal Antibodies: From Bench to Clinic. An, 924 pages (2009).
Vugmeyster et al., "Complex pharmacokinetics of a humanized antibody against human amyloid beta peptide, anti-abeta Ab2, in nonclinical species," Pharm Res. 28(7):1696-706 (2011).

(56) References Cited

OTHER PUBLICATIONS

Vugmeyster et al., "Pharmacokinetics and toxicology of therapeutic proteins: Advances and challenges," World J Biol Chem. 3(4):73-92 (2012).
Wang et al., "Monoclonal antibodies with identical Fc sequences can bind to FcRn differentially with pharmacokinetic consequences," Drug Metab Dispos. 39(9):1469-77 (2011).
Wang et al., "Monoclonal antibody pharmacokinetics and pharmacodynamics," Clin Pharmacol Ther. 84(5):548-558 (2008).
Wang et al., "Rapid antibody responses by low-dose, single-step, dendritic cell-targeted immunization," Proc Natl Acad Sci. 96(2):847-52 (2000).
Weidenhaupt et al., "Functional mapping of conserved, surface exposed charges of antibody variable domains," J Mol Recognit. 15(2):94-103 (2002).
Wentao et al., "Targeting the neonatal fc receptor for antigen delivery using engineered fc fragments," available in PMC Dec. 1, 2009, published in final edited form as: J Immunol. 181(11):7550-61 (2008).
Wilcock et al., "Deglycosylated anti-amyloid-beta antibodies eliminate cognitive deficits and reduce parenchymal amyloid with minimal vascular consequences in aged amyloid precursor protein transgenic mice," J Neurosci. 26(20):5340-6 (2006).
Wu et al., "Structure-based engineering of a monoclonal antibody for improved solubility," Protein Engin Des Sel. 23(8):643-51 (2010).
Yamada, "Therapeutic monoclonal antibodies," Keio J Med. 60(2):37-46 (2011).
Yeung et al., "Engineering human IgG1 affinity to human neonatal Fc receptor: impact of affinity improvement on pharmacokinetics in primates," J Immunol. 182(12):7663-71 (2009).
Zalevsky et al., "Enhanced antibody half-life improves in vivo activity," Nat Biotechnol. 28(2):157-159 (2010).
Zhu et al., "Protein pI shifts due to posttranslational modifications in the separation and characterization of proteins," Anal Chem. 77(9):2745-55 (2005).
Official Report for Australian Patent Application No. 2005254928, dated Oct. 4, 2010 (4 pages).
Response to Official Report for Australian Patent Application No. 2005254928, dated Oct. 4, 2010, filed Oct. 3, 2011 (24 pages).
Official Report for Australian Patent Application No. 2007200047, dated Dec. 5, 2008 (3 pages).
Response to Official Report for Australian Patent Application No. 2007200047, dated Dec. 5, 2008, filed Oct. 2, 2009 (7 pages).
Official Report for Australian Patent Application No. 2007227813, dated Sep. 23, 2011 (1 page).
Response to Official Report for Australian Patent Application No. 2007227813, dated Sep. 23, 2011, filed Sep. 10, 2012 (2 pages).
Office Action for Brazilian Patent Application No. PI0709050-1, dated Nov. 21, 2012 (4 pages).
Response to Office Action for Brazilian Patent Application No. PI0709050-1, filed Dec. 14, 2012 (2 pages).
Office Action for Canadian Patent Application No. 2,414,772, dated Sep. 10, 2009 (3 pages).
Response to Office Action for Canadian Patent Application No. 2,414,772, dated Sep. 10, 2009, filed Feb. 26, 2010 (6 pages).
Office Action for Canadian Patent Application 2,570,130, dated Nov. 3, 2011 (6 pages).
Response to Office Action for Canadian Patent Application No. 2,750,130, dated Nov. 3, 2011, filed May 3, 2012 (19 pages).
Office Action for Canadian Patent Application No. 2,570,130, dated Jan. 23, 2013 (5 pages).
Response to Office Action for Canadian Patent Application No. 2,570,130, dated Jan. 23, 2013, filed Jul. 23, 2013 (10 pages).
Office Action for Canadian Patent Application No. 2,630,344, dated Jul. 9, 2013 (5 pages).
Response to Office Action for Canadian Patent Application No. 2,630,344, dated Jul. 9, 2013, filed Jan. 9, 2014 (16 pages).
Office Action for Canadian Patent Application No. 2,570,130, dated Dec. 15, 2014 (3 pages).
Response to Office Action for Canadian Patent Application No. 2,570,130, dated Dec. 15, 2014, filed Mar. 18, 2015 (2 pages).
Notification of the First Office Action for Chinese Patent Application No. 200780009817.3, dated May 18, 2011 (7 pages).
Response to First Office Action for Chinese Patent Application No. 200780009817.3, dated May 18, 2011, filed Sep. 15, 2011 (11 pages).
Second Office Action for Chinese Patent Application No. 200780009817.3, dated Apr. 16, 2012 (6 pages).
Response to Second Office Action for Chinese Patent Application No. 200780009817.3, dated Apr. 16, 2012, filed Jun. 28, 2012 (8 pages).
Decision on Rejection for Chinese Patent Application No. 200780009817.3, dated Jul. 30, 2012 (9 pages).
Request for Reexamination for Chinese Patent Application No. 200780009817.3, filed Nov. 14, 2012 (14 pages).
English Summary of Official Decision for Egyptian Patent Application No. PCT 1570/2008, dated Jun. 14, 2009 (2 pages).
Official Decision for Egyptian Patent Application No. PCT 1570/2008, dated Sep. 25, 2012 (9 pages).
Response to Official Decision for Egyptian Patent Application No. PCT 1570/2008, filed Nov. 2012 (32 pages).
Official Decision for Egyptian Patent Application No. PCT 1570/2008, dated Apr. 28, 2013 (6 pages).
Official Decision for Egyptian Patent Application No. PCT 1570/2008, dated Aug. 19, 2015 (8 pages).
Report of Filing of Response to Official Decision for Egyptian Patent Application No. PCT 1570/2008, dated Oct. 27, 2015 (3 pages).
First Examination Report for Indian Patent Application No. 3968/DELNP/2008, dated Feb. 13, 2014 (2 pages).
Response to First Examination Report for Indian Patent Application No. 3968/DELNP/2008, dated Feb. 13, 2014, filed Jan. 16, 2015 (9 pages).
English Summary of Office Action for Israeli Patent Application No. 191331, dated Apr. 19, 2009 (3 pages).
Report of Filing Response to Office Action for Israeli Patent Application No. 191331, dated Apr. 5, 2009, filed Jul. 16, 2009 (3 pages).
English Summary of First Substantive Examination Report for Israeli Patent Application No. 191331, dated Jul. 26, 2010 (4 pages).
Report of Filing Response to First Substantive Examination Report for Israeli Patent Application No. 191331, dated Jan. 13, 2011 (7 pages).
English Summary of Further Substantive Examination Report for Israeli Patent Application No. 191331, dated Jan. 17, 2012 (3 pages).
Report of Filing Response to Further Substantive Examination Report for Israeli Patent Application No. 191331, filed dated Jul. 24, 2012 (6 pages).
English Summary of Further Substantive Examination Report for Israeli Patent Application No. 191331, dated Oct. 21, 2013 (4 pages).
Report of Filing Further Substantive Examination Report for Israeli Patent Application No. 191331, dated Mar. 30, 2014 (3 pages).
English Translation of Notice of Reasons for Rejection for Japanese Patent Application No. 2002-508368, dated Feb. 15, 2011 (5 pages).
Response to Notice of Reasons for Rejection for Japanese Patent Application No. 2002-508368, filed May 25, 2012 (13 pages).
English Translation of Final Notice of Reasons of Rejection for Japanese Patent Application No. 2002-508368, dated Jan. 17, 2012 (2 pages).
Response to Notice of Reasons for Rejection for Japanese Patent Application No. 2002-508368, filed Jun. 13, 2011 (13 pages).
English Translation of Notice of Reasons for Rejection for Japanese Patent Application No. 2009-501383, dated Sep. 13, 2011 (4 pages).
Response to Notice of Reasons for Rejection for Japanese Patent Application No. 2009-501383, filed Mar. 12, 2012 (18 pages).
Official Action for Japanese Patent Application No. 2009-501383, dated Apr. 3, 2012 (3 pages).
Response to Official Action for Japanese Patent Application No. 2009-501383, filed May 24, 2012 (151 pages).

(56) References Cited

OTHER PUBLICATIONS

Notice of Preliminary Rejection for Korean Patent Application No. 10-2008-7023261, mailed Nov. 14, 2013 (7 pages).
Response to Notice of Preliminary Rejection for Korean Patent Application No. 10-2008-7023261, filed Jan. 9, 2014 (18 pages).
Modified Substantive Examination Adverse Report for Malaysian Patent Application No. PI 20083703, mailed Aug. 15, 2011 (3 pages).
Response to Modified Substantive Examination Adverse Report for Malaysian Patent Application No. PI 20083703, dated Aug. 15, 2011, filed Oct. 3, 2011 (5 pages).
English Summary of Office Action for Mexican Patent Application No. MX/A/2008/012223, dated Sep. 23, 2010 (4 pages).
Response to Office Action for Mexican Patent Application No. MX/a/2008/012223, filed Oct. 25, 2010 (10 pages).
Examination Report for New Zealand Patent Application No. 567888, dated May 13, 2010 (3 pages).
Response to Examination Report for New Zealand Patent Application No. 567888, dated May 13, 2010, filed Jul. 7, 2010 (8 pages).
Substantive Examination Report for Filipino Patent Application No. 12008502135, dated Oct. 2011 (2 pages).
Response to Substantive Examination Report for Filipino Patent Application No. 1-2008-502135, dated Oct. 28, 2011, filed Dec. 27, 2011 (1 page).
Office Action for Russian Patent Application No. 2008141905, dated Dec. 15, 2008 (3 pages).
Response to Official Action for Russian Patent Application No. 2008141905, filed Feb. 9, 2009 (9 pages).
Official Action for Russian Patent Application No. 2008141905, dated Nov. 18, 2010 (3 pages).
Response to Official Action for Russian Patent Application No. 2008141905, filed Jan. 11, 2011 (7 pages).
Examination Report for Singaporean Patent Application No. 200803655-0, mailed Jul. 29, 2010 (10 pages).
Response to Written Opinion for Singaporean Patent Application No. 200803655-0, filed Dec. 8, 2009 (118 pages).
English Translation of Office Action for Vietnamese Patent Application No. 1-2008-02591, dated Mar. 5, 2009 (1 page).
English Translation of Response to Examination Report for Vietnamese Patent Application No. 1-2008-02591, dated Mar. 5, 2009, filed Mar. 23, 2009 (1 page).
English Translation of Examination Report for Vietnamese Patent Application No. 1-2008-02591, dated Jun. 23, 2010 (1 page).
English Translation of Response to Examination Report for Vietnamese Patent Application No. 1-2008-02591, dated Jun. 23, 2010, filed Aug. 18, 2010 (2 pages).
English Translation of Office Action for Vietnamese Patent Application No. 1-2008-02591, dated Jan. 27, 2011 (2 pages).
Response to Examination Report for Vietnamese Patent Application No. 1-2008-02591, dated Jan. 27, 2011, filed Mar. 10, 2011 (1 page).
Communication for European Patent Application No. 01945896, dated Mar. 5, 2003 (2 pages).
Amended Claims for European Patent Application No. 01945896, filed Apr. 1, 2003 (3 pages).
Examination Report (Communication pursuant to Article 96(2) EPC) for European Patent Application No. 01945896, dated Sep. 30, 2005 (5 pages).
Response to Examination Report for European Patent Application No. 01945896, dated Sep. 30, 2005, filed Apr. 7, 2006 (7 pages).
Examination Report (Communication pursuant to Article 96(2) EPC) for European Patent Application No. 01945896, dated May 22, 2006 (4 pages).
Response to Examination Report for European Patent Application No. 01945896, dated May 22, 2006, filed Sep. 22, 2006 (13 pages).
Examination Report (Communication pursuant to Article 96(2) EPC) for European Patent Application No. 01945896, dated Apr. 24, 2007 (7 pages).
Response to Examination Report for European Patent Application No. 01945896, dated Apr. 24, 2007, filed Nov. 5, 2007 (9 pages).
Summons to Attend Oral Proceedings pursuant to Rule 115(1) EPC for European Patent Application No. 01945896, dated Jul. 25, 2008 (7 pages).
Submission in response to Summons to Attend Oral Proceedings for European Patent Application No. 01945896, dated Jul. 25, 2008, filed Oct. 10, 2008 (14 pages).
Consultation by telephone with the applicant/representative for European Patent Application No. 01945896, dated Nov. 5, 2008 (28 pages).
Result of Consultation for European Patent Application No. 01945896, dated Nov. 10, 2008 (3 pages).
Minutes of the Oral Proceedings for European Patent Application No. 01945896, dated Dec. 17, 2008 (7 pages).
Notice of Intent to Grant a European Patent and Annex (Reasons for Decision) for European Patent Application No. 01945896, dated Mar. 18, 2009 (10 pages).
Decision to Refuse a European Patent Application for European Patent Application No. 01945896, dated Sep. 11, 2009 (9 pages).
Notice of Appeal for European Patent Application No. 01945896, dated Nov. 3, 2009 (3 pages).
Appellant's Statement of Grounds of Appeal, including Requests, for European Patent Application No. 01945896, filed Jan. 14, 2010 (13 pages).
Commencement of Proceedings before the Board of Appeal for European Patent Application No. 01945896, dated Feb. 4, 2010 (3 pages).
Preliminary Opinion of the Board of Appeal for European Patent Application No. 01945896, dated Sep. 24, 2013 (9 pages).
Response to Summons to attend Oral Proceedings for European Patent Application No. 01945896, filed Sep. 30, 2013 (11 pages).
Third Party Observations for European Patent Application No. 01945896, dated Oct. 28, 2013 (3 pages).
Response to Preliminary Opinion of the Board of Appeal for European Patent Application No. 01945896, dated Sep. 24, 2013, filed Oct. 29, 2013 (4 pages).
Response to Communication of Third Party Observations for European Patent Application No. 01945896, dated Oct. 30, 2013, filed Nov. 6, 2013 (10 pages).
Decision of the Technical Board of Appeal and Minutes of the Oral Proceedings for European Patent Application No. 01945896, dated Nov. 12, 2013 (14 pages).
Communication for European Patent Application No. 01945896.7 including text intended for grant, dated Feb. 20, 2014 (30 pages).
Examination Report (Communication pursuant to Article 94(3) EPC) for European Patent Application No. 05753672, dated Jul. 6, 2009 (6 pages).
Response to Examination Report for European Patent Application No. 05753672, dated Jul. 6, 2009, filed Nov. 5, 2009 (7 pages).
Examination Report (Communication pursuant to Article 94(3) EPC) for European Patent Application No. 05753672, dated Jul. 8, 2010 (6 pages).
Response to Examination Report for European Patent Application No. 05753672, dated Jul. 8, 2010, filed Jan. 17, 2011 (13 pages).
Third Party Observations, including annexes, for European Patent Application No. 05753672, dated Jan. 16, 2012 (27 pages).
Examination Report (Communication pursuant to Article 94(3) EPC) for European Patent Application No. 05753672, dated Mar. 22, 2012 (5 pages).
Response to Examination Report, including annexes, for European Patent Application No. 05753672, dated Mar. 22, 2012 filed May 30, 2012 (20 pages).
Examination Report (Communication pursuant to Article 94(3) EPC) for European Patent Application No. 05753672, dated Aug. 21, 2013 (5 pages).
Response to Examination Report for European Patent Application No. 05753672, dated Aug. 21, 2013, filed Jan. 27, 2014 (20 pages).
Summons to Attend Oral Proceedings pursuant to Rule 115(1) EPC for European Patent Application No. 05753672, dated Mar. 6, 2014 (10 pages).
Third Party Observations for European Patent Application No. 05753672, dated Mar. 14, 2014 (4 pages).

(56) References Cited

OTHER PUBLICATIONS

Response to Summons to Attend Oral Proceedings for European Patent Application No. 05753672, dated Mar. 6, 2014, filed Jun. 3, 2014 (24 pages).
Third Party Observations for European Patent Application No. 05753672, dated Jul. 9, 2014 (6 pages).
Results of Consultation for European Patent Application No. 05753672, dated Jul. 24, 2014 (5 pages).
Response to Results of Consultations for European Patent Application No. 05753672, dated Jul. 24, 2014, filed Aug. 1, 2014 (9 pages).
Notice of Opposition for European Patent Application No. 05753672, dated Feb. 5, 2016 (39 pages).
Stine et al., "In vitro characterization of conditions for amyloid-beta peptide oligomerization and fibrillogenesis" J Biol Chem. 278(13):11612-22 (2003).
LeVine, "Alzheimer's beta-peptide oligomer formation at physiologic concentrations," Anal Biochem. 335(1):81-90 (2004).
Sehlin et al., "Heavy-chain complementarity-determining regions determine conformation selectivity of anti-A-beta antibodies," Neurodegener Dis. 8(3):117-23 (2011).
Janson et al., Protein Purification: Principles, High Resolution Methods, and Applications. John Wiley & Sons Australia Ltd, pp. 8, 85-86 (1989) (4 pages).
LeVine et al., "Alzheimer's Beta-peptide oligomer formation at physiologic concentrations," FASEB Summer Research Conferences: Protein Misfolding, Amyloid and Conformational Disease, Jun. 12-17, Snowmass, Co. Poster 18 (2 pages). 2004.
Extended European Search Report for European Patent Application No. 07747965, dated May 13, 2009 (11 pages).
Response to Examination Report for European Patent Application No. 07747965, dated Sep. 8, 2009, filed Sep. 11, 2009 (17 pages).
Examination Report (Communication pursuant to Article 94(3) EPC) for European Patent Application No. 07747965, dated Nov. 17, 2009 (4 pages).
Response to Examination Report for European Patent Application No. 07747965, dated Nov. 17, 2009, filed Jan. 29, 2010 (7 pages).
Supplemental Response for European Patent Application No. 07747965, filed Mar. 12, 2010 (5 pages).
Examination Report (Invitation Pursuant to Article 94(3) and Rule 71(1) EPC) for European Patent Application No. 07747965, dated Mar. 26, 2010 (3 pages).
Response to Examination Report for European Patent Application No. 07747965, dated Mar. 26, 2010, filed Apr. 15, 2010 (6 pages).
Notice of Opposition to a European Patent for European Patent Application No. 07747965, dated Sep. 22, 2011 (15 pages).
Communication of Notice of Opposition for European Patent Application No. 07747965, dated Oct. 13, 2011 (1 page).
Proprietor's Response to Notice of Opposition for European Patent Application No. 07747965, filed Feb. 24, 2012 (10 pages).
Summons to Oral Proceedings for European Patent Application No. 07747965, dated Dec. 5, 2012 (29 pages).
Proprietor's Response to Summons to Oral Proceedings for European Patent Application No. 07747965, dated Dec. 5, 2012, filed Feb. 22, 2013 (32 pages).
Opponent's Response to Summons to Oral Proceedings for European Patent Application No. 07747965, dated Dec. 5, 2012, filed Feb. 22, 2013 (23 pages).
Submission in advance of Oral Proceedings for European Patent Application No. 07747965, filed Apr. 10, 2013 (7 pages).
Minutes of Oral Proceedings before the Opposition Division and annexes thereto for European Patent Application No. 07747965, dated Apr. 23, 2013 (20 pages).
Decision of the Opposition Division for European Patent Application No. 07747965, dated Jul. 1, 2013 (39 pages).
International Search Report and Written Opinion for International Application No. PCT/EP2015/065633, mailed Feb. 24, 2016 (21 pages).
Sampei et al., "Identification and multidimensional optimization of an asymmetric bispecific IgG antibody mimicking the function of factor VIII cofactor activity," PLoS One. 8(2):e57479 (13 pages). 2013.
Affinity comparison of antibody according to EP2004688 and the antibodies of D2, dated Apr. 10, 2013 (1 page).
Chen et al., "A generic approach for absolute quantitation of the monoclonal antibody BAN2401 in human serum using immunocapture and mass spectrometric detection," Applied Pharmaceutical Analysis, Baltimore, Maryland (Sep. 17, 2012) (10 pages).
Curriculum Vitae of Pär Gellerfors, dated Apr. 10, 2013 (2 pages).
Curriculum Vitae of William F. Goure, Ph.D., dated Feb. 22, 2013 (3 pages).
Hearing Notice for Indian Patent Application No. 3968/DELNP/2008, dated Jul. 22, 2016 (2 pages).
Observations of the Proprietor for European Patent No. 1781703, filed Jul. 6, 2016 (31 pages).
Non-final Office Action for U.S. Appl. No. 14/627,161, mailed Jul. 19, 2016 (8 pages).
Response to Restriction Requirement for U.S. Appl. No. 14/627,161, filed May 17, 2016 (1 page).
Restriction Requirement for U.S. Appl. No. 14/627,161, mailed Mar. 17, 2016 (7 pages).
Satlin, "Clinical Studies with BAN2401: an Abeta Protofibril Specific Humanized Antibody," Mar. 12, 2011 (16 pages).

\* cited by examiner

Figure 8.

Amino acid sequences

```
SEQ ID NO 1:  SFGMH
SEQ ID NO 2:  YISSGSSTIY YGDTVKG
SEQ ID NO 3:  EGGYYYGRSY YTMDY
SEQ ID NO 4:  RSSQSIVHSN GNTYLE
SEQ ID NO 5:  KVSNRFS
SEQ ID NO 6:  FQGSHVPPT
SEQ ID NO 7:  DVVMTQSPLS LPVTPGAPAS ISCRSSQSIV HSNGNTYLEW YLQKPGQSPK LLIYKVSNRF
              SGVPDRFSGS GSGTDFTLRI SRVEAEDVGI YYCFQGSHVP PTFGPGTKLE IK
SEQ ID NO 8:  DVVMTQSPLS LPY₁TPGX₁PAS Y₂SCRSSQSIV HSNGNTYLEW YLQKPGQSPK LLIYKVSNRF
              SGVPDRFSGS GSGTDFTLX₂I Y₃X₃VY₄AEDVGI YYCFQGSHVP PTFGPGTKLE IK
SEQ ID NO 9:  DVVMTQSPLS LPVTPGDPAS VSCRSSQSIV HSNGNTYLEW YLQKPGQSPK LLIYKVSNRF
              SGVPDRFSGS GSGTDFTLTI QRVEAEDVGI YYCFQGSHVP PTFGPGTKLE IK
SEQ ID NO 10: DVVMTQSPLS LPVTPGDPAS VSCRSSQSIV HSNGNTYLEW YLQKPGQSPK LLIYKVSNRF
              SGVPDRFSGS GSGTDFTLTI SRVDAEDVGI YYCFQGSHVP PTFGPGTKLE IK
SEQ ID NO 11: DVVMTQSPLS LPATPGDPAS ISCRSSQSIV HSNGNTYLEW YLQKPGQSPK LLIYKVSNRF
              SGVPDRFSGS GSGTDFTLTI QRVEAEDVGI YYCFQGSHVP PTFGPGTKLE IK
SEQ ID NO 12: DVVMTQSPLS LPATPGDPAS ISCRSSQSIV HSNGNTYLEW YLQKPGQSPK LLIYKVSNRF
              SGVPDRFSGS GSGTDFTLTI SRVDAEDVGI YYCFQGSHVP PTFGPGTKLE IK
SEQ ID NO 13: EVQLVESGGG LVQPGGSLRL SCSASGFTFS SFGMHWVRQA PGKGLEWVAY ISSGSSTIYY
              GDTVKGRFTI SRDNAKNSLF LQMSSLRAED TAVYYCAREG GYYYGRSYYT MDYWGQGTTV TVSS
SEQ ID NO 14: EVQLVESGGG LVQPGGSLRL SCSASGFTFS SFGMHWZ₁Z₂QZ₃ PGKGLEWVAY ISSGSSTIYY
              GDTVKGRFTI SRDNAKNSLF LQMSSLRAED TAVYYCAREG GYYYGRSYYT MDYWGQGTTV TVSS
SEQ ID NO 15: EVQLVESGGG LVQPGGSLRL SCSASGFTFS SFGMHWVRQN PGKGLEWVAY ISSGSSTIYY
              GDTVKGRFTI SRDNAKNSLF LQMSSLRAED TAVYYCAREG GYYYGRSYYT MDYWGQGTTV TVSS
SEQ ID NO 16: EVQLVESGGG LVQPGGSLRL SCSASGFTFS SFGMHWVRQT PGKGLEWVAY ISSGSSTIYY
              GDTVKGRFTI SRDNAKNSLF LQMSSLRAED TAVYYCAREG GYYYGRSYYT MDYWGQGTTV TVSS
SEQ ID NO 17: EVQLVESGGG LVQPGGSLRL SCSASGFTFS SFGMHWVQQA PGKGLEWVAY ISSGSSTIYY
              GDTVKGRFTI SRDNAKNSLF LQMSSLRAED TAVYYCAREG GYYYGRSYYT MDYWGQGTTV TVSS
SEQ ID NO 18: EVQLVESGGG LVQPGGSLRL SCSASGFTFS SFGMHWIRQA PGKGLEWVAY ISSGSSTIYY
              GDTVKGRFTI SRDNAKNSLF LQMSSLRAED TAVYYCAREG GYYYGRSYYT MDYWGQGTTV TVSS
SEQ ID NO 19: DVVMTQSPLS LPVTPGDPAS ISCRSSQSIV HSNGNTYLEW YLQKPGQSPK LLIYKVSNRF
              SGVPDRFSGS GSGTDFTLRI SRVEAEDVGI YYCFQGSHVP PTFGPGTKLE IK
SEQ ID NO 20: DVVMTQSPLS LPVTPGDPAS ISCRSSQSIV HSNGNTYLEW YLQKPGQSPK LLIYKVSNRF
              SGVPDRFSGS GSGTDFTLTI SRVEAEDVGI YYCFQGSHVP PTFGPGTKLE IK
SEQ ID NO 21: DVVMTQSPLS LPVTPGDPAS ISCRSSQSIV HSNGNTYLEW YLQKPGQSPK LLIYKVSNRF
              SGVPDRFSGS GSGTDFTLTI SSVEAEDVGI YYCFQGSHVP PTFGPGTKLE IK
SEQ ID NO 22: DVVMTQSPLS LPVTPGDPAS ISCRSSQSIV HSNGNTYLEW YLQKPGQSPK LLIYKVSNRF
              SGVPDRFSGS GSGTDFTLRI SSVEAEDVGI YYCFQGSHVP PTFGPGTKLE IK
SEQ ID NO 23: ASTKGPSVFP LAPSSKSTSG GTAALGCLVK DYFPEPVTVS WNSGALTSGV HTFPAVLQSS
              GLYSLSSVVT VPSSSLGTQT YICNVNHKPS NTKVDKRVEP KSCDKTHTCP PCPAPELLGG
              PSVFLFPPKP KDTLMISRTP EVTCVVVDVS HEDPEVKFNW YVDGVEVHNA KTKPREEQYN
              STYRVVSVLT VLHQDWLNGK EYKCKVSNKA LPAPIEKTIS KAKGQPREPQ VYTLPPSREE
              MTKNQVSLTC LVKGFYPSDI AVEWESNGQP ENNYKTTPPV LDSDGSFFLY SKLTVDKSRW
              QQGNVFSCSV MHEALHNHYT QKSLSLSPGK
SEQ ID NO 24: RTVAAPSVFI FPPSDEQLKS GTASVVCLLN NFYPREAKVQ WKVDNALQSG NSQESVTEQD
              SKDSTYSLSS TLTLSKADYE KHKVYACEVT HQGLSSPVTK SFNRGEC
```

Figure 9. Light chains

| Kabat number | 1 | 2 | 3 | 4 | 5 | 6 | 7 | 8 | 9 | 1 0 | 1 | 2 | 3 | 4 | 5 | 6 | 7 | 8 | 9 | 2 0 | 1 | 2 | 3 | 4 | 5 | 6 | 7 | A | B | C | D | E | 8 | 9 | 3 0 | 1 | 2 | 3 | 4 | 5 | 6 | 7 | 8 | 9 | 4 0 | 1 | 2 | 3 | 4 | 5 | 6 | 7 | 8 | 9 | 5 0 | 1 | 2 | 3 | 4 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| N-terminal numbering | 1 | 2 | 3 | 4 | 5 | 6 | 7 | 8 | 9 | 1 0 | 1 | 2 | 3 | 4 | 5 | 6 | 7 | 8 | 9 | 2 0 | 1 | 2 | 3 | 4 | 5 | 6 | 7 | 8 | 9 | 3 0 | 1 | 2 | 3 | 4 | 5 | 6 | 7 | 8 | 9 | 4 0 | 1 | 2 | 3 | 4 | 5 | 6 | 7 | 8 | 9 | 5 0 | 1 | 2 | 3 | 4 | 5 | 6 | 7 | 8 | 9 |
| BAN2401 | D | V | V | M | T | Q | S | P | L | S | L | P | V | T | P | G | A | P | A | S | I | S | C | R | S | S | Q | S | I | V | H | S | N | G | N | T | Y | L | E | W | Y | L | Q | K | P | G | Q | S | P | K | L | L | I | Y | K | V | S | N | R |
| Abs according to the invention | D | V | V | M | T | Q | S | P | L | S | L | P | Y1 | T | P | G | X1 | P | A | S | Y2 | S | C | R | S | S | Q | S | I | V | H | S | N | G | N | T | Y | L | E | W | Y | Y | L | Q | K | P | G | Q | S | P | K | L | L | I | Y | K | V | S | N | R |
| i) | D | V | V | M | T | Q | S | P | L | S | L | P | V | T | P | G | D | P | A | S | V | S | C | R | S | S | Q | S | I | V | H | S | N | G | N | T | Y | L | E | W | Y | Y | L | Q | K | P | G | Q | S | P | K | L | L | I | Y | K | V | S | N | R |
| ii) | D | V | V | M | T | Q | S | P | L | S | L | P | V | T | P | G | D | P | A | S | V | S | C | R | S | S | Q | S | I | V | H | S | N | G | N | T | Y | L | E | W | Y | Y | L | Q | K | P | G | Q | S | P | K | L | L | I | Y | K | V | S | N | R |
| iii) | D | V | V | M | T | Q | S | P | L | S | L | P | V | T | P | G | D | P | A | S | I | S | C | R | S | S | Q | S | I | V | H | S | N | G | N | T | Y | L | E | W | Y | Y | L | Q | K | P | G | Q | S | P | K | L | L | I | Y | K | V | S | N | R |
| iv) | D | V | V | M | T | Q | S | P | L | S | L | P | A | T | P | G | D | P | A | S | I | S | C | R | S | S | Q | S | I | V | H | S | N | G | N | T | Y | L | E | W | Y | Y | L | Q | K | P | G | Q | S | P | K | L | L | I | Y | K | V | S | N | R |

Figure 9. Light chains continued.

| Kabat number | | | | | | | | | | | | | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | 5 | 6 | 7 | 8 | 9 | 6<br>0 | 1 | 2 | 3 | 4 | 5 | 6 | 7 | 8 | 9 | 7<br>0 | 1 | 2 | 3 | 4 | 5 | 6 | 7 | 8 | 9 | 8<br>0 | 1 | 2 | 3 | 4 | 5 | 6 | 7 | 8 | 9 | 9<br>0 | 1 | 2 | 3 | 4 | 5 | 6 | 7 | 8 | 9 | 10<br>0 | 1 | 2 | 3 | 4 | 5 | 6 | 7 |
| N-terminal numbering | 6 | | | | | | 7 | | | | | | | | | 8 | | | | | | | | | | 9 | | | | | | | | | | 10 | | | | | | | | | | 10 | | | | | | | |
| | | | | | | | | | | | | | | | | | | | | | | | | | | | | | | | | | | | | | | | | | | | | | | | | | | | 11 | | |
| BAN2401 | F | S | G | V | P | D | R | F | S | G | S | G | S | G | T | D | F | T | L | R | I | S | R | V | E | A | E | D | V | G | I | Y | Y | C | F | Q | G | S | H | V | P | P | T | F | G | P | G | T | K | L | E | I | K |
| Abs according to the invention | F | S | G | V | P | D | R | F | S | G | S | G | S | G | T | D | F | T | L | | | | X2 | | V3 | X3 | | V | | Y4 | | Y | Y | C | F | Q | G | S | H | V | P | P | T | F | G | P | G | T | K | L | E | I | K |
| i) | F | S | G | V | P | D | R | F | S | G | S | G | S | G | T | D | F | T | L | T | I | Q | R | V | E | A | E | D | V | G | I | Y | Y | C | F | Q | G | S | H | V | P | P | T | F | G | P | G | T | K | L | E | I | K |
| ii) | F | S | G | V | P | D | R | F | S | G | S | G | S | G | T | D | F | T | L | T | I | S | R | V | D | A | E | D | V | G | I | Y | Y | C | F | Q | G | S | H | V | P | P | T | F | G | P | G | T | K | L | E | I | K |
| iii) | F | S | G | V | P | D | R | F | S | G | S | G | S | G | T | D | F | T | L | T | I | Q | R | V | E | A | E | D | V | G | I | Y | Y | C | F | Q | G | S | H | V | P | P | T | F | G | P | G | T | K | L | E | I | K |
| iv) | F | S | G | V | P | D | R | F | S | G | S | G | S | G | T | D | F | T | L | T | I | S | R | V | D | A | E | D | V | G | I | Y | Y | C | F | Q | G | S | H | V | P | P | T | F | G | P | G | T | K | L | E | I | K |

Figure 10. Heavy chains.

| Kabat number | 1 2 3 4 5 6 7 8 9 | 1<br>0 1 2 3 4 5 6 7 8 9 | 2<br>0 1 2 3 4 5 6 7 8 9 | 3<br>0 1 2 3 4 5 6 7 8 9 | 4<br>0 1 2 3 4 5 6 7 8 9 | 5<br>0 1 2 3 4 5 6 7 8 9 |
|---|---|---|---|---|---|---|
| N-terminal numbering | 1 2 3 4 5 6 7 8 9 | 1<br>0 1 2 3 4 5 6 7 8 9 | 2<br>0 1 2 3 4 5 6 7 8 9 | 3<br>0 1 2 3 4 5 6 7 8 9 | 4<br>0 1 2 3 4 5 6 7 8 9 | 5<br>0 1 2 3 4 5 6 7 8 9 |
| BAN2401 | E V Q L V E S G | G G L V Q P G G | S L R L S C S A S | G F T F S S F G M H | W V R Q A P G K G L E W V A | Y I S S G S S T I Y |
| Abs according to the invention | E V Q L V E S G | G G L V Q P G G | S L R L S C S A S | G F T F S S F G M H | W 21 22 Q 23 P G K G L E W V A | Y I S S G S S T I Y |
| i) | E V Q L V E S G | G G L V Q P G G | S L R L S C S A S | G F T F S S F G M H | W V R Q N P G K G L E W V A | Y I S S G S S T I Y |
| ii) | E V Q L V E S G | G G L V Q P G G | S L R L S C S A S | G F T F S S F G M H | W V R Q T P G K G L E W V A | Y I S S G S S T I Y |
| iii) | E V Q L V E S G | G G L V Q P G G | S L R L S C S A S | G F T F S S F G M H | W V R Q Q P G K G L E W V A | Y I S S G S S T I Y |
| iv) | E V Q L V E S G | G G L V Q P G G | S L R L S C S A S | G F T F S S F G M H | W I R Q A P G K G L E W V A | Y I S S G S S T I Y |

Figure 10. Heavy chains continued.

| Kabat number | 6 | | | | | | | | | | | 7 | | | | | | | | | | | 8 | | | | | | | | | | | | | 9 | | | | | | | | | | | | | 10 | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | 9 | 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | A | B | C | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 | 0 | A | B | C | D | E | F |
| N-terminal numbering | 6 | | | | | | | | | | | 7 | | | | | | | | | | | 8 | | | | | | | | | | | | | 9 | | | | | | | | | | | | | 10 | | | | | | | | | | | 11 | | | | | |
| | 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 | 0 |
| BAN2401 | Y | G | D | T | V | K | G | R | F | T | I | S | R | D | N | A | K | N | S | L | F | L | Q | M | S | S | L | R | A | E | D | T | A | V | Y | Y | C | A | R | E | G | G | Y | Y | Y | G | R | S | Y | Y | Y | T | M | D | Y | | | | | | W | G | Q |
| Abs according to the invention | Y | G | D | T | V | K | G | R | F | T | I | S | R | D | N | A | K | N | S | L | F | L | Q | M | S | S | L | R | A | E | D | T | A | V | Y | Y | C | A | R | E | G | G | Y | Y | Y | G | R | S | Y | Y | Y | T | M | D | Y | | | | | | W | G | Q |
| i) | Y | G | D | T | V | K | G | R | F | T | I | S | R | D | N | A | K | N | S | L | F | L | Q | M | S | S | L | R | A | E | D | T | A | V | Y | Y | C | A | R | E | G | G | Y | Y | Y | G | R | S | Y | Y | Y | T | M | D | Y | | | | | | W | G | Q |
| ii) | Y | G | D | T | V | K | G | R | F | T | I | S | R | D | N | A | K | N | S | L | F | L | Q | M | S | S | L | R | A | E | D | T | A | V | Y | Y | C | A | R | E | G | G | Y | Y | Y | G | R | S | Y | Y | Y | T | M | D | Y | | | | | | W | G | Q |
| iii) | Y | G | D | T | V | K | G | R | F | T | I | S | R | D | N | A | K | N | S | L | F | L | Q | M | S | S | L | R | A | E | D | T | A | V | Y | Y | C | A | R | E | G | G | Y | Y | Y | G | R | S | Y | Y | Y | T | M | D | Y | | | | | | W | G | Q |
| iv) | Y | G | D | T | V | K | G | R | F | T | I | S | R | D | N | A | K | N | S | L | F | L | Q | M | S | S | L | R | A | E | D | T | A | V | Y | Y | C | A | R | E | G | G | Y | Y | Y | G | R | S | Y | Y | Y | T | M | D | Y | | | | | | W | G | Q |

Figure 10. Heavy chains continued.

| Kabat number | 6 | 7 | 8 | 9 | 11 0 | 1 | 2 | 3 |
|---|---|---|---|---|---|---|---|---|
| N-terminal numbering | 7 | 8 | 9 | 12 0 | 1 | 2 | 3 | 4 |
| BAN2401 | G | T | T | V | T | V | S | |
| Abs according to the invention | G | T | T | V | T | V | S | |
| i) | G | T | T | V | T | V | S | |
| ii) | G | T | T | V | T | V | S | |
| iii) | G | T | T | V | T | V | S | |
| iv) | G | T | T | V | T | V | S | |

Aβ PROTOFIBRIL BINDING ANTIBODIES

FIELD OF THE INVENTION

The present invention relates to the amyloid beta peptide (Aβ) and more specifically to antibodies that bind to Aβ protofibrils and their use in therapy and/or prophylactic treatment of Alzheimer's disease and other disorders associated with Aβ protein aggregation. Further the invention may relate to diagnosis of such diseases as well as monitoring of disease progression by use of the antibodies of the invention. Further, the invention may relate to veterinary use of the antibodies of the invention.

BACKGROUND OF THE INVENTION

Alzheimer's disease (AD) belongs to a group of neurodegenerative disorders and causes cognitive, memory and behavioral impairments. The hallmarks of Alzheimer's disease include extracellular amyloid plaques, intraneuronal neurofibrillary tangles, neuronal dysfunction and ultimately brain atrophy. The risk for developing AD increases with age and with increased number of persons reaching high age, a condition with increasing impact on the quality of life for elderly people. In addition the society faces a situation with accelerating costs.

In spite of the fact that the disease has been known for many years and several suggestions for treatment have been made, even today, there is no such efficient disease modifying therapy available today but only drugs which at best may provide symptomatic treatment. The mechanism behind the disease has been subject to a lot of studies. Briefly, Aβ for some reason starts to aggregate and via several intermediate forms, finally produces insoluble fibril/plaque deposits in the brain. It was early believed that the plaques, as such, affect the neurons and the signals transmitted by these, but today the results of the extensive studies indicate that soluble, aggregated, intermediate forms of Aβ most likely are a major cause of the disease and the symptoms observed in the patients.

One such intermediate form in the cascade of aggregated forms from Aβ monomers to insoluble Aβ fibrils is the soluble, high molecular weight Aβ protofibril, which was first described by Walsh in 1997 in The Journal of Biological Chemistry (Vol. 272(35) p. 22364-72). The importance of the Aβ protofibril for the development of AD was identified by the group of scientists headed by Lars Lannfelt, Uppsala University, in their studies of the Arctic mutation, which is an E693G mutation in the amyloid precursor protein (APP) causing increased formation of Aβ protofibrils. A family in northern Sweden carrying this mutation was found to develop severe Alzheimer's disease early in life and the finding of this combination provided the basic ideas for a new therapy. Accordingly, the Aβ protofibril was identified as strongly related to the disease and an important target for therapy. Based on their studies with Aβ peptides comprising the Arctic mutation, Lannfelt et al were able to produce Aβ protofibrils in vitro, Arctic as well as wild-type, in sufficient amounts for immunization and subsequent selection of antibodies with high affinity for Aβ protofibrils compared to other species in the Aβ system. Examples of methods for production of Aβ protofibrils and antibodies that bind to these are disclosed in WO02/03911 and WO2005/123775.

Of special importance was the development of the mouse monoclonal antibody mAb158, an antibody that binds to Aβ protofibrils, which is disclosed in EP2004688, which comprises the following CDR sequences:

VH-CDR1:
SEQ ID NO: 1
SFGMH

VH-CDR2:
SEQ ID NO: 2
YISSGSSTIYYGDTVKG

VH-CDR3:
SEQ ID NO: 3
EGGYYYGRSYYTMDY

VL-CDR1:
SEQ ID NO: 4
RSSQSIVHSNGNTYLE

VL-CDR2:
SEQ ID NO: 5
KVSNRFS

VL-CDR3:
SEQ ID NO: 6
FQGSHVPPT

The high affinity and selectivity of the humanized version of mAb158, BAN2401, makes it a very important candidate for use in therapy and/or prevention of Alzheimer's disease in particular, and it is presently subject to clinical trials in preparation for use as a pharmaceutical product. Characteristics of BAN2401 are described in EP2004688.

The efficacy of an antibody depends on several pharmacokinetic and pharmacodynamics factors, see e.g. Deng et al, Expert Opin. Drug Metab. Toxicol 8(2) (2012): p. 141-160; Boswell et al, Bioconjugate Chem. 21(2010): p. 2153-2163; Konterman, Current Opinion in Biotechnology 22 (2011): p. 1-9 and Igawa et al, mAbs 3:3 (2011): p. 243-252. Among these, extended serum half-life with increased systemic exposure often provides a considerable potential for improvements of significant therapeutic value. It also provides an opportunity for reduction of the dose which has systemic, important implications.

DESCRIPTION OF THE INVENTION

The present invention provides antibodies that bind to Aβ protofibrils and their use in therapy and/or prophylactic treatment of Alzheimer's disease and other disorders associated with Aβ protein aggregation. Further the invention may relate to antibodies useful in diagnosis of such diseases as well as their use in monitoring of disease progression of such diseases, as well as veterinary use of said antibodies. It has been identified that surprisingly the half-life as well as exposure of the humanized antibody based on mAb158, i.e. BAN2401, is considerably enhanced, e.g. about twice or more, primarily, by introducing one or more mutations in certain positions, i.e 17, 79 and/or 82, of the variable light chain of the BAN2401 antibody (Kabat positions 17, 74 and 77), respectively, see further FIG. 9 where these positions are referred to as $x_1$, $x_2$ and $x_3$. In BAN2401 the amino acid in position 17 (Kabat position 17) is A, the amino acid in position 79 (Kabat position 74) is R and the amino acid in position 82 (Kabat position 77) is R. The Kabat numbering is given in accordance with Kabat et al., Sequences of Proteins of Immunological Interest, 1991 (NIH Publications No. 91-3242).

Optionally, further improvements of an antibody according to the invention can be achieved by combining each of the mutations providing increased half-life with one or more neighboring mutations, i.e 13, 21, 81 and/or 84, of the variable light chain of the antibody (Kabat positions 13, 21, 76 and 79), respectively, see further FIG. 9 where these positions are referred to as referred to as $y_{1-4}$, 37, 38 and/or 40, of the variable Heavy chain of the antibody (Kabat positions 37, 38 and 40), respectively, see further FIG. 10 where these positions are referred to as referred to as $z_{1-3}$, for further improvements of immunological significance, i.e. low immunogenicity. When, compared to the BAN2401 sequence, $x_1$ is mutated the mutations $y_1$ and/or $y_2$ may be introduced and when $x_2$ and/or $x_3$ are mutated, the mutations $y_3$ and/or $y_4$ may be introduced. Further, the mutations $z_{1-3}$ may be introduced.

The present invention is as follows:

[1] An antibody or antigen binding fragment thereof having affinity against Aβ protofibrils, wherein the antibody or antigen binding fragment thereof has a variable light chain according to SEQ ID NO: 8, wherein
x1 is selected from A, D, E and Q, or a functional analogue thereof;
x2 is selected from R, T, K, A and G, or a functional analogue thereof;
x3 is selected from R, S, C, G and N, or a functional analogue thereof;
y1 is selected from V and A;
y2 is selected from I and V;
y3 is selected from S and Q;
y4 is selected from E and D; and optionally
a variable heavy chain according to SEQ ID NO: 14, wherein
z1 is selected from V and I;
z2 is selected from R and Q; and
z3 is selected from A, N and T.
with the exception for the combination x1=A, x2=R and x3=R.

[2] The antibody or antigen binding fragment according to [1], wherein
x1 is selected from A, D, E and Q;
x2 is selected from R, T, K, A and G;
x3 is selected from R, S, C, G and N;
y1 is selected from V and A;
y2 is selected from I and V;
y3 is selected from S and Q;
y4 is selected from E and D; and
a variable heavy chain according to SEQ ID NO: 14, wherein
z1 is selected from V and I;
z2 is selected from R and Q; and
z3 is selected from A, N and T;
with the exception for the combination x1=A, x2=R and x3=R.

[3] The antibody or antigen binding fragment according to [1] or [2], wherein the light chain a comprises a combination of mutations selected from:
x1 and (y1 and/or y2);
x1 and (y1 and/or y2) and x2 and (y3 and/or y4);
x1 and (y1 and/or y2) and x2 and x3 and (y3 and/or y4);
x1 and (y1 and/or y2) and x3 and (y3 and/or y4);
x2 (y3 and/or y4);
x2 and x3 and (y3 and/or y4); and
x3 and (y3 and/or y4);
with the exception for the combination x1=A, x2=R and x3=R.

[4] The antibody or antigen binding fragment according to any one of [1] to [3], wherein the variable light chain comprises one or more mutations, selected from:
x1 is D and (y1 and/or y2);
x1 is D and (y1 and/or y2), x2 is T and (y3 and/or y4);
x1 is D and (y1 and/or y2), x2 is T, x3 is S and (y3 and/or y4);
x1 is D and (y1 and/or y2) and x3 is S and (y3 and/or y4);
x2 is T (y3 and/or y4);
x2 is T and x3 is S and (y3 and/or y4); and
x3 is S and (y3 and/or y4);
wherein y1 is V or A and y2 is V or I, with exclusion of the combination y1=V and y2=I; y3 is S or Q and y4 is E or D with exclusion of the combination y3=S and Y4=E.

[5] The antibody or antigen binding fragment according to any one of [1] to [4], wherein
x1 is D;
x2 is T;
x3 is R;
y1 is selected from V and A;
y2 is selected from V and I;
y3 is selected from Q and S;
y4 is selected from D and E;
z1 is V;
z2 is R; and
z3 is selected from N, T and A;
with exclusion of the combination wherein y1 is V, y2 is I, y3, is S, y4 is E, z1 is V, z2 is R and z3 is A.

[6] An antibody or antigen binding fragment thereof, according to [1], comprising a variable light chain comprising an amino acid sequence as set out in SEQ ID NO: 12; and a variable heavy chain comprising an amino acid sequence as set out in SEQ ID NO: 16.

[7] An antibody or antigen binding fragment thereof, according to [1], comprising a variable light chain comprising an amino acid sequence as set out in SEQ ID NO: 9; and a variable heavy chain comprising an amino acid sequence as set out in SEQ ID NO: 15.

[8] An antibody or antigen binding fragment thereof, according to [1], comprising a variable light chain comprising an amino acid sequence as set out in SEQ ID NO: 10; and a variable heavy chain comprising an amino acid sequence as set out in SEQ ID NO: 15.

[9] An antibody or antigen binding fragment thereof, according to [1], comprising a variable light chain comprising an amino acid sequence as set out in SEQ ID NO: 11; and a variable heavy chain comprising an amino acid sequence as set out in SEQ ID NO: 15.

[10] An antibody or antigen binding fragment thereof, according to [1], comprising a variable light chain comprising an amino acid sequence as set out in SEQ ID NO: 12; and a variable heavy chain comprising an amino acid sequence as set out in SEQ ID NO: 15.

[11] An antibody or antigen binding fragment thereof, according to [1], comprising a variable light chain comprising an amino acid sequence as set out in SEQ ID NO: 9; and a variable heavy chain comprising an amino acid sequence as set out in SEQ ID NO: 16.

[12] An antibody or antigen binding fragment thereof, according to [1], comprising a variable light chain comprising an amino acid sequence as set out in SEQ ID NO: 10; and a variable heavy chain comprising an amino acid sequence as set out in SEQ ID NO: 16.

[13] An antibody or antigen binding fragment thereof, according to [1], comprising a variable light chain comprising an amino acid sequence as set out in SEQ ID NO: 11; and a variable heavy chain comprising an amino acid sequence as set out in SEQ ID NO: 16.

[14] The antibody or antigen binding fragment according to any one of [1] to [13], wherein the antibody or the antigen binding fragment comprises an IgG heavy chain constant region.

[15] An antibody according to any one of [1] to [14], for use in therapy.

[16] An antibody according to any one of [1] to [14], for use in treatment and/or prophylaxis of Alzheimer's disease and other disorders associated with Aβ protein aggregation.

[17] An antibody according to [16], for use, wherein such other disorders associated with Aβ protein aggregation are selected from traumatic brain injury (TBI), Lewy body dementia (LBD), Downs syndrome (DS), Amyotrophic lateral sclerosis (ALS), Frontotemporal dementia, tauopathies, systemic amyloidoses, atherosclerosis and Parkinson's disease dementia (PDD).

[18] Use of an antibody according to any one of [1] to [14], in the manufacture of a medicament useful in the treatment and/or prophylaxis of Alzheimer's disease and other disorders associated with Aβ protein aggregation.

[19] The use according to [18], wherein such other disorders associated with Aβ protein aggregation are selected from Traumatic brain injury (TBI), Lewy body dementia (LBD), Downs syndrome (DS), Amyotrophic lateral sclerosis (ALS), Frontotemporal dementia, tauopathies, systemic amyloidoses, atherosclerosis and Parkinson's disease dementia (PDD).

[20] A method of reducing amount of Aβ protofibrils in a subject, comprising administering to said subject a therapeutically effective amount of the antibody or antigen binding fragment according to [1] to [14].

[21] A method for treatment and/or prophylaxis of Alzheimer's disease in a subject having, or being at risk of developing said disease, comprising administering to said subject a therapeutically effective amount of the antibody or antigen binding fragment according to [1] to [14].

[22] A method for treatment and/or prophylaxis of traumatic brain injury (TBI), Lewy body dementia (LBD), Down syndrome (DS), Amyotrophic lateral sclerosis (ALS), Frontotemporal dementia, tauopathies, systemic amyloidosis, atherosclerosis and Parkinson's disease dementia (PDD) in a subject having, or being at risk of developing said disease, comprising administering to said subject a therapeutically effective amount of the antibody or antigen binding fragment according to [1] to [14].

[23] A method for measuring amount of Aβ protofibrils and/or aggregated Aβ protein in a person, comprising contacting the person's tissue or body fluid, in vivo or in vitro, with the antibody or antigen binding fragment according to [1] to [14] and measuring the amount of antibody or antigen binding fragment bound to said Aβ protofibrils and/or aggregated Aβ protein.

[24] A method for diagnosis of Alzheimer's disease in persons having or at risk of developing the disease, comprising contacting the person's tissue or body fluid, in vivo or in vitro, with the antibody or antigen binding fragment according to [1] to [14], or a fragment thereof, and measuring the amount of said antibody bound to aggregated Aβ protein.

[25] A method for diagnosis of traumatic brain injury (TBI), Lewy body dementia (LBD), Down syndrome (DS), Amyotrophic lateral sclerosis (ALS), Frontotemporal dementia, tauopathies, systemic amyloidosis, atherosclerosis and Parkinson's disease dementia (PDD) in persons having or at risk of developing any of said diseases, comprising contacting the person's tissue or body fluid, in vivo or in vitro, with the antibody or antigen binding fragment according to [1] to [14], or a fragment thereof, and measuring the amount of said antibody bound to aggregated Aβ protein.

[26] A pharmaceutical composition comprising the antibody or antigen binding fragment according to any one of [1] to [14], together with pharmaceutically acceptable excipient and/or diluents.

[27] An antibody according to any one of [1] to [14], for veterinary use.

BRIEF DESCRIPTION OF THE DRAWINGS

FIG. 8 provides amino acid sequences in relation to the present invention.

FIG. 9 provides a table, split on two pages, with the amino acid sequence of the light variable chain with VL-CDR1-3 sequences in grey. BAN2401: SEQ ID NO: 7. Novel antibodies with light variable chain according to the invention: SEQ ID NO: 8. Specific examples of such variable light chains: i): SEQ ID NO: 9; ii): SEQ ID NO: 10; iii): SEQ ID NO: 11; and iv): SEQ ID NO: 12.

FIG. 10 provides a table, split on three pages, with the amino acid sequence of the heavy variable chain with the VH-CDR1-3 sequences in grey. BAN2401: SEQ ID NO: 13. Novel antibodies with heavy variable chain according to the invention SEQ ID NO: 14. Specific examples of such variable heavy chains: i): SEQ ID NO: 15; ii): SEQ ID NO: 16; iii): SEQ ID NO: 17; and iv): SEQ ID NO: 18.

Figure 1:
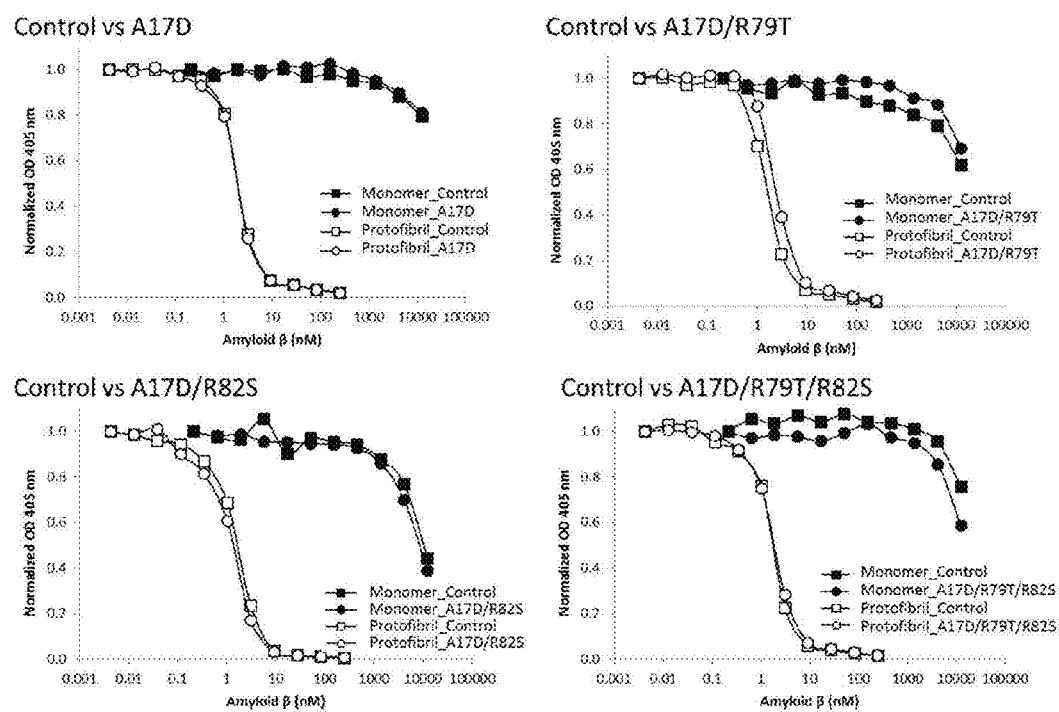
FIG. 1 provides analysis of binding and selectivity for Aβ protofibrils compared to Aβ monomers for A17D, A17D/R79T, A17D/R82S and A17D/R79T/R82S compared to BAN2401 (control). Binding inhibition by Aβ1-42 protofibrils in solution is shown by open circles and open squares and binding inhibition by Aβ1-40 monomers in solution are shown by closed circles and closed squares.

The mutations A17D, R79T and R82S, represent positions in the BAN2401 antibody, wherein amino acids in positions 17, 79 and 82 are mutated in the variable light chain.

With "BAN2401" is meant a humanized monoclonal antibody of the mouse antibody mAb158 comprising a variable light chain with an amino acid sequence as set out in SEQ ID NO: 7 and a variable heavy chain as set out in SEQ ID NO: 13. Both BAN2401 and mAb158 and their characteristics, including VL-CDR1-3 and VH-CDR1-3 are described in EP2004688. BAN2401 is excluded from the present invention.

With the following abbreviations is meant:

BAN2401: an antibody comprising a variable light chain comprising an amino acid sequence as set out in SEQ ID NO: 7; and a variable heavy chain comprising an amino acid sequence as set out in SEQ ID NO: 13.

A17D: an antibody comprising a variable light chain comprising an amino acid sequence as set out in SEQ ID NO: 19 and a variable heavy chain comprising an amino acid sequence as set out in SEQ ID NO: 13.

A17D/R79T: an antibody comprising a variable light chain comprising an amino acid sequence as set out in SEQ ID NO: 20 and a variable heavy chain comprising an amino acid sequence as set out in SEQ ID NO: 13.

A17D/R79T/R82S: an antibody comprising a variable light chain comprising an amino acid sequence as set out in SEQ ID NO: 21 and a variable heavy chain comprising an amino acid sequence as set out in SEQ ID NO: 13.

A17D/R82S: an antibody comprising a variable light chain comprising an amino acid sequence as set out in SEQ ID NO: 22 and a variable heavy chain comprising an amino acid sequence as set out in SEQ ID NO: 13.

A17D/R79T_DI 1: an antibody comprising a variable light chain comprising an amino acid sequence as set out in SEQ ID NO: 9; and a variable heavy chain comprising an amino acid sequence as set out in SEQ ID NO: 15.

A17D/R79T_DI 2: an antibody comprising a variable light chain comprising an amino acid sequence as set out in SEQ ID NO: 10; and a variable heavy chain comprising an amino acid sequence as set out in SEQ ID NO: 15.

A17D/R79T_DI 3: an antibody comprising a variable light chain comprising an amino acid sequence as set out in SEQ ID NO: 11; and a variable heavy chain comprising an amino acid sequence as set out in SEQ ID NO: 15.

A17D/R79T_DI 4: an antibody comprising a variable light chain comprising an amino acid sequence as set out in SEQ ID NO: 12; and a variable heavy chain comprising an amino acid sequence as set out in SEQ ID NO: 15.

A17D/R79T_DI 5: an antibody comprising a variable light chain comprising an amino acid sequence as set out in SEQ ID NO: 9; and a variable heavy chain comprising an amino acid sequence as set out in SEQ ID NO: 16.

A17D/R79T_DI 6: an antibody comprising a variable light chain comprising an amino acid sequence as set out in SEQ ID NO: 10; and a variable heavy chain comprising an amino acid sequence as set out in SEQ ID NO: 16.

A17D/R79T_DI 7: an antibody comprising a variable light chain comprising an amino acid sequence as set out in SEQ ID NO: 11; and a variable heavy chain comprising an amino acid sequence as set out in SEQ ID NO: 16.

A17D/R79T_DI 8: an antibody comprising a variable light chain comprising an amino acid sequence as set out in SEQ ID NO: 12; and a variable heavy chain comprising an amino acid sequence as set out in SEQ ID NO: 16.

An antibody, or an antigen binding fragment thereof, according to the present invention comprises, in the light variable chain, in position 17 (Kabat position 17) the amino acid A, D, E, Q or a functional analogue, in position 79 (Kabat position 74) amino acid R, T, K, A, G or a functional analogue and in position 82 (Kabat position 77) amino acid R, S, C, G, N or a functional analogue. A functional analogue is an amino acid providing a lower pI value of the antibody compared to A (position 17) resp. R (position 79 and 82) without negatively affecting the binding to the antigen.

The amino acid sequences in the present disclosure are represented as follows:
SEQ ID NO: 1: variable heavy chain VH-CDR1 of BAN2401.
SEQ ID NO: 2: variable heavy chain VH-CDR2 of BAN2401.
SEQ ID NO: 3: variable heavy chain VH-CDR3 of BAN2401.
SEQ ID NO: 4: variable light chain VL-CDR1 of BAN2401.
SEQ ID NO: 5: variable light chain VL-CDR2 of BAN2401.
SEQ ID NO: 6: variable light chain VL-CDR3 of BAN2401.
SEQ ID NO: 7: variable light chain of BAN2401.
SEQ ID NO: 8: generic variable light chain sequence in antibodies of the invention.
SEQ ID NO: 9: specific variable light chain sequence in antibodies of the invention.
SEQ ID NO: 10: specific variable light chain sequence in antibodies of the invention.
SEQ ID NO: 11: specific variable light chain sequence in antibodies of the invention.
SEQ ID NO: 12: specific variable light chain sequence in antibodies of the invention.
SEQ ID NO: 13: variable heavy chain of BAN2401.
SEQ ID NO: 14: generic variable heavy chain sequence in antibodies of the invention.
SEQ ID NO: 15: specific variable heavy chain sequence in antibodies of the invention.
SEQ ID NO: 16: specific variable heavy chain sequence in antibodies of the invention.
SEQ ID NO: 17: specific variable heavy chain sequence in antibodies of the invention.
SEQ ID NO: 18: specific variable heavy chain sequence in antibodies of the invention.
SEQ ID NO: 19: specific variable light chain sequence in antibodies of the invention.
SEQ ID NO: 20: specific variable light chain sequence in antibodies of the invention.
SEQ ID NO: 21: specific variable light chain sequence in antibodies of the invention.
SEQ ID NO: 22: specific variable light chain sequence in antibodies of the invention.
SEQ ID NO: 23: amino acid sequence of human IgG1 constant region comprised in antibodies of the invention.
SEQ ID NO: 24: amino acid sequence of human K chain constant region comprised in antibodies of the invention.

The variable light chain (SEQ ID NO: 7) of BAN2401 and the antibodies of the invention comprises the three CDR-sequences (VL-CDR1-3):

```
VL-CDR1:
                                    SEQ ID NO: 4
RSSQSIVHSNGNTYLE

VL-CDR2:
                                    SEQ ID NO: 5
KVSNRFS

VL-CDR3:
                                    SEQ ID NO: 6
FQGSHVPPT
``` and the variable heavy chain (SEQ ID NO: 13) of BAN2401 and the antibodies of the invention, comprises the three CDR-sequences (VH-CDR1-3):

```
VH-CDR1:
                                    SEQ ID NO: 1
SFGMH

VH-CDR2:
                                    SEQ ID NO: 2
YISSGSSTIYYGDTVKG

VH-CDR3:
                                    SEQ ID NO: 3
EGGYYYGRSYYTMDY
```

According to one aspect of the invention, antibodies binding to Aβ protofibrils are provided, having the following CDR sequence combinations:

```
VH-CDR1:
                                    SEQ ID NO: 1
SFGMH

VH-CDR2:
                                    SEQ ID NO: 2
YISSGSSTIYYGDTVKG

VH-CDR3:
                                    SEQ ID NO: 3
EGGYYYGRSYYTMDY

VL-CDR1:
                                    SEQ ID NO: 4
RSSQSIVHSNGNTYLE

VL-CDR2:
                                    SEQ ID NO: 5
KVSNRFS

VL-CDR3:
                                    SEQ ID NO: 6
FQGSHVPPT
``` and comprising the variable light chain with SEQ ID NO: 8, wherein $x_1$ is A, D, E, Q or a functional analogue, $x_2$ is R, T, K, A, G or a functional analogue and $x_3$ is R, S, C, G, N or a functional analogue, with the exception for the combination $x_1$=A, $x_2$=R and $x_3$=R.

A functional analogue is an amino acid providing a lower pI value of the antibody compared to A ($x_1$) resp. R ($x_2$ and $x_3$) without negatively affecting the binding to the antigen.

The variable heavy chain has the amino acid sequence presented in SEQ ID NO: 14, comprising the $z_1$, $z_2$ and $z_3$ in any combination and wherein
$z_1$ is selected from V and I;
$z_2$ is selected from R and Q; and
$z_3$ is selected from A, N and T;
with the exception for the combination $z_1$=V, $z_2$=R and $z_3$=A.

It should be pointed out that based on this teaching, the identification of a functional analogue to the specific amino acids defined above for each of the positions is easily done by a person skilled in the art, as methods for introducing an amino acid in a specific position in accordance with the present invention, as well as testing the resulting product, e.g. with regard to affinity for Aβ protofibrils and other characteristics of importance, are disclosed, see below.

Accordingly, in one aspect of the invention there is provided an antibody, or antigen binding fragment thereof having affinity against Aβ protofibrils, wherein the antibody, or antigen binding fragment thereof has a variable light chain according to SEQ ID NO: 8, wherein
$x_1$ is selected from A, D, E and Q, or a functional analogue thereof;
$x_2$ is selected from R, T, K, A and G, or a functional analogue thereof;
$x_3$ is selected from R, S, C, G and N, or a functional analogue thereof;
$y_1$ is selected from V and A;
$y_2$ is selected from I and V;
$y_3$ is selected from S and Q;
$y_4$ is selected from E and D; and optionally
a variable heavy chain according to SEQ ID NO: 14, wherein
$z_1$ is selected from V and I;
$z_2$ is selected from R and Q; and
$z_3$ is selected from A, N and T;
with the exception for the combination $x_1$=A, $x_2$=R and $x_3$=R.

In one embodiment of this aspect, there is provided an antibody or an antigen binding fragment thereof, wherein
$x_1$ is selected from A, D, E and Q;
$x_2$ is selected from R, T, K, A and G;
$x_3$ is selected from R, S, C, G and N;
$y_1$ is selected from V and A;
$y_2$ is selected from I and V;
$y_3$ is selected from S and Q;
$y_4$ is selected from E and D; and
a variable heavy chain according to SEQ ID NO: 14, wherein
$z_1$ is selected from V and I;
$z_2$ is selected from R and Q; and
$z_3$ is selected from A, N and T;
with the exception for the combination $x_1$=A, $x_2$=R and $x_3$=R.

In one embodiment of this aspect, there is provided an antibody, or an antigen binding fragment thereof, wherein the light chain comprises a combination of mutations selected from:
$x_1$ and ($y_1$ and/or $y_2$);
$x_1$ and ($y_1$ and/or $y_2$) and $x_2$ and ($y_3$ and/or $y_4$);
$x_1$ and ($y_1$ and/or $y_2$) and $x_2$ and $x_3$ and ($y_3$ and/or $y_4$);
$x_1$ and ($y_1$ and/or $y_2$) and $x_3$ and ($y_3$ and/or $y_4$);
$x_2$ ($y_3$ and/or $y_4$);
$x_2$ and $x_3$ and ($y_3$ and/or $y_4$); and
$x_3$ and ($y_3$ and/or $y_4$);
with the exception for the combination $x_1$=A, $x_2$=R and $x_3$=R.

In one embodiment of this aspect, there is provided an antibody, or an antigen binding fragment thereof, wherein the variable light chain comprises one or more mutations, selected from:
$x_1$ is D and ($y_1$ and/or $y_2$);
$x_1$ is D and ($y_1$ and/or $y_2$), $x_2$ is T and ($y_3$ and/or $y_4$);
$x_1$ is D and ($y_1$ and/or $y_2$), $x_2$ is T, $x_3$ is S and ($y_3$ and/or $y_4$);
$x_1$ is D and ($y_1$ and/or $y_2$) and $x_3$ is S and ($y_3$ and/or $y_4$);
$x_2$ is T ($y_3$ and/or $y_4$);
$x_2$ is T and $x_3$ is S and ($y_3$ and/or $y_4$); and
$x_3$ is S and ($y_3$ and/or $y_4$);

wherein $y_1$ is V or A and $y_2$ is V or I, with exclusion of the combination $y_1$=V and $y_2$=I; $y_3$ is S or Q and $y_4$ is E or D with exclusion of the combination $y_3$=S and $y_4$=E.

In one embodiment of this aspect, there is provided an antibody, or an antigen binding fragment thereof, wherein $y_1$ is A, $y_2$ is V, $y_3$ is Q and $y_4$ is D.

In one embodiment of this aspect, there is provided an antibody, or an antigen binding fragment thereof, wherein
$x_1$ is D;
$x_2$ is T;
$x_3$ is R;
$y_1$ is selected from V and A;
$y_2$ is selected from V and I;
$y_3$ is selected from Q and S;
$y_4$ is selected from D and E;
$z_1$ is V;
$z_2$ is R; and
$z_3$ is selected from N, T and A;
with exclusion of the combination wherein $y_1$ is V, $y_2$ is I, $y_3$, is S, $y_4$ is E, $z_1$ is V, $z_2$ is R and $z_3$ is A.

In one embodiment of this aspect, there is provided an antibody, or an antigen binding fragment thereof, wherein
$x_1$ is D;
$x_2$ is T;
$x_3$ is R;
$y_1$ is V;
$y_2$ is V;
$y_3$ is Q;
$y_4$ is E;
$z_1$ is V;
$z_2$ is R; and
$z_3$ is N.

In one embodiment of this aspect, there is provided an antibody, or an antigen binding fragment thereof, wherein
$x_1$ is D;
$x_2$ is T;
$x_3$ is R;
$y_1$ is V;
$y_2$ is V;
$y_3$ is S;
$y_4$ is D;
$z_1$ is V;
$z_2$ is R; and
$z_3$ is N.

In one embodiment of this aspect, there is provided an antibody, or an antigen binding fragment thereof, wherein
$x_1$ is D;
$x_2$ is T;
$x_3$ is R;
$y_1$ is A;
$y_2$ is I;
$y_3$ is Q;
$y_4$ is E;
$z_1$ is V;
$z_2$ is R; and
$z_3$ is N.

In one embodiment of this aspect, there is provided an antibody, or an antigen binding fragment thereof, wherein
$x_1$ is D;
$x_2$ is T;
$x_3$ is R;
$y_1$ is A;
$y_2$ is I;
$y_3$ is S;
$y_4$ is D;
$z_1$ is V;

$z_2$ is R; and
$z_3$ is N.

In one embodiment of this aspect, there is provided an antibody, or an antigen binding fragment thereof, wherein
$x_1$ is D;
$x_2$ is T;
$x_3$ is R;
$y_1$ is V;
$y_2$ is V;
$y_3$ is Q;
$y_4$ is E;
$z_1$ is V;
$z_2$ is R; and
$z_3$ is T.

In one embodiment of this aspect, there is provided an antibody, or an antigen binding fragment thereof, wherein
$x_1$ is D;
$x_2$ is T;
$x_3$ is R;
$y_1$ is V;
$y_2$ is V;
$y_3$ is S;
$y_4$ is D;
$z_1$ is V;
$z_2$ is R; and
$z_3$ is T.

In one embodiment of this aspect, there is provided an antibody or an antigen binding fragment thereof, wherein
$x_1$ is D;
$x_2$ is T;
$x_3$ is R;
$y_1$ is A;
$y_2$ is I;
$y_3$ is Q;
$y_4$ is E;
$z_1$ is V;
$z_2$ is R; and
$z_3$ is T.

In one aspect of this embodiment, there is provided an antibody, or an antigen binding fragment thereof, wherein
$x_1$ is D;
$x_2$ is T;
$x_3$ is R;
$y_1$ is A;
$y_2$ is I;
$y_3$ is S;
$y_4$ is D;
$z_1$ is V;
$z_2$ is R; and
$z_3$ is T.

According to one aspect of the invention, each mutation $x_1$-$x_3$ is combined with one or more additional mutations $y_1$-$y_4$:
when $x_1$ is not A, the mutations $y_1$ and/or $y_2$ are introduced;
when $x_2$ is not R and/or $x_3$ is not R, the mutations $y_3$ and/or $y_4$ are introduced; providing variable light chains comprising the following combinations of mutants compared to SEQ ID NO: 7:
$x_1$ and ($y_1$ and/or $y_2$); or
$x_1$ and ($y_1$ and/or $y_2$) and $x_2$ and ($y_3$ and/or $y_4$); or
$x_1$ and ($y_1$ and/or $y_2$) and $x_2$ and $x_3$ and ($y_3$ and/or $y_4$); or
$x_1$ and ($y_1$ and/or $y_2$) and $x_3$ and ($y_3$ and/or $y_4$); or
$x_2$ and ($y_3$ and/or $y_4$); or
$x_2$ and $x_3$ and ($y_3$ and/or $y_4$); or
$x_3$ and ($y_3$ and/or $y_4$);
wherein the parameters x and y are as defined above.

In one embodiment, the light chain (SEQ ID NO: 8) of an antibody, or an antigen binding fragment thereof according to the invention comprises only one or more of the mutations $x_1$-$x_3$ in the light variable chain (using N-terminal numbering): A17D ($x_1$), R79T ($x_2$) and R82S ($x_3$):
A17D; or
A17D and R79T; or
A17D and R79T and R82S; or
A17D and R82S; or
R79T; or
R79T and R82S; or
R82S;
wherein $y_1$ is V, $y_2$ is I, $y_3$ is S and $y_4$ is E (no changes compared to SEQ ID NO: 7).

According to a further embodiment, mutations $y_1$-$y_4$ are introduced providing any one of the following combinations:
A17D and ($y_1$ and/or $y_2$);
A17D and ($y_1$ and/or $y_2$) and R79T and ($y_3$ and/or $y_4$);
A17D and ($y_1$ and/or $y_2$) and R79T and R82S and ($y_3$ and/or $y_4$);
A17D and ($y_1$ and/or $y_2$) and R82S ($y_3$ and/or $y_4$);
R79T ($y_3$ and/or $y_4$);
R79T and R82S and ($y_3$ and/or $y_4$);
R82S and ($y_3$ and/or $y_4$);
wherein $y_1$ is V or A and $y_2$ is V or I, with exclusion of the combination $y_1$=V and $y_2$=I, y3 is S or Q and $y_4$ is E or D, with exclusion of the combination $y_3$=S and $Y_4$=E.

Further specific combinations are disclosed in SEQ ID NOS: 9-12.

The heavy, variable chain (VH) of antibodies according to the present invention has the amino acid sequence SEQ ID NO: 14, wherein $z_1$ is V or I, $z_2$ is R or Q and $z_3$ is A, N or T, e.g. SEQ ID NO: 15-18.

In one embodiment of this aspect, there is provided an antibody or an antigen binding fragment thereof, wherein the antibody or antigen binding fragment comprises a variable light chain selected from an amino acid sequence as set out in any one of SEQ ID NOS: 9-12.

In one embodiment of this aspect, there is provided an antibody, or an antigen binding fragment thereof, wherein the antibody or antigen binding fragment comprises a variable heavy chain selected from an amino acid sequence as set out in any one of SEQ ID NOS: 15-18.

In one embodiment of this aspect, there is provided an antibody, or an antigen binding fragment thereof, wherein the antibody or antigen binding fragment comprises a variable light chain selected from an amino acid sequence as set out in any one of SEQ ID NOS: 9-12; and a variable heavy chain selected from an amino acid sequence as set out in any one of SEQ ID NOS: 15-18.

In one embodiment of this aspect, there is provided an antibody, or an antigen binding fragment thereof, wherein the antibody or antigen binding fragment comprises a variable light chain comprising an amino acid sequence as set out in SEQ ID NO: 9; and a variable heavy chain comprising an amino acid sequence as set out in SEQ ID NO: 15.

In one embodiment of this aspect, there is provided an antibody or an antigen binding fragment thereof, wherein the antibody or antigen binding fragment comprises a variable light chain comprising an amino acid sequence as set out in SEQ ID NO: 10; and a variable heavy chain comprising an amino acid sequence as set out in SEQ ID NO: 15.

In one embodiment of this aspect, there is provided an antibody or an antigen binding fragment thereof, wherein the antibody or antigen binding fragment comprises a variable light chain comprising an amino acid sequence as set out in SEQ ID NO: 11; and a variable heavy chain comprising an amino acid sequence as set out in SEQ ID NO: 15.

In one embodiment of this aspect, there is provided an antibody or an antigen binding fragment thereof, wherein the antibody or antigen binding fragment comprises a variable light chain comprising an amino acid sequence as set out in SEQ ID NO: 12; and a variable heavy chain comprising an amino acid sequence as set out in SEQ ID NO: 15.

In one embodiment of this aspect, there is provided an antibody or an antigen binding fragment thereof, wherein the antibody or antigen binding fragment comprises a variable light chain comprising an amino acid sequence as set out in SEQ ID NO: 9; and a variable heavy chain comprising an amino acid sequence as set out in SEQ ID NO: 16.

In one embodiment of this aspect, there is provided an antibody or an antigen binding fragment thereof, wherein the antibody or antigen binding fragment comprises a variable light chain comprising an amino acid sequence as set out in SEQ ID NO: 10; and a variable heavy chain comprising an amino acid sequence as set out in SEQ ID NO: 16.

In one embodiment of this aspect, there is provided an antibody or an antigen binding fragment thereof, wherein the antibody or antigen binding fragment comprises a variable light chain comprising an amino acid sequence as set out in SEQ ID NO: 11; and a variable heavy chain comprising an amino acid sequence as set out in SEQ ID NO: 16.

In one embodiment of this aspect, there is provided an antibody or an antigen binding fragment thereof, wherein the antibody or antigen binding fragment comprises a variable light chain comprising an amino acid sequence as set out in SEQ ID NO: 12; and a variable heavy chain comprising an amino acid sequence as set out in SEQ ID NO: 16.

In one embodiment, the antibody or antigen binding fragment according to the present invention, comprises a heavy chain constant region selected from the group consisting of IgG1, IgG2, IgG3, IgG4, IgM, IgA and IgE constant regions or any allelic variation thereof as discussed in Kabat et al. (Kabat, E. A., et al. (1991) Sequences of Proteins of Immunological Interest, Fifth Edition, U.S. Department of Health and Human Services, NIH Publication No. 91-3242), included herein by reference. Any of such sequences may be used in the present invention. In a more preferred embodiment, the antibody heavy chain constant region is IgG1. The amino acid sequence of human IgG1 constant region is known in the art and set out in SEQ ID NO: 23.

In one embodiment, the antibody or antigen binding fragment according to the present invention comprises a light chain constant region selected from the group consisting of κ- and λ-chain constant regions or any allelic variation thereof as discussed in Kabat et al. (Kabat, E. A., et al. (1991) Sequences of Proteins of Immunological Interest, Fifth Edition, U.S. Department of Health and Human Services, NIH Publication No. 91-3242), included herein by reference. Any of such sequences may be used in the present invention. In a more preferred embodiment, the antibody light chain constant region is K. The amino acid sequence of human K chain constant region is known in the art and set out in SEQ ID: 24.

In one embodiment, the antigen binding fragment according to the present invention is a Fab fragment, or a F(ab')$_2$ fragment or a single chain Fv fragment.

Antibodies or antigen binding fragments according to the invention can comprise any combination of the variable light and heavy chains defined above.

According to one aspect of the invention there is provided improved antibodies, or antigen binding fragments with high affinity for Aβ protofibrils for use in therapy e.g. by administration of one or more antibodies, or antigen binding fragments according to the invention to a patient having or at risk of developing Alzheimer's disease and other disorders associated with Aβ protein aggregation, such as traumatic brain injury (TBI), dementia with Lewy body (DLB), Down syndrome (DS), Amyotrophic lateral sclerosis (ALS), Frontotemporal dementia, tauopathies, systemic amyloidosis, atherosclerosis and Parkinson's disease dementia (PDD). A suitable dose may vary within broad ranges, e.g. from 0.01 to 100 mg/kg/dose, depending on the medical indication and the patient's status, the route of administration, e.g. i.v., s.c., infusion or by local administration, in addition to the frequency chosen, e.g. single dose, daily, weekly, quarterly or even less frequent administration.

In one aspect, there is provided an antibody, or an antigen binding fragment thereof of the invention, for use in therapy.

In one aspect, there is provided an antibody, or an antigen binding fragment thereof of the invention, for use in treatment and/or prophylaxis of Alzheimer's disease and other disorders associated with Aβ protein aggregation. Typically, such other disorders may be selected from traumatic brain injury (TBI), Lewy body dementia (LBD), Down syndrome (DS), Amyotrophic lateral sclerosis (ALS), Frontotemporal dementia, tauopathies, systemic amyloidosis, atherosclerosis and Parkinson's disease dementia (PDD).

In one aspect, there is provided use of an antibody, or an antigen binding fragment thereof of the invention, in the manufacture of a medicament useful in the treatment and/or prophylaxis of Alzheimer's disease and other disorders associated with Aβ protein aggregation. Typically, such other disorders may be selected from traumatic brain injury (TBI), Lewy body dementia (LBD), Down syndrome (DS), Amyotrophic lateral sclerosis (ALS), Frontotemporal dementia, tauopathies, systemic amyloidosis, atherosclerosis and Parkinson's disease dementia (PDD).

In one aspect, there is provided a method of reducing amount of Aβ protofibrils in persons, comprising administering to the person a therapeutically effective amount of an antibody, or an antigen binding fragment thereof of the invention.

In one aspect, there is provided a method for treatment and/or prophylaxis of Alzheimer's disease and other disorders associated with Aβ protein aggregation in a subject having or at risk of developing the disease, comprising administering to the person a therapeutically effective amount of an antibody, or an antigen binding fragment thereof, of the invention. Typically, such other disorders may be selected from traumatic brain injury (TBI), Lewy body dementia (LBD), Down syndrome (DS), Amyotrophic lateral sclerosis (ALS), Frontotemporal dementia, tauopathies, systemic amyloidosis, atherosclerosis and Parkinson's disease dementia (PDD).

A "subject" is typically a mammal, such as a human. Other mammals represent such mammals, where veterinary use/treatment/propfylaxis would apply.

In one aspect, there may be provided a method for measuring amount of Aβ protofibrils and/or aggregated Aβ protein in a person, comprising contacting the person's tissue or body fluid, in vivo or in vitro, with a labeled antibody, or an antigen binding fragment thereof of the invention and measuring the amount of antibodies, or antigen binding fragments bound to said Aβ protofibrils and/or aggregated Aβ protein. The antibodies or antigen binding fragments could be labeled with a radioactive ligand such as $I^{131}$, $C^{11}$, $C^{14}$, $H^3$, $F^{18}$, or Gallium$^{68}$, but not limited to these radioisotopes, for detection purposes.

In one aspect, there may be provided a method for diagnosis of Alzheimer's disease and other disorders associated with Aβ protein aggregation, such as traumatic brain injury (TBI), dementia with Lewy body (DLB), Down syndrome (DS), Amyotrophic lateral sclerosis (ALS), Frontotemporal dementia, tauopathies, systemic amyloidosis, atherosclerosis and Parkinson's disease dementia (PDD), in persons having or at risk of developing the disease comprising contacting the person's tissue or body fluid, in vivo or in vitro, with an antibody of the invention, or an antigen binding fragment thereof, and measuring the amount of antibody or antigen binding fragment bound to aggregated protein. Typically, said other disorders are associated with Aβ protein aggregation may be selected from traumatic brain injury (TBI), dementia with Lewy body (DLB), Down syndrome (DS), Amyotrophic lateral sclerosis (ALS), Frontotemporal dementia, tauopathies, systemic amyloidosis, atherosclerosis and Parkinson's disease dementia (PDD). Typically, a person's body fluid or tissue would be analysed in vivo or in vitro (in a sample taken from the patient) by contact with a preparation of one or more antibodies or antigen binding fragments of the invention and the amount of antibodies or antigen binding fragments bound to Aβ protofibrils would be measured. Quantification of protofibrils would be used in diagnosis of diseases mentioned above, follow up of various treatments as well as in the development of new medicines. Optionally, the antibodies or antigen binding fragments thereof, in such a preparation, would be labelled with an agent, which would be detected and measured by any of the techniques known in the art, e.g. analysis by ELISA, Biacore and/or imaging with SPECT, PET, MRI. The antibodies or antigen binding fragments could be labeled with a radioactive ligand such as $I^{131}$, $C^{11}$, $C^{14}$, $H^3$, $F^{18}$ or Gallium$^{68}$, but not limited to these radioisotopes, for detection purposes.

According to a further aspect of the invention a pharmaceutical composition is prepared, comprising an effective amount of one or more of the antibodies or antigen binding fragment thereof according to the invention. A medical composition comprising an antibody according to the invention may comprise, in addition to an effective amount of the antibody, other components known for use in such preparations, e.g. buffers, components for preservation and stability.

In another aspect there may be provided an antibody of the invention, for veterinary use. Typically, said veterinary use would include treatment and/or prophylaxis of disorders associated with Aβ protein aggregation.

According to a further aspect of the invention there may be provided therapy utilizing antibodies according to the invention in combination with symptomatic treatments, such as acetylcholine esterase inhibitors, NMDA antagonists and 5HT6 inhibitors.

Combination with other disease modifying treatments, such as γ-secretase inhibitors (GSI), γ-secretase modulators (GSM), β-secretase (BACE) inhibitors, BACE modulators, vaccines, other antibodies, drugs targeting tau or neuroinflammatory processes, antihypertensives, etc., offers additional possibilities for efficient therapy.

Combination with nutrition products may offer additional possibilities for efficient therapy.

In one aspect, there is provided a pharmaceutical composition comprising an antibody of the invention, together with pharmaceutically acceptable excipient and/or diluents, said composition further may comprise an additional, therapeutic agent. Typically, said additional therapeutic agent may be selected from acetylcholine esterase inhibitors, NMDA antagonists, 5HT6 inhibitors, GSI, GSM, BACE inhibitors, BACE modulators, vaccines, other antibodies, drugs targeting tau or neuroinflammatory processes, antihypertensives and a nutrition product. The composition may be provided as a single or sequential dose.

The present invention will be illustrated by a number of non-limiting examples:

Example 1

Production of Antibodies and Methods Used

Production of Reference Antibody

The reference antibody BAN2401 was produced according to previously described methods in EP2004688.

Production of the Antibodies of the Invention

The antibodies of the invention were produced by transient and/or stable production in Chinese Hamster Ovary (CHO) cells using the CHOK1SV GS and CHOK1SV GS-KO Xceed™ expression systems (Lonza), respectively. The following mutants were produced by transient transfection using the CHOK1SV GS-KO Xceed™ expression system: A17D, A17D/R79T and A17D/R79T/R82S. The following mutants were produced by both transient and stable transfection using the CHOK1SV GS-KO Xceed™ expression system: A17D/R79T_DI 1, A17D/R79T_DI 2, A17D/R79T_DI 3, A17D/R79T_DI 4, A17D/R79T_DI 5, A17D/R79T_DI 6, A17D/R79T_DI 7 and A17D/R79T_DI 8. The A17D/R82S mutant was produced by stable transfection using the CHOK1SV GS expression system.

Sequences of the light and heavy chain encoding regions of the mutants were synthesized by using conventional methods.

For transient transfections in the CHOK1SV GS-KO Xeed™ expression system, light chain encoding regions were sub-cloned into the pXC-17.4 vector and heavy chain encoding regions into the pXC-18.4 vector. Expression cultures were harvested 6 days post-transfection and clarified by centrifugation and sterile filtration. The clarified cell culture supernatants were subjected to purification using Protein A chromatography. Eluted antibody was provided in PBS (pH 7.4). The products were further purified by preparative Size Exclusion Chromatography (SEC) to remove aggregates. The monomer peak collected was thereafter analysed by analytical SEC, and aggregate levels were determined to be below 2% for all products.

Stable expression in the CHOK1SV GS-KO Xeed™ system was performed essentially according to the manufacturer's recommendations. In brief, the two vectors containing the light and heavy chains (pXC-17.4 and pXC-18.4) were ligated into one double gene vector containing both genes. CHOK1SV GS-KO cells were transfected by electroporation with the linearized double gene vector. Screening of clones and productivity screening of death cultures were analyzed by ELISA. Productions were performed with CD-CHO medium supplemented with 15% Feed A and 15% Feed B (Life Technologies). Supernatants were harvested by centrifugation and sterile filtration. The clarified cell culture supernatants were purified using Protein G chromatography and buffer exchanged to Dulbecco's PBS (Gibco).

For stable transfection using the CHOK1SV GS expression system (Lonza), the heavy chain gene was ligated into the pEE6.4 vector and the light chain gene in pEE12.4 vector. The two vectors were ligated to form a double gene vector. CHOK1SV cells were transfected by electroporation with the linearized double gene vector. In essence, transfections were performed according to the manufacturer's recommendations. Screening of clones and productivity screening of death cultures were analyzed by ELISA. Productions were performed with CD-CHO medium supplemented with 15% Feed A and 15% Feed B (Life Technologies). Supernatants were harvested by centrifugation and sterile filtration. The clarified cell culture supernatants were purified using Protein G chromatography and buffer exchanged to Dulbecco's PBS (Gibco). Product quality analysis by Size Exclusion HPLC and SDS-PAGE were carried out using purified material of all mutants produced.

Target Binding Analysis by Inhibition ELISA

The binding characteristics towards Aβ protofibrils and Aβ monomers of the antibodies of the invention compared to BAN2401 were analyzed using an inhibition ELISA in which antibodies were pre-incubated in solution with Aβ protofibrils or Aβ monomers and then transferred to Aβ coated ELISA plates, as described in Tucker et. al. J Alzheimers Dis. 2015; 43(2):575-88. doi: 10.3233/JAD-140741. PubMed PMID: 25096615, and references cited therein.

Pharmacokinetic Studies in Wild Type Mice 8-10 weeks old female C57BL/6 mice were grouped and given single intravenous (i.v.) injections of BAN2401 or antibodies of the invention at a dosage of 10 mg/kg. Plasma from all animals was collected at time points varying from 30 minutes to 29 days post injection and used for measurements of antibody concentrations and subsequent calculations of pharmacokinetic (PK) parameters. Mice were sacrificed at the terminal plasma collection time point.

Pharmacokinetic Studies in Rats 8 weeks old female Sprague Dawley rats were grouped and given single i.v. injections of BAN2401 or antibodies of the invention at a dosage of 10 mg/kg. Plasma from all animals was collected at time points varying from 30 minutes to 29 days post injection and used for measurements of antibody concentrations and subsequent calculations of PK parameters. Rats were sacrificed at the terminal plasma collection time point.

Pharmacokinetic Studies in Monkeys

Male cynomolgus monkeys were grouped (N=3) and subjected to single i.v. infusions of 5 mg/kg BAN2401 or 10 mg/kg of the antibodies of the invention. Serum from all animals was collected at time points varying from 5 minutes to 28 days post injection and used for measurements of antibody concentrations. Serum levels of BAN2401 and the antibodies of the invention were determined by ELISA. Biotinylated Aβ1-42 protofibrils were added to an avidin immobilized microplate for coating. After blocking, monkey serum samples were added to the wells. After washing away any unbound substances, alkaline Phosphatase (AP) labeled goat anti-human IgG was added to the wells. Following a wash to remove any unbound reagents, p-nitrophenylphosphate, a substrate for AP, was added to the wells. The reaction was stopped with sodium hydroxide solution and absorbance was measured at 405 nm and 492 nm. Absorbance at 492 nm was subtracted from that at 405 nm. Values were translated to concentrations by means of a standard curve and used for subsequent calculations of PK parameters.

Direct ELISA for Measurement of Aβ Antibodies

Levels of BAN2401 and antibodies of the invention in cell culture media, purified antibody product, and plasma collected in the mouse and rat PK studies were measured by direct ELISA for measurement of anti-Aβ antibodies. Samples were serially diluted and incubated in microtiter plate wells coated with Aβ1-40 to allow for BAN2401 and the antibodies of the invention to bind. Horse radish peroxidase (HRP)-conjugated goat anti-human IgG was utilized as detection antibody and TMB, a substrate for HRP, was added. The reaction was stopped by addition of 2M $H_2SO_4$, which results in a yellow color that is measured at 450 nm. The method was employed in a quantitative manner, where $OD_{450}$ values are translated into concentrations by means of a standard curve.

Calculations of PK Parameters by Non-Compartmental Analysis

Individual terminal half-life calculations were performed using a non-compartmental model with the Phoenix WinNonLin 6.3 software (Pharsight). Area under the curve ($AUC_{0-inf}$) calculations were performed with Phoenix WinNonLin using the lin-up log-down method. Group means and standard deviations of AUCs and terminal half-lives were calculated using GraphPad Prism (v 6.04).

Statistical Analyses

Statistical analyses of group means of individually determined terminal half-lives and AUCs were performed using the GraphPad Prism software (v. 6.04). One-way ANOVA followed by Bonferroni's multiple comparisons post-test was used in the studies. Tests were performed at significance levels * $P<0.05$,  $P<0.01$, * $P<0.001$ and **** $P<0.0001$.

Example 2

Target Binding Characterization

Aβ-Protofibrils Binding Preserved in A17D, A17D/R79T, A17D/R82S and A17D/R79T/R82S Compared to BAN2401

The target binding profiles of the antibodies of the invention were analyzed next to BAN2401 (control) by inhibition ELISA as described in Example 1 (inhibition ELISA). Results are presented in FIG. 1, where analysis of binding and selectivity for Aβ protofibrils compared to Aβ monomers for A17D, A17D/R79T, A17D/R82S and A17D/R79T/R82S and BAN2401 are shown. Results showed that the binding and selectivity of binding to Aβ protofibrils as compared to binding to the Aβ monomer was preserved in antibodies of the invention (A17D, A17D/R79T, A17D/R82S and A17D/R79T/R82S).

Example 3

Pharmacokinetic Profile of Antibodies in Mice

Pharmacokinetic Study of BAN2401, A17D, A17D/R79T, A17D/R82S, A17D/R79T/R82S in Wild-Type Mice In order to study the pharmacokinetic profile of the antibodies of the invention in wild-type mice, 8-10 weeks old C57BL/6 female mice were dosed with single i.v. injections of 10 mg/kg BAN2401 (N=8), A17D (N=7), A17D/R79T (N=6), A17D/R82S (N=8) or A17D/R79T/R82S (N=7). Animals were bled after 0.5 h, 2 days, 7 days, 14 or 15 days, and 28 or 29 days and levels of BAN2401 and antibodies of the invention were analysed by ELISA using Aβ1-40 for capture and HRP-coupled goat-anti-human IgG for detection as described in Example 1 (direct ELISA). A17D/R82S was administered in a study started at a separate occasion compared to the other antibodies. However, plasma samples from the two different studies were analyzed by ELISA at the same time to avoid inter-assay variation.

Figure 2:
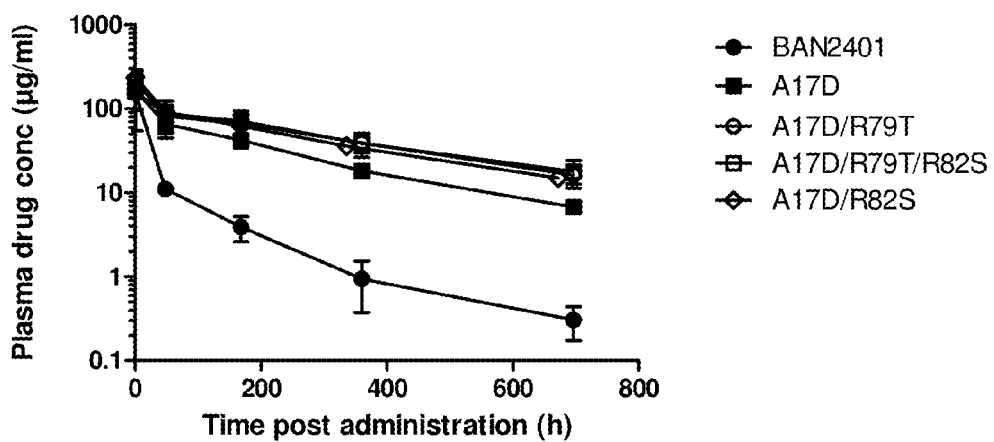
FIG. 2 provides plasma drug exposure of BAN2401 and antibodies of the invention in mice presented as time vs concentration graphs. Plasma levels after single i.v. injection of BAN2401, A17D, A17D/R79T and A17D/R79T/R82S collected at time points 0.5 h, 2 days, 7 days, 15 days and 29 days post administration, and of A17D/R82S collected at time points 0.5 h, 2 days, 7 days, 14 days and 28 days post administration are shown in the graph. A17D/R82S was not included in the same PK study as the other antibodies shown here, but was instead given at a separate occasion. However, with exception of two plasma sampling time points, the same study design was used for the two separate studies. All plasma samples were analyzed by ELISA at the same occasion to avoid inter-assay variation. The plasma drug concentration in µg/ml is shown on the y-axis (logarithmic scale) and the time post administration in hours (h) is shown on the x-axis. Mean group values are shown with error bars indicating standard deviations. Mean $AUC_{0-inf}$ values and terminal half-lives were calculated by non-compartment analysis using Phoenix WinNonlin 6.3 (Pharsight) and are shown in Table 1.

As shown in the time vs concentration graphs in FIG. 2 and the calculated PK parameters presented in Table 1, the PK profiles of the antibodies of the invention (A17D, A17D/R79T, A17D/R82S and A17D/R79T/R82S) differ substantially from BAN2401, especially during the first 48 hours post injection. Whereas a 6-fold increase in exposure, measured as area under the curve ($AUC_{0-inf}$), was seen for A17D compared to BAN2401 the AUCs of A17D/R79T, A17D/R82S and A17D/R79T/R82S were improved by 10-11 times (Table 1). Also, the terminal plasma half-lives of the antibodies of the invention were considerably prolonged compared to BAN2401 (Table 1).

TABLE 1

Plasma PK parameters of BAN2401, A17D, A17D/R79T, A17D/R82S and A17D/R79T/R82S in mice. Half-life and $AUC_{0-inf}$ for all antibodies were calculated individually for all animals by non-compartmental analysis using Phoenix WinNonlin 6.3 (Pharsight) and subjected to statistical analysis by one-way ANOVA followed by Bonferroni's Multiple Comparisons post-test. Mean $AUC_{0-inf}$ values and mean terminal half-lives are shown in the table. Statistical differences in terminal half-life and $AUC_{0-inf}$ between BAN2401 and the mutants are indicated in the table, where * denotes $p < 0.001$, and **$p < 0.0001$.

| Antibody | $AUC_{0-inf}$ (mg*h/ml) | Terminal half-life (days) |
| --- | --- | --- |
| BAN2401 | 3.7 | 4.5 |
| A17D | 23.3**** | 8.7*** |
| A17D/R79T | 40.2**** | 10.7**** |
| A17D/R82S | 37.9**** | 11.1**** |
| A17D/R79T/R82S | 41.0**** | 10.9**** |

Example 4

Pharmacokinetic Profile of Antibodies in Rat

Pharmacokinetic Study of BAN2401, A17D, A17D/R79T and A17D/R79T/R82S in Rats

Figure 3:
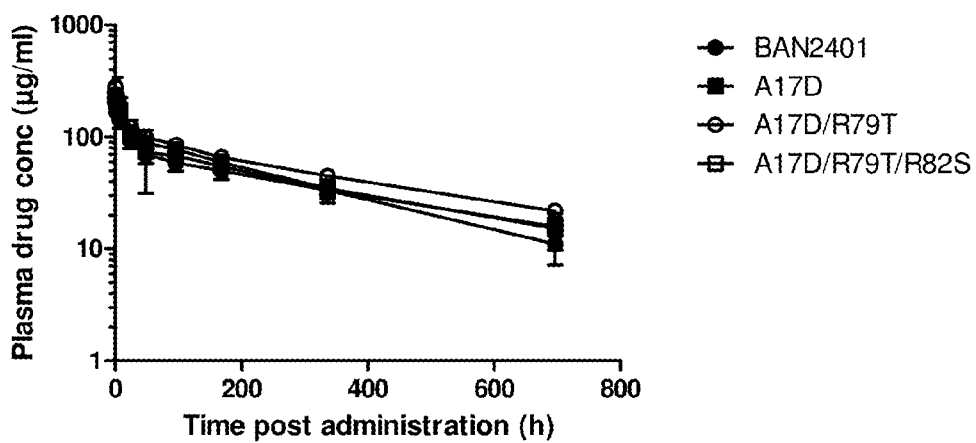
FIG. 3 provides plasma drug exposure of BAN2401 and antibodies of the invention, in rats presented as time vs concentration graphs. Plasma levels after single i.v. injection of BAN2401, A17D, A17D/R79T and A17D/R79T/R82S collected at time-points 0.5 h, 2 h, 7 h, 24 h, 2 days, 4 days, 7 days, 14 days and 29 days post administration are shown in the graph. The plasma drug concentration in µg/ml is shown on the y-axis (logarithmic scale) and the time post administration in hours (h) is shown on the x-axis. Mean group values are shown with error bars indicating standard deviations. Mean $AUC_{0-inf}$ values and mean terminal half-lives were calculated by non-compartment analysis using Phoenix WinNonlin 6.3 (Pharsight) and are shown in Table 2.
Figure 4:
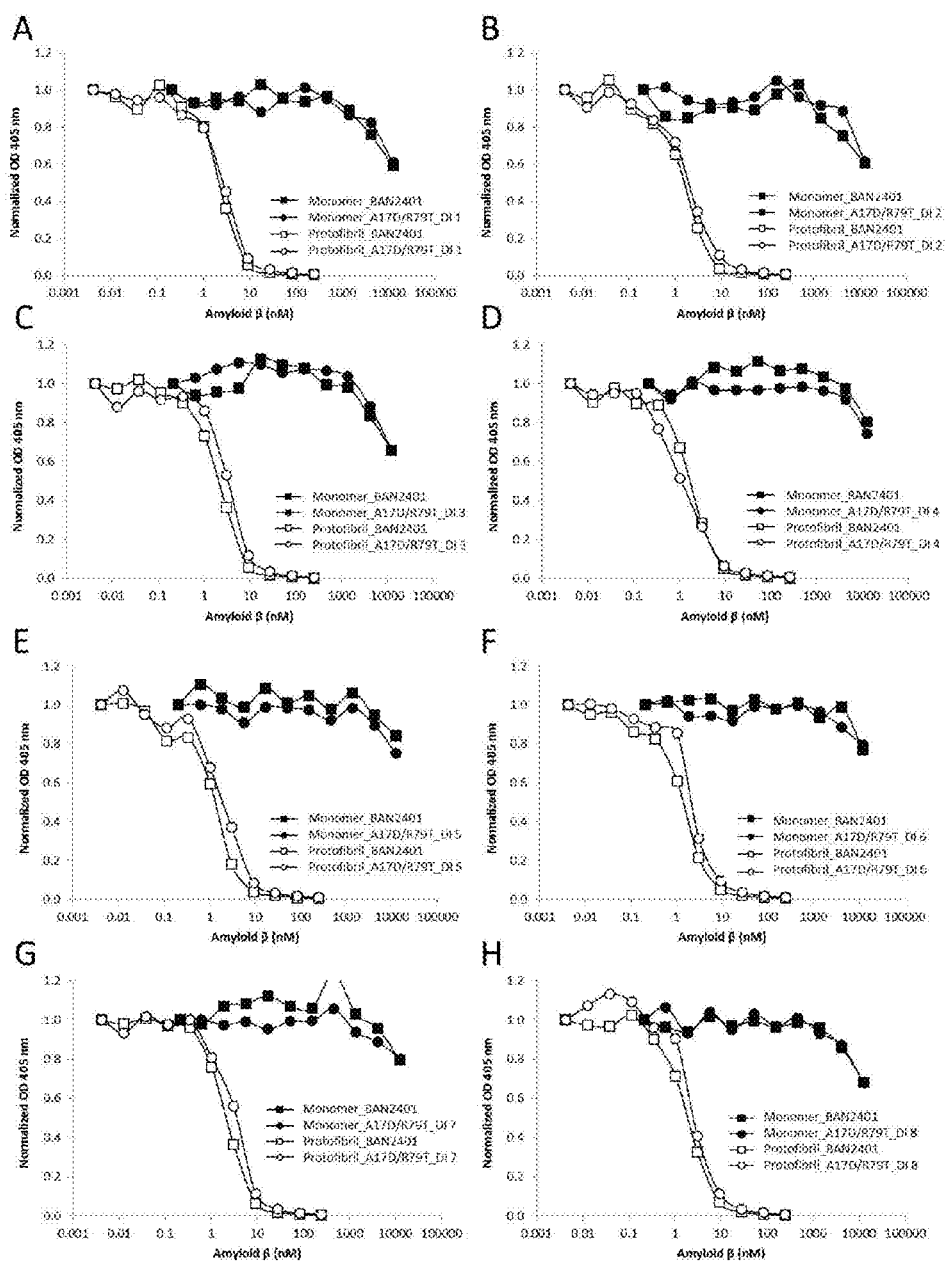
FIG. 4 provides data with analysis of binding and selectivity for Aβ protofibrils compared to Aβ monomers for the deimmunized variants of A17D/R79T (A17D/R79T_DI 1-8) compared to BAN2401. Binding inhibition by Aβ1-42 protofibrils in solution is shown by open circles and open squares, and binding inhibition by Aβ1-40 monomers in solution are shown by closed circles and closed squares. A) A17D/R79T_DI 1, B) A17D/R79T_DI 2, C) A17D/R79T_DI 3, D) A17D/R79T_DI 4, E) A17D/R79T_DI 5, F) A17D/R79T_DI 6, G) A17D/R79T_DI 7, H) A17D/R79T_DI 8.
Figure 5:
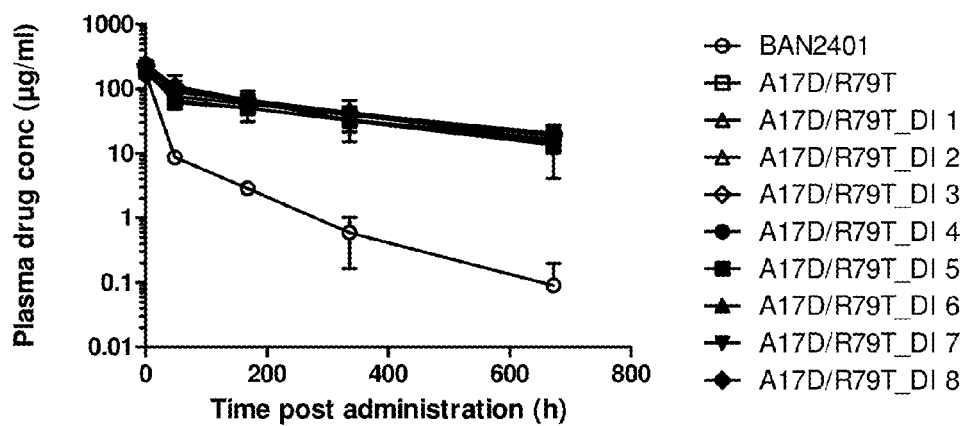
FIG. 5 provides plasma drug exposure of BAN2401 and antibodies of the invention, in mice presented as time vs concentration graphs. Plasma levels after a single i.v. injection of BAN2401, A17D/R79T and 8 deimmunized variants of A17D/R79T (A17D/R79T_DI 1-8) collected at time points 0.5 h, 2 days, 7 days, 14 days and 28 days post administration. The plasma drug concentration in µg/ml is shown on the y-axis (logarithmic scale) and the time post administration in hours (h) is shown on the x-axis. Mean group values are shown with error bars indicating standard deviations. Mean $AUC_{0-inf}$ values and mean terminal half-lives were calculated by non-compartment analysis using Phoenix WinNonlin 6.3 (Pharsight) and are shown in Table 6.
Figure 6:
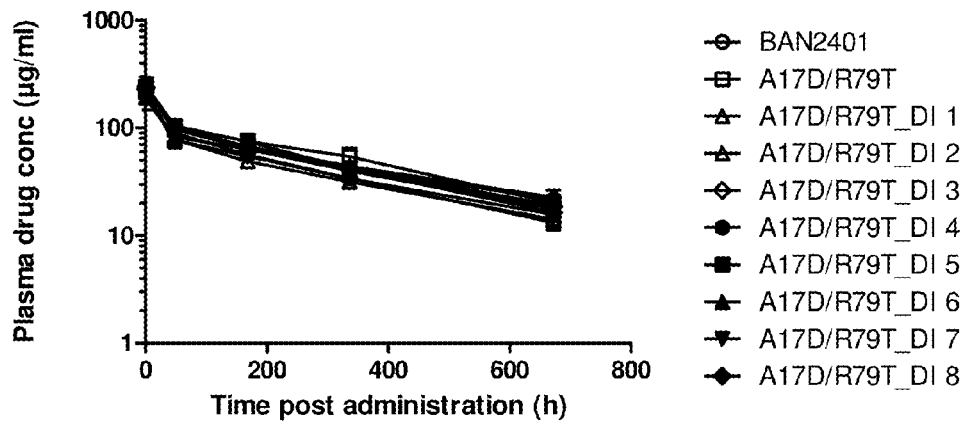
FIG. 6 provides plasma drug exposure of BAN2401 and mutants in rat presented as time vs concentration graphs. Plasma levels after a single i.v. injection of BAN2401, A17D/R79T and 8 deimmunized variants of A17D/R79T (A17D/R79T_DI 1-8) collected at time points 0.5 h, 2 days, 7 days, 14 days and 28 days post administration. The plasma drug concentration in µg/ml is shown on the y-axis (logarithmic scale) and the time post administration in hours (h) is shown on the x-axis. Mean group values are shown with error bars indicating standard deviations. Mean $AUC_{0-inf}$ values and mean terminal half-lives were calculated by non-compartment analysis using Phoenix WinNonlin 6.3 (Pharsight) and are shown in Table 7.

In order to study the pharmacokinetic profile of the antibodies of the invention in rats, 8 weeks old female Sprague Dawley rats were dosed with single i.v. injections of 10 mg/kg BAN2401 (N=3), A17D (N=4), A17D/R79T (N=6) or A17D/R79T/R82S (N=5). Animals were bled after 0.5 h, 2 h, 7 h, 24 h, 2 days, 4 days, 7 days, 14 days and 29 days post injection. Levels of BAN2401 and antibodies of the invention were analysed by ELISA using Aβ1-40 for capture and HRP-coupled goat-anti-human IgG for detection as described in Example 1 (direct ELISA). The rapid reduction of BAN2401 levels in plasma of wild-type mice during the first 48 hours post administration leading to low exposure (FIG. 2) is not seen in rat, and instead BAN2401 and the antibodies of the invention display similar PK profiles (FIG. 3). Statistical analysis of plasma half-lives and $AUC_{0-inf}$ values calculated individually for all rats in the study, suggested no major differences in $AUC_{0-inf}$ or terminal half-life between BAN2401 and A17D or A17D/R79T/R82S (Table 2). While, a significant increase in $AUC_{0-inf}$ was indicated for A17D/R79T compared to BAN2401 there was no statistical difference in terminal half-life between the two of them (Table 2).

TABLE 2

Plasma PK parameters of BAN2401, A17D, A17D/R79T and A17D/R79T/R82S in rats. Half-lives and $AUC_{0-inf}$ values for all antibodies were calculated individually for all animals by non-compartmental analysis using Phoenix WinNonlin 6.3 (Pharsight) and subjected to statistical analysis by one-way ANOVA followed by Bonferroni's Multiple Comparisons post-test. Mean $AUC_{0-inf}$ values and mean terminal half-lives of BAN2401, A17D, A17D/R79T and A17D/R79T/R82S calculated are shown in the table. Statistical differences in terminal half-life and $AUC_{0-inf}$ between BAN2401 and the mutants are indicated in the table, where ** denotes $P < 0.01$.

| Antibody | $AUC_{0-inf}$ (mg*h/ml) | Terminal half-life (days) |
| --- | --- | --- |
| BAN2401 | 31.1 | 10.2 |
| A17D | 38.0 | 10.9 |
| A17D/R79T | 47.6** | 12.8 |
| A17D/R79T/R82S | 36.6 | 11.2 |

Example 5

Deimmunization

Ex Vivo Whole Protein T Cell Assay of BAN2401, A17D, A17D/R79T and A17D/R79T/R82S In order to evaluate whether mutations introduced in the antibodies of the invention had led to an increased risk for an immunogenic response in humans, A17D, A17D/R79T and A17D/R79T/R82S were analyzed next to BAN2401 by an ex vivo whole protein T cell activation assay. The EpiScreen™ time course T cell assay measures the capacity of an antibody to induce CD4+ T cell responses (Antitope Ltd, Cambridge, UK). The samples were tested against CD8+ depleted peripheral blood mononucleated cells (PBMC) from a cohort of 25 healthy donors (Donor 1-25, Table 3) with a broad HLA-diversity. The ability of the antibodies to induce CD4+ T cell responses was measured by proliferation and IL-2 secretion.

Results from the study indicated that the overall potential risk of immunogenicity was low for BAN2401 and borderline low for A17D with 8% and 12% of donors responding positively, respectively (Table 3). Analysis of A17D/R79T and A17D/R79T/R82S revealed unexpectedly somewhat higher risks of immunogenicity, as the combined frequency of proliferation and IL-2 secretion was 24% and 20% of the study cohort, respectively.

TABLE 3

Summary of healthy donor T cell proliferation and IL-2 ELISpot responses for BAN2401, A17D, A17D/R79T and A17D/R79T/R82S. Positive T cell responses for proliferation are indicated with a "P" and positive ELISpot responses are indicated with an "E". Borderline responses are indicated (*). Correlation is expressed as the percentage of proliferation responses also positive in the ELISpot assay. To be considered a response in one donor, both the proliferation and ELISpot assays have to be positive. Humanized A33 (Welt S et al., Clin Cancer Res. 2003 April; 9(4): 1347-53., 2003), which is a therapeutic antibody control with a known mean immunogenicity of 32% in the clinic, typically stimulates 20-30% of donors to respond positively in the T cell proliferation assay. Phytohaemagglutinin (PHA) and Keyhole Limpet Hemocyanin (KLH) are potent antigens used as positive controls.

|  | BAN2401 | A17D | A17D/R79T | A17D/R79T/R82S | A33 | KLH | PHA |
|---|---|---|---|---|---|---|---|
| Donor 1 |  |  |  | PE |  | PE | PE |
| Donor 2 |  | PE | P*E |  | PE | PE | PE |
| Donor 3 |  |  | E* |  |  | PE | PE |
| Donor 4 |  |  |  |  |  | PE | PE |
| Donor 5 |  |  |  |  |  | PE | PE |
| Donor 6 |  |  |  |  |  | PE | PE |
| Donor 7 |  |  |  |  |  | PE | PE |
| Donor 8 |  |  | PE | PE |  | PE | PE |
| Donor 9 |  |  |  |  |  | PE | PE |
| Donor 10 |  |  |  |  |  | PE | PE |
| Donor 11 |  |  |  |  |  | E | PE |
| Donor 12 |  |  |  |  |  | P* | PE |
| Donor 13 |  |  |  |  | PE | PE | PE |
| Donor 14 |  |  | PE | PE | PE | PE | PE |
| Donor 15 |  |  |  |  | P | PE | PE |
| Donor 16 | PE | P | P | P | E | PE | PE |
| Donor 17 |  |  | PE | PE | PE | PE | PE |
| Donor 18 |  |  |  |  |  | PE | PE |
| Donor 19 | PE | PE | PE | PE |  | PE | PE |
| Donor 20 |  |  |  |  |  | PE | PE |
| Donor 21 | P | PE* | P | P |  | PE | PE |
| Donor 22 |  |  |  |  |  | E | PE |
| Donor 23 |  |  | PE |  |  | PE | PE |
| Donor 24 |  |  |  | E | PE | PE | PE |
| Donor 25 |  |  |  |  |  | PE | PE |
| Proliferation % | 12 | 16 | 32 | 28 | 24 | 92 | 100 |
| ELISpot % | 8 | 12 | 28 | 24 | 24 | 96 | 100 |
| Proliferation and ELISpot % | 8 | 12 | 24 | 20 | 20 | 88 | 100 |
| Correlation % | 67 | 75 | 75 | 71 | 83 | 96 | 100 |

T-Cell Epitope Screening of BAN2401 in Silico

To further address the immunogenicity risk inferred by the mutations and to find relevant positions to deimmunize, BAN2401, A17D, A17D/R79T, A17D/R82S and A17D/R79T/R82S were subjected to in silico T cell epitope screening. Variable region sequences of BAN2401, A17D, A17D/R79T, A17D/R82S and A17D/R79T/R82S were provided to Antitope Ltd (Cambridge, UK) for analysis by their proprietary in silico technologies iTope™ and TCED™. Non-germline promiscuous MHC class II binding sequences were identified in both the heavy chains and the light chains of the antibodies analyzed. BLAST search analysis of the TCED™ revealed two partial matches to previously identified epitopes in the database of peptides with known immunogenicity ex vivo.

Ex Vivo T Cell Epitope Mapping of BAN2401, A17D, A17D/R79T, A17D/R82S and A17D/R79T/R82S In order to verify the immunogenicity risk inferred by the new mutations and to identify positions to deimmunize, 44 peptides (15-mers) derived from variable regions of BAN2401, A17D, A17D/R79T, A17D/R82S and A17D/R79T/R82S were assessed for the presence of CD4+ T cell epitopes using EpiScreen™ T cell epitope mapping technology (Antitope Ltd, Cambridge, UK). The peptides were chosen to cover all the potential T cell epitopes identified by the in silico screen and also the two regions covering the areas of the A17D substitution and the R79T and R82S substitutions (including peptides with or without mutations).

The peptides were tested against a cohort of 11 human donors selected from the Episcreen™ whole antibody analysis described in the previous section. T cell responses were measured for each donor against each peptide using a proliferation assay that measures $^3$[H]-thymidine incorporation. The results identified the presence of three potential T cell epitopes in the sequences (Epitope 1, 5 and 8). "Epitope 1" present in the heavy chain was considered weak. "Epitope 5" including the A17D mutation was weak and no donor responses were observed to the related peptide of the wild-type BAN2401 sequence. "Epitope 8" was the most significant epitope based upon frequency of T cell responses and was identified in the peptides of antibodies A17D/R79T, A17D/R82S and A17D/R79T/R82S but not in wild-type BAN2401 or A17D.

The data from the ex vivo T cell epitope mapping supported the conclusion from the whole antibody time course T cell assay that A17D/R79T and A17D/R79T/R82S are associated with an increased overall risk of immunogenicity. In addition, also A17D/R82S (not included in the whole antibody T cell assay) appeared to have increased risk of immunogenicity due to the R82S mutation in "Epitope 8".

Deimmunization of Peptides Identified as Potential T Cells Epitopes by Ex Vivo T Cell Epitope Mapping In general, deimmunization is achieved by changing a single amino acid in one of the important anchoring positions (p1, p4, p6, p7 and p9 of a 9-mer) of the potential MHC class II binding peptide. Specific deimmunizing mutations in the three epitopes identified in the ex vivo peptide mapping (Epitope 1, 5 and 8) described above were chosen. The substitutions were chosen based on anticipated reduced binding affinity of the peptide to the binding pocket of the MHC class II molecule. Two deimmunizing substitutions were tested for each peptide that had been indicated as potentially immunogenic, and these peptides were analyzed alongside with the original peptides of BAN2401, A17D, A17D/R79T, A17D/R82S and A17D/R79T/R82S using the Episcreen™ peptide mapping technology.

T cell responses were measured for each donor against each peptide using a proliferation assay that measures $^3$[H]-thymidine incorporation. The results from this study confirmed the earlier findings, but all epitopes (Epitope 1, 5 and 8) were considered weak in this study (Table 4). Nevertheless, all deimmunizing substitutions successfully reduced the risk of immunogenicity for the peptides covering the three epitopes compared to the original peptides, with no or very few T cell responders (Table 4). This indicates that the chosen substitutions were effective and that the deimmunizations were successful.

Design and Production of Deimmunized Variants of A17D/R79T

Eight deimmunized variants of A17D/R79T were designed based on the results from the T cell epitope mapping and peptide deimmunization described above. In all three epitopes identified as potentially immunogenic, deimmunization mutations shown to reduce immunogenicity in the ex vivo T cells epitope mapping were introduced in the combinations indicated in Table 5.

TABLE 5

Summary of the eight deimmunized variants of the double mutant A17D/R79T. Deimmunization mutations for the epitopes 1, 5 and 8, chosen and functionally verified in the ex vivo T cell assay on peptide level, are indicated for the specific antibodies. N-terminal numbering has been used. VH = variable heavy chain, VL = variable light chain.

| A17D/R79T variants | Deimmunization in epitope 1 (VH) | Deimmunization in epitope 5 (VL) | Deimmunization in epitope 8 (VL) |
|---|---|---|---|
| A17D/R79T __DI 1 | A40N | I21V | S81Q |
| A17D/R79T __DI 2 | A40N | I21V | E84D |
| A17D/R79T __DI 3 | A40N | V13A | S81Q |
| A17D/R79T __DI 4 | A40N | V13A | E84D |
| A17D/R79T __DI 5 | A40T | I21V | S81Q |
| A17D/R79T __DI 6 | A40T | I21V | E84D |

TABLE 4

Deimmunization results at peptide level of epitopes identified as immunogenic using the EpiScreen ™ T cell epitope mapping technology. Shown are the peptides derived from BAN2401 and the antibodies of the invention that were identified as immunogenic, and the same peptides with deimmunization substitutions introduced (underlined). Half-life improving mutations are shown in bold. All deimmunized peptides were tested in the ex vivo T cell assay and the results are shown in the rightmost column (donor response frequency).

| Epitope area | Antibody of peptide origin and deimmunization substitutions | Peptide | Response frequency (%) |
|---|---|---|---|
| 1. | BAN2401 and antibodies of the invention* | SFGMHWVRQAPGKGL | 12 |
|  | A→N | SFGMHWVRQNPGKGL | 0 |
|  | A→T | SFGMHWVRQTPGKGL | 4 |
| 5. | All antibodies of the invention (A17D mutation) | PVTPGDPASISCRSS | 16 |
|  | I→V | PVTPGDPASVSCRSS | 0 |
|  | V→A | PATPGDPASISCRSS | 0 |
| 8. | A17D/R79T (R79T mutation) | SGSGTDFTLTISRVE | 16 |
|  | S→Q | SGSGTDFTLTIQRVE | 4 |
|  | E→D | SGSGTDFTLTISRVD | 4 |
| 8. | A17D/R79T (R79T mutation) | GTDFTLTISRVEAED | 20 |
|  | S→Q | GTDFTLTIQRVEAED | 0 |
|  | E→D | GTDFTLTISRVDAED | 0 |
| 8. | A17D/R79T/R82S (R79T/R82S mutations) | SGSGTDFTLTISSVE | 12 |
|  | S→Q | SGSGTDFTLTIQSVE | 0 |
|  | E→D | SGSGTDFTLTISSVD | 0 |
| 8. | A17D/R79T/R82S (R79T/R82S mutations) | GTDFTLTISSVEAED | 16 |
|  | S→Q | GTDFTLTIQSVEAED | 0 |
|  | E→D | GTDFTLTISSVDAED | 0 |
| 8. | A17D/R82S (R82S mutation) | SGSGTDFTLRISSVE | 12 |
|  | S→Q | SGSGTDFTLRIQSVE | 0 |
|  | E→D | SGSGTDFTLRISSVD | 4 |
| 8. | A17D/R82S (R82S mutation) | GTDFTLRISSVEAED | 16 |
|  | S→Q | GTDFTLRIQSVEAED | 4 |
|  | E→D | GTDFTLRISSVDAED | 4 |

*Non-deimmunized antibodies

TABLE 5-continued

Summary of the eight deimmunized variants of the double mutant A17D/R79T. Deimmunization mutations for the epitopes 1, 5 and 8, chosen and functionally verified in the ex vivo T cell assay on peptide level, are indicated for the specific antibodies. N-terminal numbering has been used. VH = variable heavy chain, VL = variable light chain.

| A17D/R79T variants | Deimmunization in epitope 1 (VH) | Deimmunization in epitope 5 (VL) | Deimmunization in epitope 8 (VL) |
|---|---|---|---|
| A17D/R79T _DI 7 | A40T | V13A | S81Q |
| A17D/R79T _DI 8 | A40T | V13A | E84D |

Example 6

Target Binding Characterization of Deimmunized Antibodies

Aβ-Protofibril Binding Preserved in Eight Deimmunized Variants of A17D/R79T (A17D/R79T_DI 1-8) Compared to BAN2401

The target binding profiles of the eight deimmunized variants of A17D/R79T (A17D/R79T_DI 1-8) were analyzed next to BAN2401 (control) by inhibition method described in Example 1 (Inhibition ELISA). Results are presented in FIG. 4, where analysis of binding and selectivity for Aβ protofibrils compared to Aβ monomers for A17D/R79T_DI 1-8 and BAN2401 are shown. Results showed that binding and selectivity of binding to Aβ protofibrils as compared to binding to the Aβ monomer was preserved in antibodies of the invention (A17D/R79T_DI 1-8).

Example 7

Pharmacokinetic Profile of Deimmunized Antibodies in Mice

Pharmacokinetic Study of BAN2401, A17D/R79T and Eight Deimmunized Variants of A17D/R79T (A17D/R79T_DI 1-8) in Wild-Type Mice In order to compare the PK profiles of the eight variants of deimmunized A17D/R79T (A17D/R79T_DI 1-8) to the PK profile of BAN2401 and A17D/R79T in wild-type mice, 8-10 weeks old C57BL/6 female mice were grouped (N=5) and subjected to single i.v. injections of 10 mg/kg antibody. Animals were bled after 0.5 h, 2 days, 7 days, 14 days and 28 days and levels of BAN2401 and antibodies of the invention were analysed by ELISA using Aβ1-40 for capture and HRP-coupled goat-anti-human IgG for detection as described in Example 1 (direct ELISA). As shown in the time vs concentration graph in FIG. 5, the PK profile of the deimmunized A17D/R79T mutants (A17D/R79T_DI 1-8) resembles the PK profile of A17D/R79T and differs from BAN2401. Results suggested that both $AUC_{0\text{-}inf}$ and terminal half-life of A17D/R79T and the deimmunized variants (A17D/R79T_DI 1-8) were significantly enhanced compared to BAN2401 (Table 6). Hence, all deimmunized variants showed an improved PK profile compared to BAN2401 and displayed PK profiles that were similar to the PK profile of A17D/R79T, with increased exposure and prolonged elimination half-life.

TABLE 6

Plasma PK parameters of BAN2401, A17D/R79T and deimmunized variants of A17D/R79T (A17D/R79T_DI 1-8) in mice. Half-life and $AUC_{0\text{-}inf}$ for all antibodies were calculated individually for all animals by non-compartmental analysis using Phoenix WinNonlin 6.3 (Pharsight) and subjected to statistical analysis by one-way ANOVA followed by Bonferroni's Multiple Comparisons post-test. Mean $AUC_{0\text{-}inf}$ and mean terminal half-lives are shown in the table. Statistical differences in terminal half-life and $AUC_{0\text{-}inf}$ between BAN2401 and the mutants are indicated in the table, where * denotes $P < 0.05$, $P < 0.01$, *$P < 0.001$ and ****$P < 0.0001$.

| Antibody | $AUC_{0\text{-}inf}$ (mg* h/ml) | Terminal half-life (days) |
|---|---|---|
| BAN2401 | 3.6 | 3.5 |
| A17D/R79T | 38.0**** | 10.7** |
| A17D/R79T_DI 1 | 42.3**** | 13.0*** |
| A17D/R79T_DI 2 | 40.4**** | 10.5** |
| A17D/R79T_DI 3 | 44.9**** | 12.6*** |
| A17D/R79T_DI 4 | 43.7**** | 12.7*** |
| A17D/R79T_DI 5 | 32.6**** | 10.4* |
| A17D/R79T_DI 6 | 33.4**** | 12.2*** |
| A17D/R79T_DI 7 | 41.7**** | 14.1**** |
| A17D/R79T_DI 8 | 43.8**** | 10.0* |

Example 8

Pharmacokinetic Profile of Deimmunized Antibodies in Rat

Pharmacokinetic Profiles of BAN2401, A17D/R79T and Eight Deimmunized Variants of A17D/R79T (A17D/R79T DI 1-8) in Rats In order to compare the PK profiles of the eight variants of deimmunized A17D/R79T (A17D/R79T_DI 1-8) to the PK profile of BAN2401 and A17D/R79T in rats, 8 weeks old female Sprague Dawley rats were grouped (N=5) and subjected to single i.v. injections of 10 mg/kg antibody. Animals were bled after 0.5 h, 2 days, 7 days, 14 days and 28 days and levels of BAN2401 and antibodies of the invention were analysed by ELISA using Aβ1-40 for capture and HRP-coupled goat-anti-human IgG for detection (Example 1, direct ELISA).

As shown in FIG. 6, BAN2401, A17D/R79T and the deimmunized variants of A17D/R79T (A17D/R79T_DI 1-8) displayed fairly similar PK profiles in rat. Results suggested that A17D/R79T_DI 1 had a significantly longer terminal half-life than BAN2401 in rats ($p<0.05$), whereas $AUC_{0\text{-}inf}$ was significantly larger for A17D/R79T, A17D/R79T_DI 1 and A17D/R79T_DI 4 in comparison to BAN2401 ($p<0.01$) (Table 7).

TABLE 7

Plasma PK parameters of BAN2401, A17D/R79T and deimmunized variants of A17D/R79T (A17D/R79T_DI 1-8) in rats. Half-life and $AUC_{0\text{-}inf}$ for all antibodies were calculated individually for all animals by non-compartmental analysis using Phoenix WinNonlin 6.3 (Pharsight) and subjected to statistical analysis by one-way ANOVA followed by Bonferroni's Multiple Comparison post-test. Mean AUCs and mean terminal half-lives are shown in the table. Statistical differences in terminal half-life and AUC between BAN2401 and antibodies of the invention are indicated in the table, where * denotes $P < 0.05$ and **$P < 0.01$.

| Antibody | $AUC_{0\text{-}inf}$ (mg*h/ml) | Terminal half-life (days) |
|---|---|---|
| BAN2401 | 35.1 | 10.2 |
| A17D/R79T | 48.6** | 11.0 |
| A17D/R79T_DI 1 | 47.3** | 13.3* |
| A17D/R79T_DI 2 | 33.7 | 11.8 |
| A17D/R79T_DI 3 | 43.1 | 11.7 |

TABLE 7-continued

Plasma PK parameters of BAN2401, A17D/R79T and deimmunized variants of A17D/R79T (A17D/R79T_DI 1-8) in rats. Half-life and $AUC_{0-inf}$ for all antibodies were calculated individually for all animals by non-compartmental analysis using Phoenix WinNonlin 6.3 (Pharsight) and subjected to statistical analysis by one-way ANOVA followed by Bonferroni's Multiple Comparison post-test. Mean AUCs and mean terminal half-lives are shown in the table. Statistical differences in terminal half-life and AUC between BAN2401 and antibodies of the invention are indicated in the table, where * denotes $P < 0.05$ and **$P < 0.01$.

| Antibody | $AUC_{0-inf}$ (mg*h/ml) | Terminal half-life (days) |
|---|---|---|
| A17D/R79T_DI 4 | 47.3** | 11.7 |
| A17D/R79T_DI 5 | 44.1 | 11.6 |
| A17D/R79T_DI 6 | 39.6 | 11.3 |
| A17D/R79T_DI 7 | 35.6 | 11.8 |
| A17D/R79T_DI 8 | 40.9 | 10.6 |

Example 9

Pharmacokinetic Profile of Deimmunized Antibodies in Monkey

Pharmacokinetic Profiles of BAN2401, A17D/R79T_DI 3, A17D/R79T_DI 4 and A17D/R79T_DI 8 in Cynomolgus Monkeys.

Figure 7:
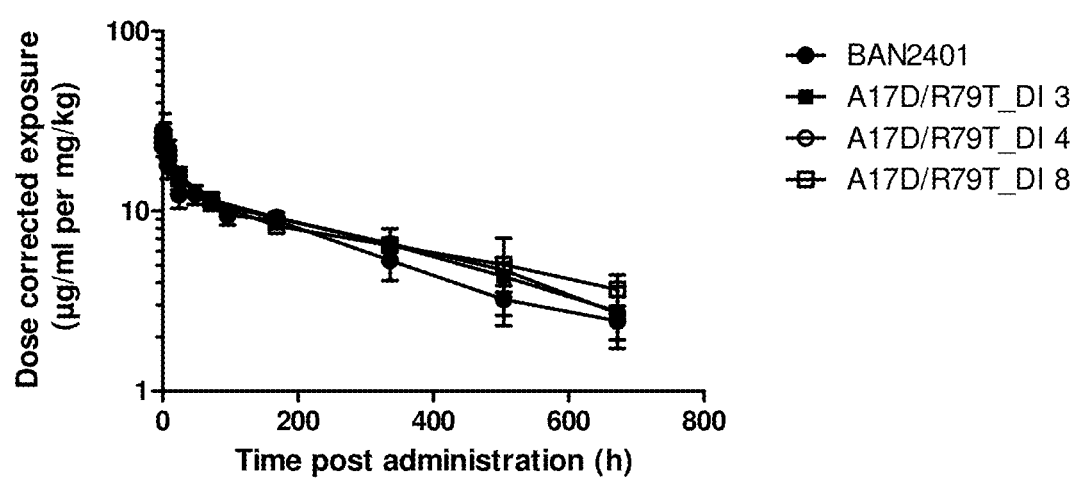
FIG. 7 provides dose corrected plasma drug exposure of BAN2401, A17D/R79T_DI 3, A17D/R79T_DI 4 and A17D/R79T_DI 8 in Cynomolgus monkey presented as time vs concentration graphs. Plasma evels of antibody after single i.v. infusion of BAN2401 collected at time points 5 min, 1 h, 2 h, 8 h, 24 h, 2 days, 4 days, 7 days, 14 days, 21 days and 28 days post administration, and A17D/R79T_DI 3, A17D/R79T_DI 4 and A17D/R79T_DI 8 collected at time points 5 min, 2 h, 8 h, 24 h, 3 days, 7 days, 14 days, 21 days and 28 days post administration. The antibodies of the invention were administered to the monkey in a different study and at a different dose (10 mg/kg) compared to BAN2401 (5 mg/kg). Therefore the plasma exposure graphs have been dose adjusted. The dose corrected plasma drug concentration in µg/ml per mg/kg injected dose is shown on the y-axis (logarithmic scale) and the time post administration in hours (h) is shown on the x-axis. Mean group values are shown with error bars indicating standard deviations. Dose adjusted mean $AUC_{0-inf}$ values and terminal half-lives were calculated by non-compartment analysis using Phoenix WinNonlin 6.3 (Pharsight) and are shown in Table 8.

In order to compare the PK profiles of A17D/R79T_DI 3, A17D/R79T_DI 4 and A17D/R79T_DI 8 to the PK profile of BAN2401 in monkeys, male cynomolgus monkeys were grouped (N=3) and subjected to single i.v. infusions of 5 mg/kg BAN2401 or 10 mg/kg of the antibodies of the invention. BAN2401 injected monkeys were bled after 5 min, 1 h, 2 h, 8 h, 24 h, 2 days, 4 days, 7 days, 14 days, 21 days and 28 days post administration, whereas the monkeys injected with the antibodies of the invention were bled after 5 min, 2 h, 8 h, 24 h, 3 days, 7 days, 14 days, 21 days and 28 days. Plasma concentration of the administered antibodies were analysed by ELISA as described in Example 1 (direct ELISA). The PK profiles are shown as time vs concentration graphs in FIG. 7, whereas half-life and $AUC_{0-inf}$ for all antibodies were calculated by non-compartment analysis using Phoenix WinNonlin 6.3 (Pharsight) (Table 8). PK parameters from BAN2401 shown in Table 8, are results from a separate study in which BAN2401 was administered by i.v. infusion at a dose of 5 mg/kg BAN2401.

TABLE 8

Plasma PK parameters of BAN2401, A17D/R79T_DI 3, A17D/R79T_DI 4 and A17D/R79T_DI 8 in cynomolgus monkeys. Terminal half-life and $AUC_{0-inf}$ for all antibodies were calculated by non-compartment analysis using Phoenix WinNonlin 6.3 (Pharsight). PK parameters from BAN2401 shown here is from a separate study in which BAN2401 was administered by i.v. infusion at a dose of 5 mg/kg BAN2401. To simplify AUC comparisons between BAN2401 and the antibodies of the invention dose adjusted mean $AUC_{0-inf}$ and mean terminal half-life values are shown in the table.

| Antibody | Dose corrected $AUC_{0-inf}$ (mg*h/ml) per (mg/kg) | Terminal half-life (days) |
|---|---|---|
| BAN2401 | 5.3 | 12.0 |
| A17D/R79T_DI 3 | 6.1 | 12.0 |
| A17D/R79T_DI 4 | 6.5 | 12.6 |
| A17D/R79T_DI 8 | 7.1 | 17.2 |

Example 10

Simple Allometric Scaling—Mouse, Rat and Monkey to Man

In order to predict human half-life of the antibodies of the invention (here shown for A17D/R79T_DI 3, A17D/R79T_DI 4 and A17D/R79T_DI 8), 2-comparmental modeling and simple allometric scaling were performed. A 2-compartmental model was applied to plasma PK profiles of BAN2401 and the antibodies of the invention using Phoenix WinNonlin 6.3 (Pharsight), in order to estimate clearance (CL) and volume (V) values in mouse rat and monkey. CL and V values were plotted versus body weight and simple allometric scaling was applied (Deng et al. mAbs 2011: 3(1): p. 61-66. doi:10.4161/mabs.3.1.13799). Terminal half-life was calculated following the equation:

$$t_{1/2} = \frac{\ln(2) * \text{Volume}}{\text{Clearance}}$$

In simple allometric scaling of volume or clearance, the values of the estimated parameters in preclinical species are plotted versus body weight. The constant and the exponent from the regression line are used to predict V and CL in man at a body weight of 70 kg. Both the exponent (which should preferably be around 0.85 for clearance and 1 for volume) and the adherence to the regression line are measures of confidence of the estimate of the specific parameters in man.

Figure 11:
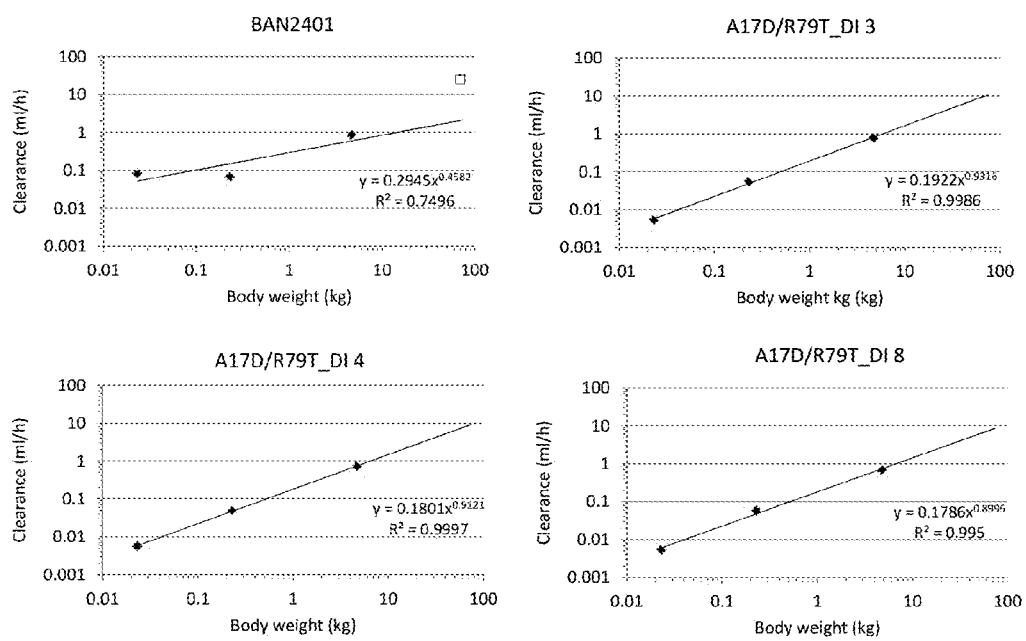
FIG. 11 provides simple allometric scaling of central clearance (CL) of BAN2401, A17D/R79T_DI 3, A17D/R79T_DI 4 and A17D/R79T_DI 8 including preclinical species mouse, rat and cynomolgus. The CLs of the different species are plotted against their weights (diamonds), respectively. The regression line has been extrapolated to indicate CL in a man with a body weight of 70 kg. For BAN2401 the true central CL measured is indicated by an open square, and deviates from the linear regression line based on CL of BAN2401 in mouse, rat and cynomolgus monkey. BAN2401 showed a poor linear correlation of CL indicating uncertain prediction of half-life, in contrast to the excellent linear correlation of CL of the antibodies of the invention.

As shown in FIG. 11, BAN2401 has a poor linear correlation of central CL among the species tested, resulting in uncertain simple allometric scaling. The deviation from the exponent (which should be close to 0.85) suggests that the poor correlation is an effect of the high clearance of BAN2401 in mice. This led to an underestimation of the expected CL in man and hence an overestimation of the predicted terminal half-life. The terminal half-life of BAN2401 was estimated to 41 days, which deviated considerably from the half-life measured in the clinic (5-7 days). The actual CL of BAN2401 has been indicated in FIG. 11 (open square). In contrast to the poor linear correlation between mouse, rat and cynomolgus for BAN2401, the antibodies of the invention (A17D/R79T_DI 3, A17D/R79T_DI 4 and A17D/R79T_DI 8) showed an excellent correlation (FIG. 11). The calculated terminal half-life from the predicted PK parameters in man suggested half-life in humans of 13, 15 and 20 days for A17D/R79T_DI 3, A17D/R79T_DI 4 and A17D/R79T_DI 8, respectively. Simple allometric scaling of volume (V) suggested good linear correlation and an exponent of approximately 1 for BAN2401 and the antibodies of the invention (not shown).

The antibodies of the invention show a linear correlation of CL among species with a more confident allometric scaling, and they behave like other therapeutic IgG1s, such as bevacizumab, omalizumab and trastuzumab, as described in Deng et al, Expert Opin. Drug Metab. Toxicol 8(2) (2012): p. 141-160, with half-lives in man of about 15-30 days. In contrast to BAN2401, with a suboptimal PK profile in mouse and man deviating from many other therapeutic IgG1s, the antibodies of the present invention have been engineered resulting in normalized PK profiles in mouse. They show PK profiles and half-lives in mouse, rat and cynomolgus similar to other therapeutic IgG1s with half-lives in man of about 15-30 days. This finding would suggest that the prolonged half-life of the antibodies of the invention in mice will translate to man.

The invention claimed is:

1. An antibody or antigen binding fragment thereof having affinity against Aβ protofibrils, wherein the antibody or antigen binding fragment thereof has a variable light chain according to SEQ ID NO: 8, wherein $x_1$ (Xaa at position 17 of SEQ ID NO:8) is selected from A, D, E and Q, or a functional analogue thereof;

$x_2$ (Xaa at position 79 of SEQ ID NO:8) is selected from R, T, K, A and G, or a functional analogue thereof;

$x_3$ (Xaa at position 82 of SEQ ID NO:8) is selected from R, S, C, G and N, or a functional analogue thereof;

$y_1$ (Xaa at position 13 of SEQ ID NO:8) is selected from V and A;

$y_2$ (Xaa at position 21 of SEQ ID NO:8) is selected from I and V;

$y_3$ (Xaa at position 81 of SEQ ID NO:8) is selected from S and Q;

$y_4$ (Xaa at position 84 of SEQ ID NO:8) is selected from E and D; and optionally a variable heavy chain according to SEQ ID NO: 14, wherein $z_1$ (Xaa at position 37 of SEQ ID NO:14) is selected from V and I;

$z_2$ (Xaa at position 38 of SEQ ID NO:14) is selected from R and Q; and $z_3$ (Xaa at position 40 of SEQ ID NO:14) is selected from A, N and T;

with the exception for the combination $x_1$=A, $x_2$=R and $x_3$=R.

2. The antibody or antigen binding fragment according to claim 1, wherein $x_1$ is selected from A, D, E and Q;

$x_2$ is selected from R, T, K, A and G;

$x_3$ is selected from R, S, C, G and N;

$y_1$ is selected from V and A;

$y_2$ is selected from I and V;

$y_3$ is selected from S and Q; and $y_4$ is selected from E and D;

with the exception for the combination $x_1$=A, $x_2$=R and $x_3$=R.

3. The antibody or antigen binding fragment according to claim 1, wherein $x_1$ is D;

$x_2$ is T;

$x_3$ is R;

$y_1$ is selected from V and A;

$y_2$ is selected from V and I;
$y_3$ is selected from Q and S;
$y_4$ is selected from D and E;
$z_1$ is V;
$z_2$ is R; and
$z_3$ is selected from N, T and A;
with exclusion of the combination wherein $y_1$ is V, $y_2$ is I, $y_3$, is S, $y_4$ is E, $z_1$ is V, $z_2$ is R and $z_3$ is A.

4. An antibody or antigen binding fragment thereof, according to claim 1, comprising a variable light chain comprising the amino acid sequence as set out in SEQ ID NO: 9; and a variable heavy chain comprising the amino acid sequence as set out in SEQ ID NO: 15.

5. An antibody or antigen binding fragment thereof, according to claim 1, comprising a variable light chain comprising the amino acid sequence as set out in SEQ ID NO: 10; and a variable heavy chain comprising the amino acid sequence as set out in SEQ ID NO: 15.

6. An antibody or antigen binding fragment thereof, according to claim 1, comprising a variable light chain comprising the amino acid sequence as set out in SEQ ID NO: 11; and a variable heavy chain comprising the amino acid sequence as set out in SEQ ID NO: 15.

7. An antibody or antigen binding fragment thereof, according to claim 1, comprising a variable light chain comprising the amino acid sequence as set out in SEQ ID NO: 12; and a variable heavy chain comprising the amino acid sequence as set out in SEQ ID NO: 15.

8. An antibody or antigen binding fragment thereof, according to claim 1, comprising a variable light chain comprising the amino acid sequence as set out in SEQ ID NO: 9; and a variable heavy chain comprising the amino acid sequence as set out in SEQ ID NO: 16.

9. An antibody or antigen binding fragment thereof, according to claim 1, comprising a variable light chain comprising the amino acid sequence as set out in SEQ ID NO: 10; and a variable heavy chain comprising the amino acid sequence as set out in SEQ ID NO: 16.

10. An antibody or antigen binding fragment thereof, according to claim 1, comprising a variable light chain comprising the amino acid sequence as set out in SEQ ID NO: 11; and a variable heavy chain comprising the amino acid sequence as set out in SEQ ID NO: 16.

11. The antibody or antigen binding fragment according to claim 1, wherein the antibody or the antigen binding fragment comprises an IgG heavy chain constant region.

12. A pharmaceutical composition comprising the antibody or antigen binding fragment according to claim 2, together with a pharmaceutically acceptable excipient and/or diluent.

13. A method of reducing the amount of Aβ protofibrils in a subject, comprising administering to said subject a therapeutically effective amount of the antibody or antigen binding fragment according to claim 2.

14. The method according to claim 13, wherein the subject is a veterinary subject.

15. A method for treatment of Alzheimer's disease or another disorder associated with Aβ protein aggregation in a subject having said disease or disorder, comprising administering to said subject a therapeutically effective amount of the antibody or antigen binding fragment according to claim 2.

16. A method for treatment of Down syndrome (DS) in a subject comprising administering to said subject a therapeutically effective amount of the antibody or antigen binding fragment according to claim 2.

17. A method for measuring the amount of Aβ protofibrils and/or aggregated Aβ protein in a person, comprising contacting the person's tissue or body fluid, in vivo or in vitro, with the antibody or antigen binding fragment according to claim 2 and measuring the amount of antibody or antigen binding fragment bound to said Aβ protofibrils and/or aggregated Aβ protein.

18. A method for diagnosis of Alzheimer's disease in a person having or at risk of developing the disease, comprising contacting the person's tissue or body fluid, in vivo or in vitro, with the antibody or antigen binding fragment according to claim 2, or a fragment thereof, and measuring the amount of said antibody or antigen binding fragment bound to aggregated Aβ protein.

19. A method for diagnosis of Down syndrome (DS) in a person, comprising contacting the person's tissue or body fluid, in vivo or in vitro, with the antibody or antigen binding fragment according to claim 2, and measuring the amount of said antibody or antigen binding fragment bound to aggregated Aβ protein.

20. An antibody or antigen binding fragment thereof having affinity against Aβ protofibrils, wherein the antibody or antigen binding fragment thereof comprises a variable light chain comprising the amino acid sequence as set out in SEQ ID NO: 12 and a variable heavy chain comprising the amino acid sequence as set out in SEQ ID NO: 16.

21. The antibody according to claim 20, wherein the antibody or antigen binding fragment thereof comprises an IgG heavy chain constant region.

22. A pharmaceutical composition comprising the antibody or antigen binding fragment thereof according to claim 20, together with a pharmaceutically acceptable excipient and/or diluent.

23. A method of reducing the amount of Aβ protofibrils in a subject, comprising administering to said subject a therapeutically effective amount of the antibody or antigen binding fragment thereof according to claim 20.

24. A method for treatment of Alzheimer's disease or another disorder associated with Aβ protein aggregation in a subject having said disease or disorder, comprising administering to said subject a therapeutically effective amount of the antibody or antigen binding fragment thereof according to claim 20.

25. A method for treatment of Alzheimer's disease in a subject having Alzheimer's disease, comprising administering to said subject a therapeutically effective amount of the antibody or antigen binding fragment thereof according to claim 20.

* * * * *

UNITED STATES PATENT AND TRADEMARK OFFICE
CERTIFICATE OF CORRECTION

PATENT NO. : 9,573,994 B2
APPLICATION NO. : 14/794172
DATED : February 21, 2017
INVENTOR(S) : Charlotte Nerelius et al.

It is certified that error appears in the above-identified patent and that said Letters Patent is hereby corrected as shown below:

On the Title Page

Page 3, in El-Agnaf et al., replace "Faseb J. 20(3):419-25 (2006)." with --FASEB J. 20(3):419-25 (2006).--.

Page 4, in Klyubin et al., replace "Inhibitory effect of amyloid-beta peptide with the Arctic mutuation on long-term potentiation in area CA1 of rat hippocampus in vivo," with --Inhibitory effect of amyloid-beta peptide with the Arctic mutation on long-term potentiation in area CA1 of rat hippocampus in vivo,--.

Page 5, in Nilsberth et al., "The Arctic APP Mutation (E693G) Causes Alzheimer's Disease Through a Novel Mechanism...", replace "BetaProtfibril" with --Beta Protofibril--.

In the Specification

Column 3, Line 50, replace "chain a comprises a" with --chain comprises a--.

Column 4, Line 21, replace "y3, is S," with --y3 is S,--.

Column 5, Line 7, replace "Downs syndrome" with --Down syndrome--.

Line 18, replace "Downs syndrome" with --Down syndrome--.

Column 7, Line 26, replace "Plasma evels" with --Plasma levels--.

Column 12, Lines 20-21, replace "$y_3$, is S," with --$y_3$ is S--.

Signed and Sealed this
Fourteenth Day of November, 2017

Joseph Matal
*Performing the Functions and Duties of the
Under Secretary of Commerce for Intellectual Property and
Director of the United States Patent and Trademark Office*

Column 16, Line 56, replace "propfylaxis" with --prophylaxis--.

Column 20, Lines 11-12, replace "WinNonLin" with --WinNonlin--.

Lines 13-14, replace "WinNonLin" with --WinNonlin--.

Column 30, Line 13, replace "in mouse rat and" with --in mouse, rat, and--.

Column 47, in SEQ ID NO 23, replace "Lys Ala Leu Pro Ala Pro Ile Glu Lys Thr Ile Ser Lys Ala Lys Gly 210 215 220" with -- Lys Ala Leu Pro Ala Pro Ile Glu Lys Thr Ile Ser Lys Ala Lys Gly 210 215 220 --.

In the Claims

Column 51, Claim 3, Line 8, replace "$y_3$, is S," with --$y_3$ is S,--.

Column 52, Claim 19, Line 26, replace "according to claim 2, and measuring" with --according to claim 2, or a fragment thereof, and measuring--.

SEQUENCE LISTING

<160> NUMBER OF SEQ ID NOS: 24

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser Phe Gly Met His
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Tyr Ile Ser Ser Gly Ser Ser Thr Ile Tyr Tyr Gly Asp Thr Val Lys
1               5                   10                  15

Gly

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Gly Gly Tyr Tyr Tyr Gly Arg Ser Tyr Tyr Thr Met Asp Tyr
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Arg Ser Ser Gln Ser Ile Val His Ser Asn Gly Asn Thr Tyr Leu Glu
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Lys Val Ser Asn Arg Phe Ser
1               5

<210> SEQ ID NO 6
<211> LENGTH: 9
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 6

Phe Gln Gly Ser His Val Pro Pro Thr
1               5

<210> SEQ ID NO 7
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Val Val Met Thr Gln Ser Pro Leu Ser Leu Pro Val Thr Pro Gly
1               5                   10                  15

Ala Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Phe Gln Gly
                85                  90                  95

Ser His Val Pro Pro Thr Phe Gly Pro Gly Thr Lys Leu Glu Ile Lys
            100                 105                 110

<210> SEQ ID NO 8
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (13)..(13)
<223> OTHER INFORMATION: Xaa can be Val or Ala
<220> FEATURE:
<221> NAME/KEY: MISC_FEATURE
<222> LOCATION: (17)..(17)
<223> OTHER INFORMATION: Xaa can be Ala, Asp, Glu, Gln or a functional
      analogue thereof
<220> FEATURE:
<221> NAME/KEY: MISC_FEATURE
<222> LOCATION: (21)..(21)
<223> OTHER INFORMATION: Xaa can be Ile or Val
<220> FEATURE:
<221> NAME/KEY: MISC_FEATURE
<222> LOCATION: (79)..(79)
<223> OTHER INFORMATION: Xaa can be Arg, Thr, Lys, Ala, Gly or a
      functional analogue thereof
<220> FEATURE:
<221> NAME/KEY: MISC_FEATURE
<222> LOCATION: (81)..(81)
<223> OTHER INFORMATION: Xaa can be Ser or Gln
<220> FEATURE:
<221> NAME/KEY: MISC_FEATURE
<222> LOCATION: (82)..(82)
<223> OTHER INFORMATION: Xaa can be Arg, Ser, Cys, Gly, Asn or a
      functional analogue
      thereof
<220> FEATURE:
<221> NAME/KEY: MISC_FEATURE
```

<222> LOCATION: (84)..(84)
<223> OTHER INFORMATION: Xaa can be Glu or Asp

<400> SEQUENCE: 8

Asp Val Val Met Thr Gln Ser Pro Leu Ser Leu Pro Xaa Thr Pro Gly
1               5                   10                  15

Xaa Pro Ala Ser Xaa Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Xaa Ile
65                  70                  75                  80

Xaa Xaa Val Xaa Ala Glu Asp Val Gly Ile Tyr Tyr Cys Phe Gln Gly
                85                  90                  95

Ser His Val Pro Pro Thr Phe Gly Pro Gly Thr Lys Leu Glu Ile Lys
            100                 105                 110

<210> SEQ ID NO 9
<211> LENGTH: 112
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 9

Asp Val Val Met Thr Gln Ser Pro Leu Ser Leu Pro Val Thr Pro Gly
1               5                   10                  15

Asp Pro Ala Ser Val Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Gln Arg Val Glu Ala Glu Asp Val Gly Ile Tyr Tyr Cys Phe Gln Gly
                85                  90                  95

Ser His Val Pro Pro Thr Phe Gly Pro Gly Thr Lys Leu Glu Ile Lys
            100                 105                 110

<210> SEQ ID NO 10
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Val Val Met Thr Gln Ser Pro Leu Ser Leu Pro Val Thr Pro Gly
1               5                   10                  15

Asp Pro Ala Ser Val Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro

```
                    50                  55                  60
Asp Arg Phe Ser Gly Ser Gly Ser Gly Thr Asp Phe Thr Leu Thr Ile
 65                  70                  75                  80

Ser Arg Val Asp Ala Glu Asp Val Gly Ile Tyr Tyr Cys Phe Gln Gly
                 85                  90                  95

Ser His Val Pro Pro Thr Phe Gly Pro Gly Thr Lys Leu Glu Ile Lys
            100                 105                 110

<210> SEQ ID NO 11
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Val Val Met Thr Gln Ser Pro Leu Ser Leu Pro Ala Thr Pro Gly
 1                   5                  10                  15

Asp Pro Ala Ser Ile Ser Cys Arg Ser Ser Gln Ser Ile Val His Ser
                 20                  25                  30

Asn Gly Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Thr Ile
 65                  70                  75                  80

Gln Arg Val Glu Ala Glu Asp Val Gly Ile Tyr Tyr Cys Phe Gln Gly
                 85                  90                  95

Ser His Val Pro Pro Thr Phe Gly Pro Gly Thr Lys Leu Glu Ile Lys
            100                 105                 110

<210> SEQ ID NO 12
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Val Val Met Thr Gln Ser Pro Leu Ser Leu Pro Ala Thr Pro Gly
 1                   5                  10                  15

Asp Pro Ala Ser Ile Ser Cys Arg Ser Ser Gln Ser Ile Val His Ser
                 20                  25                  30

Asn Gly Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Thr Ile
 65                  70                  75                  80

Ser Arg Val Asp Ala Glu Asp Val Gly Ile Tyr Tyr Cys Phe Gln Gly
                 85                  90                  95

Ser His Val Pro Pro Thr Phe Gly Pro Gly Thr Lys Leu Glu Ile Lys
            100                 105                 110

<210> SEQ ID NO 13
<211> LENGTH: 124
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Ser Thr Ile Tyr Tyr Gly Asp Thr Val
    50                  55                  60

Lys Gly Arg Phe Thr Ile Ser Arg Asp Asn Ala Lys Asn Ser Leu Phe
65                  70                  75                  80

Leu Gln Met Ser Ser Leu Arg Ala Glu Asp Thr Ala Val Tyr Tyr Cys
                85                  90                  95

Ala Arg Glu Gly Gly Tyr Tyr Tyr Gly Arg Ser Tyr Tyr Thr Met Asp
            100                 105                 110

Tyr Trp Gly Gln Gly Thr Thr Val Thr Val Ser Ser
        115                 120

<210> SEQ ID NO 14
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (37)..(37)
<223> OTHER INFORMATION: Xaa can be Val or Ile
<220> FEATURE:
<221> NAME/KEY: MISC_FEATURE
<222> LOCATION: (38)..(38)
<223> OTHER INFORMATION: Xaa can be Arg or Gln
<220> FEATURE:
<221> NAME/KEY: MISC_FEATURE
<222> LOCATION: (40)..(40)
<223> OTHER INFORMATION: Xaa can be Ala, Asn or Thr

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Phe
            20                  25                  30

Gly Met His Trp Xaa Xaa Gln Xaa Pro Gly Lys Gly Leu Glu Trp Val
        35                  40                  45

Ala Tyr Ile Ser Ser Gly Ser Ser Thr Ile Tyr Tyr Gly Asp Thr Val
    50                  55                  60

Lys Gly Arg Phe Thr Ile Ser Arg Asp Asn Ala Lys Asn Ser Leu Phe
65                  70                  75                  80

Leu Gln Met Ser Ser Leu Arg Ala Glu Asp Thr Ala Val Tyr Tyr Cys
                85                  90                  95

Ala Arg Glu Gly Gly Tyr Tyr Tyr Gly Arg Ser Tyr Tyr Thr Met Asp
            100                 105                 110

Tyr Trp Gly Gln Gly Thr Thr Val Thr Val Ser Ser
        115                 120

<210> SEQ ID NO 15
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Glu Val Gln Leu Val Glu Ser Gly Gly Leu Val Gln Pro Gly Gly
1               5                   10                  15

Ser Leu Arg Leu Ser Cys Ser Ala Ser Gly Phe Thr Phe Ser Ser Phe
            20                  25                  30

Gly Met His Trp Val Arg Gln Asn Pro Gly Lys Gly Leu Glu Trp Val
        35                  40                  45

Ala Tyr Ile Ser Ser Gly Ser Ser Thr Ile Tyr Tyr Gly Asp Thr Val
    50                  55                  60

Lys Gly Arg Phe Thr Ile Ser Arg Asp Asn Ala Lys Asn Ser Leu Phe
65                  70                  75                  80

Leu Gln Met Ser Ser Leu Arg Ala Glu Asp Thr Ala Val Tyr Tyr Cys
                85                  90                  95

Ala Arg Glu Gly Gly Tyr Tyr Tyr Gly Arg Ser Tyr Tyr Thr Met Asp
            100                 105                 110

Tyr Trp Gly Gln Gly Thr Thr Val Thr Val Ser Ser
        115                 120
```

<210> SEQ ID NO 16
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Glu Val Gln Leu Val Glu Ser Gly Gly Leu Val Gln Pro Gly Gly
1               5                   10                  15

Ser Leu Arg Leu Ser Cys Ser Ala Ser Gly Phe Thr Phe Ser Ser Phe
            20                  25                  30

Gly Met His Trp Val Arg Gln Thr Pro Gly Lys Gly Leu Glu Trp Val
        35                  40                  45

Ala Tyr Ile Ser Ser Gly Ser Ser Thr Ile Tyr Tyr Gly Asp Thr Val
    50                  55                  60

Lys Gly Arg Phe Thr Ile Ser Arg Asp Asn Ala Lys Asn Ser Leu Phe
65                  70                  75                  80

Leu Gln Met Ser Ser Leu Arg Ala Glu Asp Thr Ala Val Tyr Tyr Cys
                85                  90                  95

Ala Arg Glu Gly Gly Tyr Tyr Tyr Gly Arg Ser Tyr Tyr Thr Met Asp
            100                 105                 110

Tyr Trp Gly Gln Gly Thr Thr Val Thr Val Ser Ser
        115                 120
```

<210> SEQ ID NO 17
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Phe
            20                  25                  30

Gly Met His Trp Val Gln Gln Ala Pro Gly Lys Gly Leu Glu Trp Val
        35                  40                  45

Ala Tyr Ile Ser Ser Gly Ser Ser Thr Ile Tyr Tyr Gly Asp Thr Val
    50                  55                  60

Lys Gly Arg Phe Thr Ile Ser Arg Asp Asn Ala Lys Asn Ser Leu Phe
65                  70                  75                  80

Leu Gln Met Ser Ser Leu Arg Ala Glu Asp Thr Ala Val Tyr Tyr Cys
                85                  90                  95

Ala Arg Glu Gly Gly Tyr Tyr Tyr Gly Arg Ser Tyr Tyr Thr Met Asp
            100                 105                 110

Tyr Trp Gly Gln Gly Thr Thr Val Thr Val Ser Ser
        115                 120

<210> SEQ ID NO 18
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Phe
            20                  25                  30

Gly Met His Trp Ile Arg Gln Ala Pro Gly Lys Gly Leu Glu Trp Val
        35                  40                  45

Ala Tyr Ile Ser Ser Gly Ser Ser Thr Ile Tyr Tyr Gly Asp Thr Val
    50                  55                  60

Lys Gly Arg Phe Thr Ile Ser Arg Asp Asn Ala Lys Asn Ser Leu Phe
65                  70                  75                  80

Leu Gln Met Ser Ser Leu Arg Ala Glu Asp Thr Ala Val Tyr Tyr Cys
                85                  90                  95

Ala Arg Glu Gly Gly Tyr Tyr Tyr Gly Arg Ser Tyr Tyr Thr Met Asp
            100                 105                 110

Tyr Trp Gly Gln Gly Thr Thr Val Thr Val Ser Ser
        115                 120

<210> SEQ ID NO 19
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Val Val Met Thr Gln Ser Pro Leu Ser Leu Pro Val Thr Pro Gly
1               5                   10                  15

Asp Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

```
Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Phe Gln Gly
                85                  90                  95

Ser His Val Pro Pro Thr Phe Gly Pro Gly Thr Lys Leu Glu Ile Lys
            100                 105                 110

<210> SEQ ID NO 20
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Val Val Met Thr Gln Ser Pro Leu Ser Leu Pro Val Thr Pro Gly
1               5                   10                  15

Asp Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Arg Val Glu Ala Glu Asp Val Gly Ile Tyr Tyr Cys Phe Gln Gly
                85                  90                  95

Ser His Val Pro Pro Thr Phe Gly Pro Gly Thr Lys Leu Glu Ile Lys
            100                 105                 110

<210> SEQ ID NO 21
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

Asp Val Val Met Thr Gln Ser Pro Leu Ser Leu Pro Val Thr Pro Gly
1               5                   10                  15

Asp Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Val Glu Ala Glu Asp Val Gly Ile Tyr Tyr Cys Phe Gln Gly
                85                  90                  95

Ser His Val Pro Pro Thr Phe Gly Pro Gly Thr Lys Leu Glu Ile Lys
            100                 105                 110

<210> SEQ ID NO 22
<211> LENGTH: 112
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Val Val Met Thr Gln Ser Pro Leu Ser Leu Pro Val Thr Pro Gly
1               5                   10                  15

Asp Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Ser Val Glu Ala Glu Asp Val Gly Ile Tyr Tyr Cys Phe Gln Gly
                85                  90                  95

Ser His Val Pro Pro Thr Phe Gly Pro Gly Thr Lys Leu Glu Ile Lys
            100                 105                 110

<210> SEQ ID NO 23
<211> LENGTH: 330
<212> TYPE: PRT
<213> ORGANISM: Homo sapiens

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 24
<211> LENGTH: 107
<212> TYPE: PRT
<213> ORGANISM: Homo sapiens

<400> SEQUENCE: 24

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105
```